United States Patent
Ueda et al.

(10) Patent No.: US 12,343,031 B2
(45) Date of Patent: Jul. 1, 2025

(54) TREATMENT TOOL FOR ENDOSCOPE

(71) Applicant: FUJIFILM Corporation, Tokyo (JP)

(72) Inventors: Yoshihiro Ueda, Kanagawa (JP);
Keiichiro Takahashi, Kanagawa (JP);
Jun Sato, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 635 days.

(21) Appl. No.: 17/650,344

(22) Filed: Feb. 8, 2022

(65) Prior Publication Data
US 2022/0160387 A1 May 26, 2022

Related U.S. Application Data

(63) Continuation of application No. PCT/JP2020/033682, filed on Sep. 4, 2020.

(60) Provisional application No. 63/064,894, filed on Aug. 12, 2020, provisional application No. 62/896,584, filed on Sep. 6, 2019.

(51) Int. Cl.
*A61B 17/29* (2006.01)

(52) U.S. Cl.
CPC ...... *A61B 17/29* (2013.01); *A61B 2017/2905* (2013.01); *A61B 17/2909* (2013.01); *A61B 2017/2944* (2013.01)

(58) Field of Classification Search
CPC ............... A61B 17/29; A61B 17/2909; A61B 2017/2905; A61B 2017/2944; A61B 2017/00367; A61B 2017/00389; A61B 2017/2919; A61B 2017/00314
See application file for complete search history.

(56) References Cited

U.S. PATENT DOCUMENTS

| 6,458,074 | B1 | 10/2002 | Matsui et al. |
| 10,610,345 | B2 * | 4/2020 | Cardinale ............ A61F 2/0063 |
| 2008/0125803 | A1 | 5/2008 | Sadamasa et al. |

(Continued)

FOREIGN PATENT DOCUMENTS

| JP | H09-276283 A | 10/1997 |
| JP | 2001-212078 A | 8/2001 |

(Continued)

OTHER PUBLICATIONS

International Search Report issued in PCT/JP2020/033682; mailed Dec. 1, 2020.

(Continued)

*Primary Examiner* — Brooke Labranche
(74) *Attorney, Agent, or Firm* — Studebaker Brackett PLLC

(57) ABSTRACT

A treatment tool for an endoscope includes a transmitting part that transmits an operation of an operating part to a grip part and a bendable part of a distal end part. The transmitting part has a first transmitting member hat is moved to an operating part side based on the operation of the operating part and closes the grip part and a second transmitting member that is moved to the operating part side based on the operation of the operating part and bends the bendable part. In response to the operation of the operating part, first, the first transmitting member is moved to the operating part side, and the second transmitting member is moved to the operating part side after the start of the movement of the first transmitting member.

3 Claims, 49 Drawing Sheets

(56) References Cited

U.S. PATENT DOCUMENTS

2009/0112229 A1   4/2009   Omori et al.
2010/0262181 A1   10/2010  Choi et al.

FOREIGN PATENT DOCUMENTS

| JP | 2002-330973 A | | 11/2002 |
|----|---------------|---|---------|
| JP | 2005224392 A | * | 8/2005 |
| JP | 2006-340782 A | | 12/2006 |
| JP | 2009-106606 A | | 5/2009 |
| JP | 2011-087911 A | | 5/2011 |

OTHER PUBLICATIONS

International Preliminary Report On Patentability (Chapter II) issued in PCT/JP2020/033682; completed Apr. 1, 2021.
An Office Action; "Notice of Reasons for Refusal," mailed by the Japanese Patent Office on Dec. 6, 2022, which corresponds to Japanese Patent Application No. 2021-544067 and is related to U.S. Appl. No. 17/650,344; with English language translation.

* cited by examiner

TREATMENT TOOL FOR ENDOSCOPE

CROSS REFERENCE TO RELATED APPLICATION

This is a continuation of International Application No. PCT/JP2020/033682 filed on Sep. 4, 2020, and claims priority from U.S. Provisional Application No. 62/896,584 filed on Sep. 6, 2019 and U.S. Provisional Application No. 63/064,894 filed on Aug. 12, 2020, the entire disclosures of which are incorporated herein by reference.

BACKGROUND OF THE INVENTION

1. Field of the Invention

The present invention relates to a treatment tool for an endoscope.

2. Description of the Related Art

Various types of treatment are performed on a living body by combining an endoscope and a treatment tool for an endoscope. As an example of treatment, endoscopic submucosal dissection (ESD) is known. An interior wall such as the esophagus, stomach, and large intestine to which ESD is applied consists of three layers including a mucous membrane layer, a submucosal layer, and a muscular layer. In ESD, a lesion part of the mucous membrane layer including the submucosal layer is peeled off, and it is also possible to collectively excise, for example, a relatively large lesion part which exceeds 2 cm.

An endoscope described in JP2001-212078A is used in, for example, ESD, and comprises a first treatment tool insertion channel and a second treatment tool insertion channel. The first treatment tool insertion channel is open to a distal end of an insertion part of the endoscope, and a first erecting mechanism that erects a treatment tool in a first direction (for example, an up-and-down direction) is provided at a distal end opening portion of the first treatment tool insertion channel. Also the second treatment tool insertion channel is open to the distal end of the insertion part of the endoscope, and a second erecting mechanism that erects the treatment tool in a second direction (for example, a right-and-left direction) different from the first direction is provided at a distal end opening portion of the second treatment tool channel.

In a case where the endoscope described in JP2001-212078A is used in ESD, a grip forcep is inserted into the first treatment tool insertion channel, and an incision tool such as an electric scalpel is inserted into the second treatment tool insertion channel. The grip forcep and the incision tool approach a lesion part from the side of the lesion part along the interior wall. First, as the lesion part is gripped by the grip forcep and the grip forcep gripping the lesion part is erected by the first erecting mechanism of the endoscope, the lesion part is lifted. Then, as a lower part of the lifted lesion part is incised by the incision tool and the incision tool is swung right and left by the second erecting mechanism of the endoscope, incision proceeds. In this manner, the lesion part including the submucosal layer is gradually peeled off.

In addition, also a treatment tool for an endoscope that can perform treatment including both of gripping and incision is known. A treatment tool for an endoscope described in JP2002-330973A comprises a sheath, a forcep member provided at a distal end part of the sheath, and a high-frequency knife inserted in the sheath. The forcep member is opened and closed by a first operating part provided at a proximal end part of the sheath. The high-frequency knife protrudes from between a pair of arm portions of the forcep member and is moved forward and backward in an axial direction of the sheath by a second operating part provided at the proximal end part of the sheath.

SUMMARY OF THE INVENTION

In the endoscope described in JP2001-212078A, in order to grip and lift the lesion part, an operation of the grip forcep for gripping the lesion part and an operation of the endoscope for erecting the grip forcep are necessary, thereby complicating the operation.

The treatment tool for an endoscope described in JP2002-330973A can only pull the lesion part gripped by the forcep member in the axial direction of the sheath with an operation of the treatment tool alone. A bending operation of the endoscope is necessary to lift the lesion part, and the visual field of the endoscope moves in response to the bending operation of the endoscope, thereby increasing the difficulty of treatment.

The present invention is devised in view of the circumstances described above, and an object thereof is to provide a treatment tool for an endoscope that can easily perform gripping of a lesion part and lifting of the gripped lesion part with an operation of the treatment tool alone.

According to an aspect of the present invention, there is provided a treatment tool for an endoscope comprising an insertion part that has a distal end part, which is provided with an openable and closable grip part, and a bendable part, which is provided adjacent to the distal end part and is bendable, and that is insertable into a body, an operating part into which an operation of closing the grip part and an operation of bending the bendable part are input, and a transmitting part that transmits an operation of the operating part to the grip part and the bendable part. The transmitting part has a first transmitting member that extends from the grip part toward the operating part, is moved in a first direction, which is an operating part side or a distal end part side, based on the operation of the operating part, and closes the grip part by moving in the first direction, a second transmitting member that extends from the bendable part toward the operating part, is moved in the first direction based on the operation of the operating part, and bends the bendable part by moving in the first direction, a first movable body that is connected to the first transmitting member and is moved in the first direction based on the operation of the operating part, and a second movable body that is connected to the second transmitting member and is moved in the first direction based on the operation of the operating part. In response to the operation of the operating part, first, the first movable body is moved in the first direction, and the second movable body is moved in the first direction after start of a movement of the first movable body.

With the present invention, it is possible to provide the treatment tool for an endoscope that can easily perform gripping of a lesion part and lifting of the gripped lesion part with an operation of the treatment tool alone.

DESCRIPTION OF THE PREFERRED EMBODIMENTS

Embodiment 1

Figure 1:
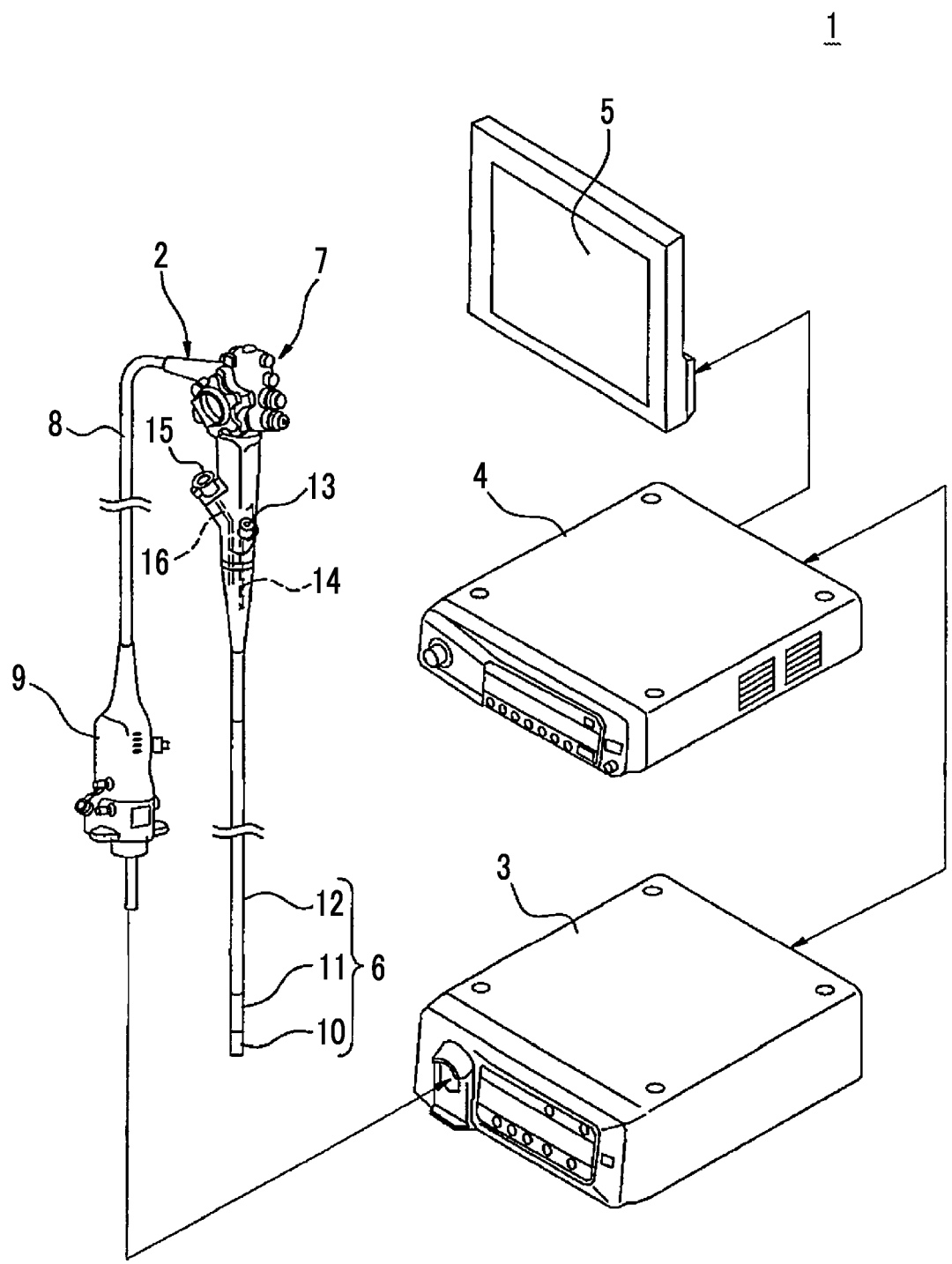
FIG. 1 is a view showing an example of an endoscope system, which is for describing Embodiment 1 of the present invention.

FIG. 1 shows an example of an endoscope system for describing Embodiment 1 of the present invention.

An endoscope system 1 comprises an endoscope 2, a light source device 3, and a processor 4. The endoscope 2 has an endoscope insertion part 6 that is inserted into a subject, an endoscope operating part 7 that is connected to the endoscope insertion part 6, and a universal cord 8 that extends from the endoscope operating part 7. The endoscope insertion part 6 is composed of an endoscope distal end part 10, an endoscope bendable part 11 that is connected to the endoscope distal end part 10, and an endoscope soft portion 12 that connects the endoscope bendable part 11 to the endoscope operating part 7.

An imaging apparatus including an imaging element is mounted on the endoscope distal end part 10. The endoscope bendable part 11 is configured to be bendable, and the bending of the endoscope bendable part 11 is operated by the endoscope operating part 7. In addition, the endoscope soft portion 12 is soft enough to be deformable along a shape of an insertion passage in the subject.

The endoscope operating part 7 is provided with an operation button for operating image pick-up using the imaging apparatus and an operation knob for operating the bending of the endoscope bendable part 11. In addition, the endoscope operating part 7 is provided with a first treatment tool insertion opening 13 and a second treatment tool insertion opening 15, into which the treatment tool for an endoscope is insertable. Inside the endoscope insertion part 6, a first treatment tool channel 14 that reaches the endoscope distal end part 10 from the first treatment tool insertion opening 13 and is open to an edge surface of the endoscope distal end part 10 and a second treatment tool channel 16 that reaches the endoscope distal end part 10 from the second treatment tool insertion opening 15 and is open to the edge surface of the endoscope distal end part 10 are provided.

A light guide and a cable are provided inside the endoscope insertion part 6, the endoscope operating part 7, and the universal cord 8. A connector 9 is provided at a terminal of the universal cord 8. The endoscope 2 is connected to the light source device 3 and the processor 4 via the connector 9.

Illumination light generated by the light source device 3 is guided to the endoscope distal end part 10 via the light guide and is emitted from the endoscope distal end part 10. In addition, operating power of the imaging element, a control signal for driving the imaging element, and an image signal output from the imaging element are transmitted between the processor 4 and the imaging apparatus via the cable. The processor 4 processes the input image signal to generate image data of an observation site in the subject, displays the generated image data on a monitor 5, and records the generated image data.

Figure 2:
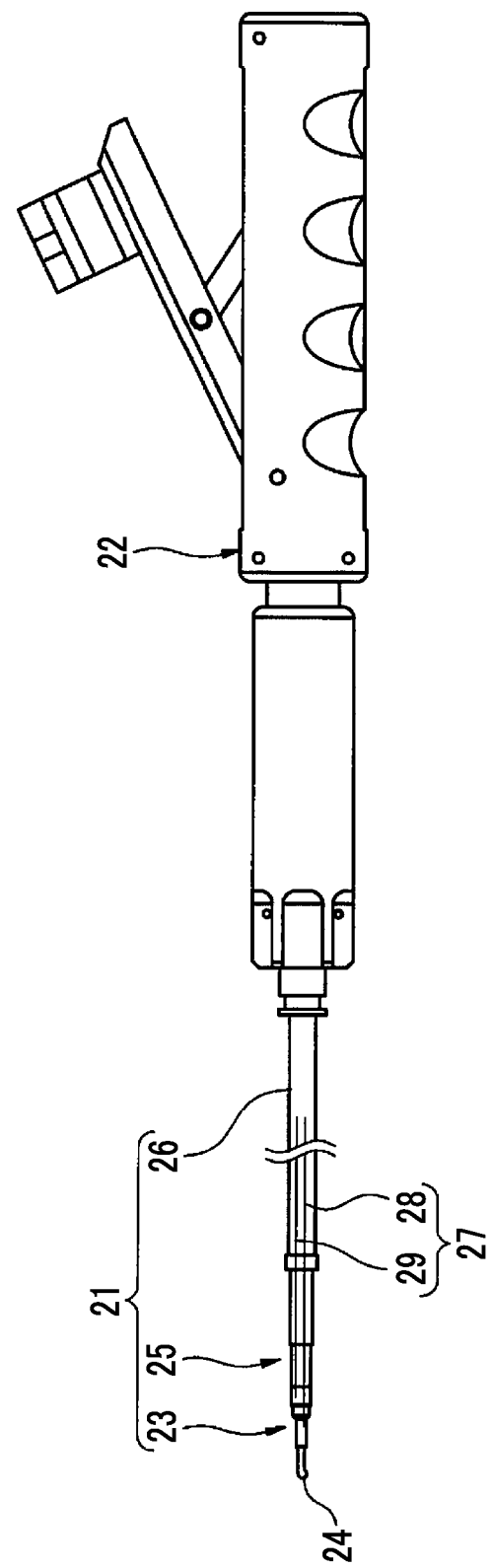
FIG. 2 is a view showing an example of a treatment tool for an endoscope, which is for describing Embodiment 1 of the present invention.

FIG. 2 shows an example of the treatment tool for an endoscope, which is for describing Embodiment 1 of the present invention.

A treatment tool for an endoscope 20 comprises an insertion part 21 that can be inserted into the first treatment tool channel 14 (see FIG. 1) and an operating part 22. The insertion part 21 has a distal end part 23 at which an openable and closable grip part 24 is provided, a bendable part 25 that is provided adjacent to an operating part side of the distal end part 23 and is bendable, and a soft portion 26 that connects the bendable part 25 to the operating part 22.

In a case where the insertion part 21 is inserted in the first treatment tool channel 14, the distal end part 23 and the bendable part 25 protrude from the edge surface of the endoscope distal end part 10 (see FIG. 1), and the soft portion 26 is accommodated in the first treatment tool channel 14. Similar to the endoscope soft portion 12, the soft portion 26 accommodated in the first treatment tool channel 14 is soft enough to be deformable along the shape of the insertion passage in the subject. The soft portion 26 can be configured, for example, such that an outer periphery of a screw pipe, which is formed by spirally winding a metal strip plate material, is covered with a mesh pipe formed by braiding a metal wire and an outer periphery of the mesh pipe is covered with a resin outer coat.

An operation of closing the grip part 24 (hereinafter, referred to as a closing operation) and an operation of bending the bendable part 25 (hereinafter, referred to as a bending operation) are input into the operating part 22. The treatment tool for an endoscope 20 further comprises a transmitting part 27 that transmits the operations of the operating part 22 to the grip part 24 and the bendable part 25. The transmitting part 27 has a first transmitting member 28 that extends from the grip part 24 toward the operating part 22 and a second transmitting member 29 that extends from the bendable part 25 toward the operating part 22. The first transmitting member 28 and the second transmitting member 29 are accommodated inside the soft portion 26. The closing operation input into the operating part 22 is transmitted to the grip part 24 via the first transmitting member 28, and the bending operation input into the operating part 22 is transmitted to the bendable part 25 via the second transmitting member 29.

Figure 3:
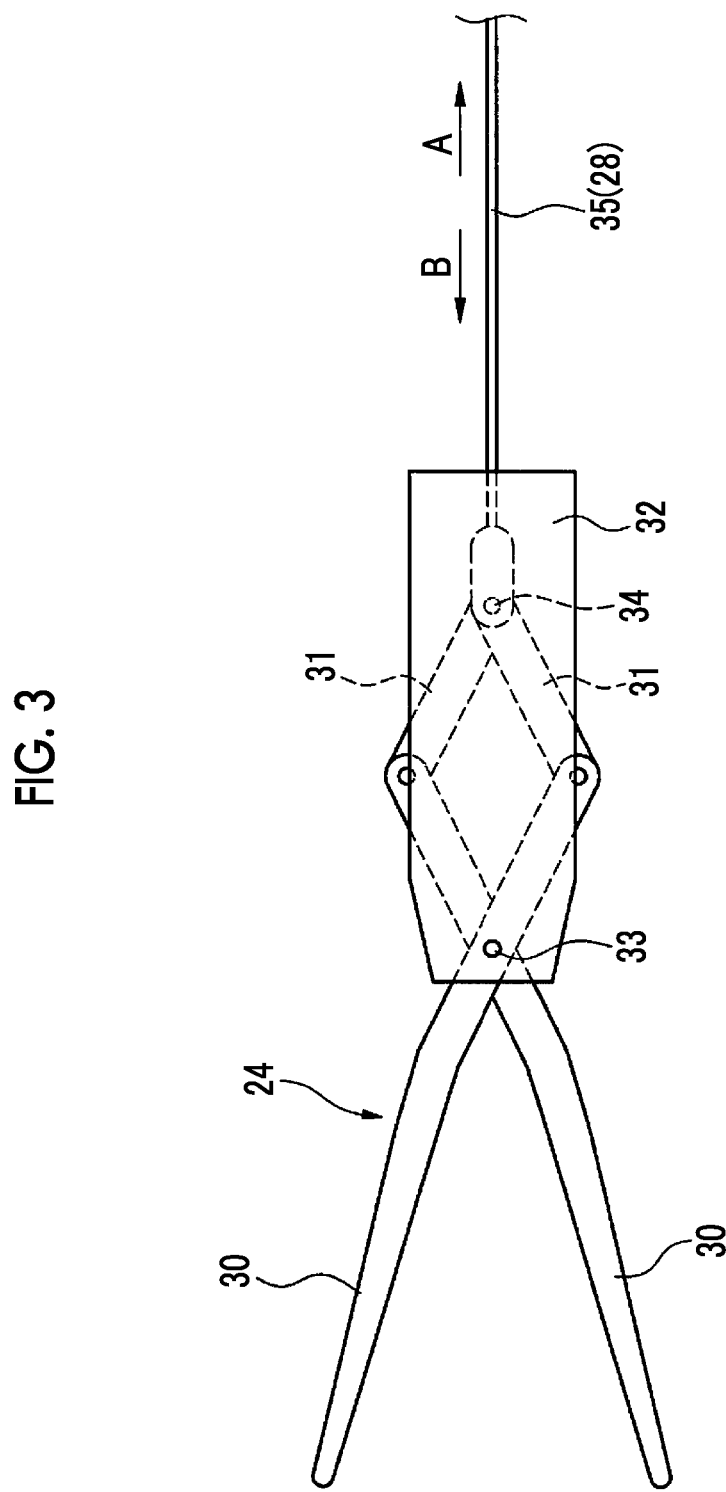
FIG. 3 is a view showing a grip part of the treatment tool for an endoscope of FIG. 2.
Figure 4:
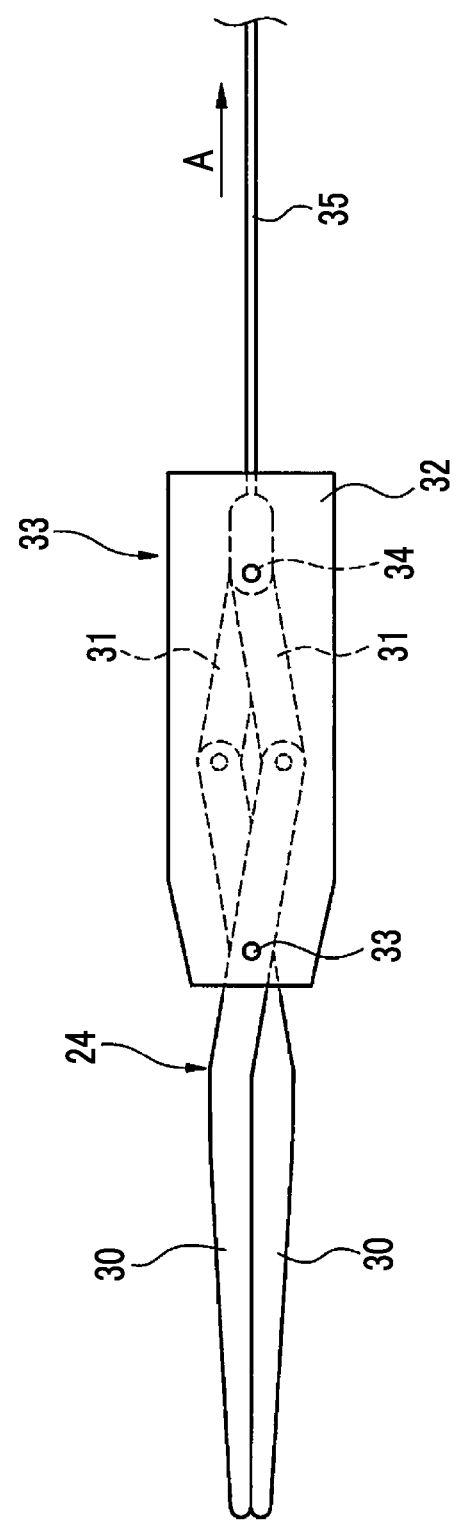
FIG. 4 is a view showing an operation of the grip part of FIG. 3.

FIGS. 3 and 4 show the grip part 24.

The grip part 24 has a pair of grip claws 30, a pair of link members 31, and a support 32 that supports the pair of grip claws 30 so as to be movable rotationally. The pair of grip claws 30 are disposed to intersect each other, and a pin 33 is provided to penetrate an intersecting portion of the pair of grip claws 30. The pair of grip claws 30 are movable rotationally about the pin 33 which is a rotational movement shaft, and the pin 33 is fixed to the support 32.

A distal end part of each of the pair of link members 31 is connected to a proximal end part of each of the pair of grip claws 30 so as to be movable rotationally. A proximal end part of each of the pair of link members 31 is disposed to intersect each other, and a pin 34 is provided to penetrate an intersecting portion of the pair of link members 31. The pair of link members 31 are movable rotationally about the pin 34 which is a rotational movement shaft, and the pin 34 is movable to increase or decrease a distance to the pin 33 instead of being fixed to the support 32.

As the first transmitting member 28 that transmits an operation of the operating part 22 to the grip part 24, one wire 35 is used in the present example, and a distal end part of the wire 35 is connected to the pin 34. The wire 35 is pulled to an operating part 22 side based on the operation of the operating part 22. Herein, as for movement of the wire 35, pulling to the operating part 22 side is defined as a movement in an A-direction, and pushing out to a distal end part 23 side is defined as a movement in a B-direction.

FIG. 3 shows a state where the wire 35 is pushed out to the distal end part 23 side, and the distal end parts of the pair of grip claws 30 are open. By moving the wire 35 in the A-direction (first direction) based on an operation of the operating part 22, the distal end parts of the pair of grip claws 30 are closed as shown in FIG. 4. On the other hand, by moving the wire 35 in the B-direction (second direction) in a state where the distal end parts of the pair of grip claws 30 are closed, the distal end parts of the pair of grip claws 30 are opened.

The wire 35 is an example of the first transmitting member 28, and the first transmitting member 28 may be an object that has flexibility, which does not hinder the bending of the bendable part 25 and the deformation of the soft portion 26, and can transmit a force in the A-direction and the B-direction, and may be, for example, a coil spring. In addition, the first transmitting member 28 may be a tube that is filled with a working fluid therein and is provided with a piston at the distal end part thereof.

Figure 5:
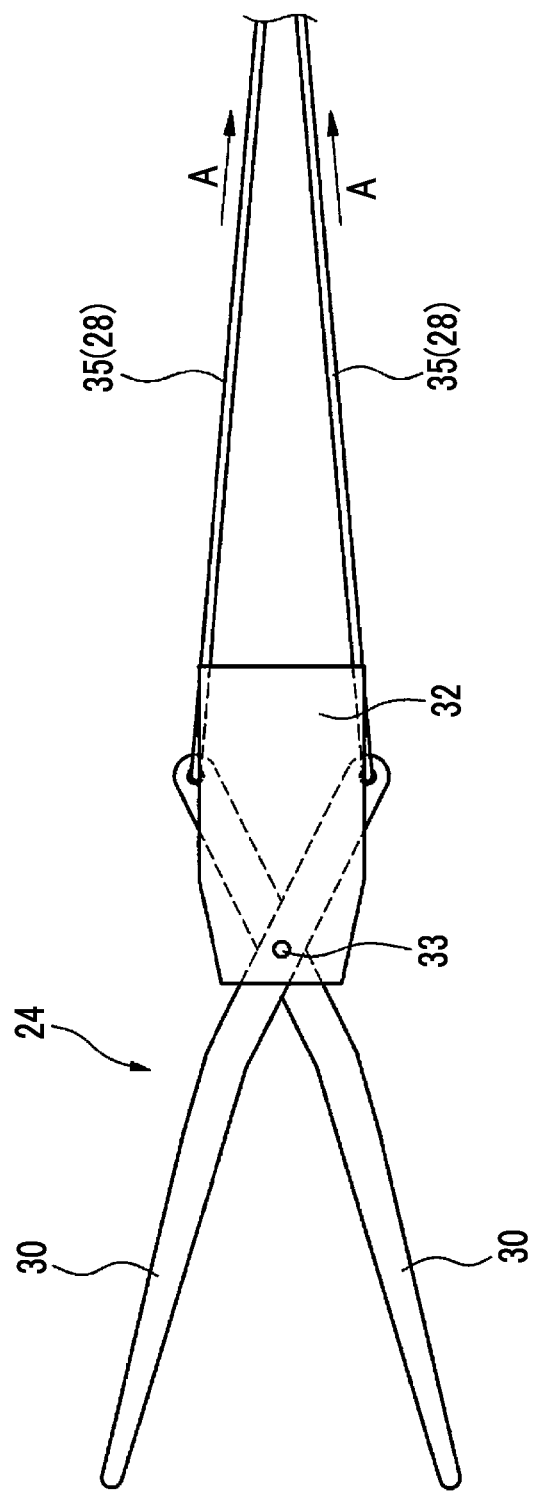
FIG. 5 is a view showing a modification example of the grip part of FIG. 3.

FIG. 5 shows another example of the grip part 24. Two wires 35 are used as the first transmitting member 28, and the wires 35 are connected to the proximal end parts of the pair of grip claws 30, respectively. By moving the two wires 35 in the A-direction, the distal end parts of the pair of grip claws 30 are closed. In the example shown in FIG. 5, the pair of link members 31 are unnecessary, and the length of the distal end part 23 can be reduced. Instead of the two wires 35, a single wire of which a distal end side is branched into two may be used, which is advantageous in reducing the diameters of the bendable part 25 and the soft portion 26.

Figure 6:
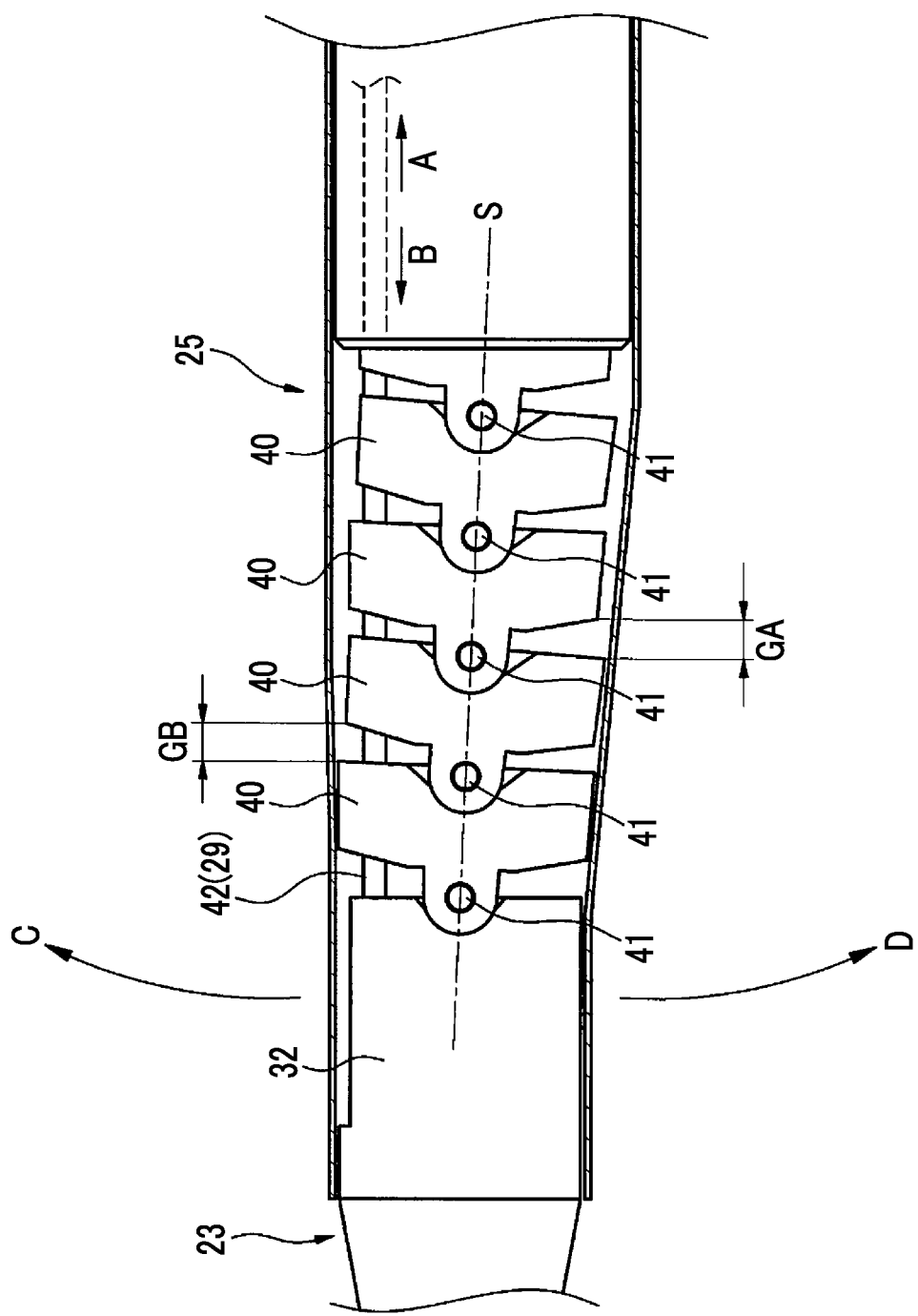
FIG. 6 is a view showing a bendable part of the treatment tool for an endoscope of FIG. 2.
Figure 7:
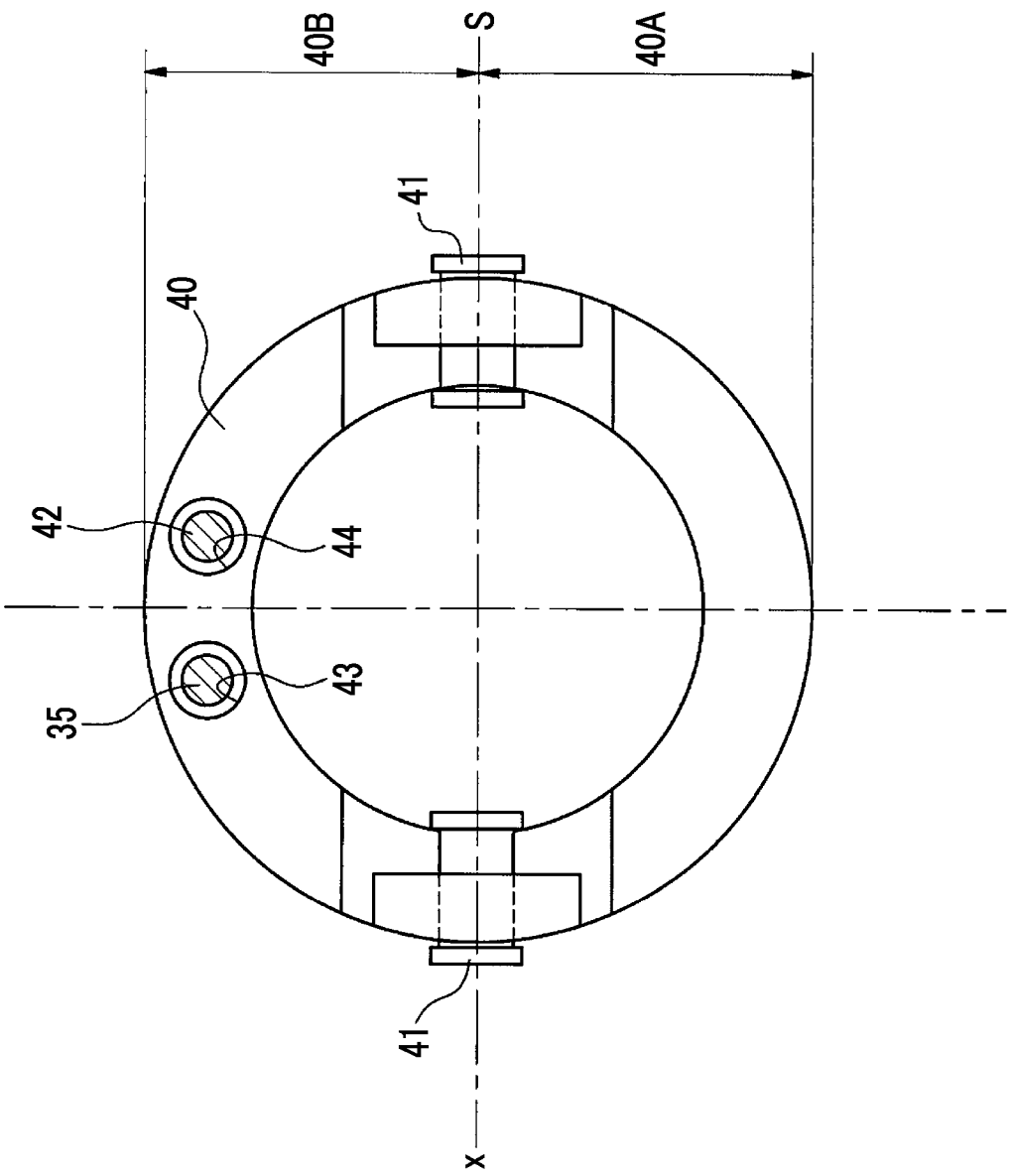
FIG. 7 is a view showing a cross section of the bendable part of FIG. 6.
Figure 8:
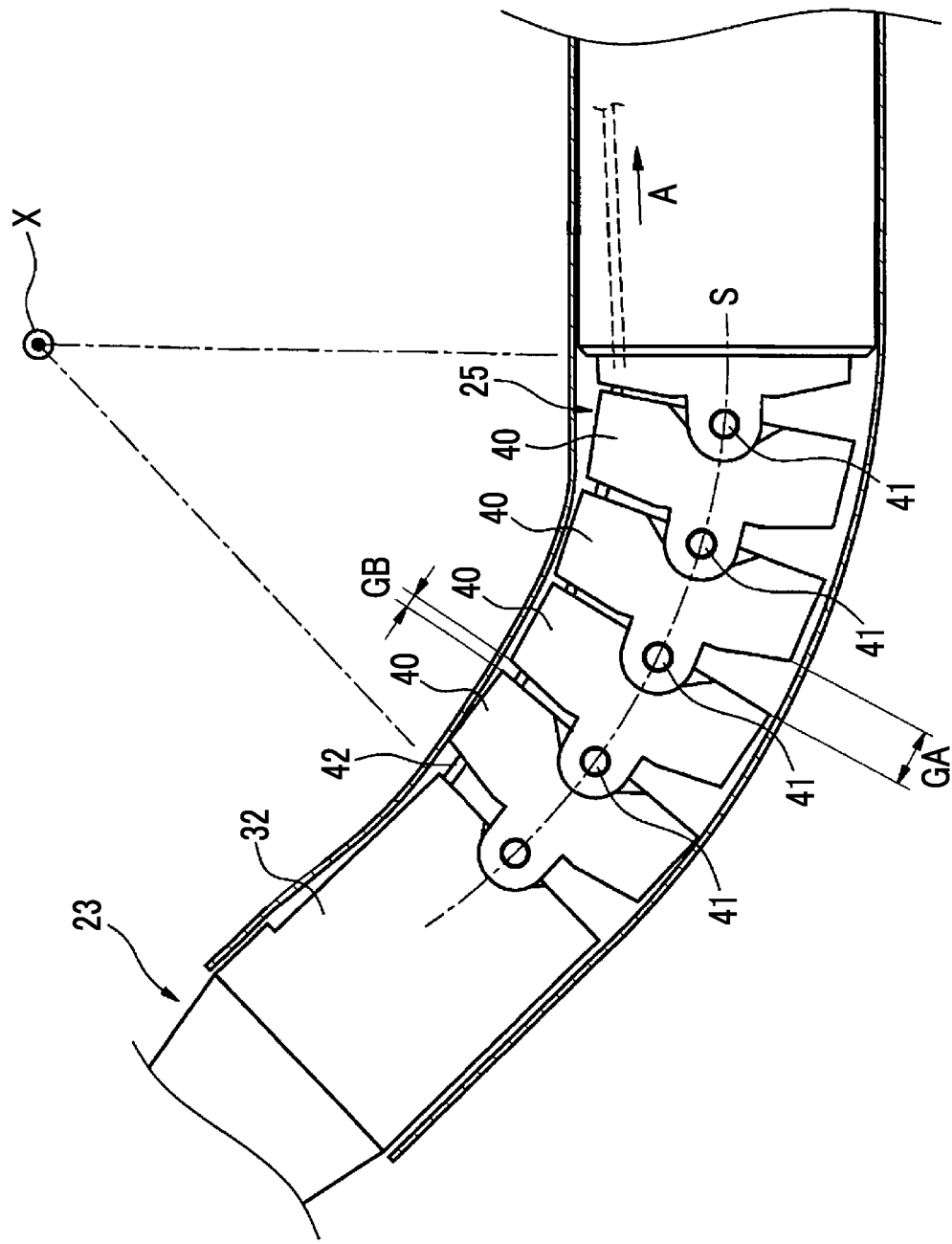
FIG. 8 is a view showing an operation of the bendable part of FIG. 6.

FIGS. 6 to 8 show the bendable part 25.

The bendable part 25 has a plurality of cyclic members 40 arranged in an axial direction of the insertion part 21, and two cyclic members 40, which are adjacent to each other, are connected to each other by a pair of pins 41. The two cyclic members 40 connected to each other by the pair of pins 41 are movable rotationally with respect to each other about a rotational movement shaft x passing through the pair of pins 41. The bending of the bendable part 25 is the sum of the rotational movements of the plurality of cyclic members 40. A bending central axis X for the bending of the bendable part 25 is parallel to the rotational movement shaft x, and is parallel to an opening and closing direction of the pair of grip claws 30.

A plane of which a length along a central axis of the insertion part 21 is constant regardless of the bending of the bendable part 25 is defined as a bent neutral plane, and a bent neutral plane S of the bendable part 25 passes through the plurality of pins 41 arranged in the axial direction of the insertion part 21. In a case where the cyclic member 40 is divided into a first portion 40A and a second portion 40B with the bent neutral plane S as a boundary, there is a gap GA between the first portions 40A of the two cyclic members 40 adjacent to each other, and there is a gap GB also between the second portions 40B. Therefore, the bendable part 25 is bendable in a C-direction in which the gap GB on a second portion 40B side is narrowed, and is bendable also in a D-direction in which the gap GA on a first portion 40A side is narrowed.

The bendable part 25 is bendable in both directions including the C-direction and the D-direction, but is bent in the C-direction based on an operation of the operating part 22. As the second transmitting member 29 that transmits the operation of the operating part 22 to the bendable part 25, a wire 42 is used in the present example, and a distal end part of the wire 42 is fixed to the support 32 of the distal end part 23. The wire 42 is pulled to the operating part 22 side based on the operation of the operating part 22. Herein, as for movement of the wire 42, pulling to the operating part 22 side is defined as a movement in the A-direction, and pushing out to the distal end part 23 side is defined as a movement in the B-direction.

In the bending of the bendable part 25 in the C-direction, the first portion 40A of the cyclic member 40 is positioned on a bent outer diameter side, and the second portion 40B is positioned on a bent inner diameter side. In the second portion 40B positioned on the bent inner diameter side, a first guide 43 and a second guide 44 are provided. The first guide 43 and the second guide 44 each are a hole that penetrates the second portion 40B in the axial direction of the insertion part 21, the wire 35 is inserted in the first guide 43, and the wire 42 is inserted in the second guide 44. The wire 35 inserted in the first guide 43 and the wire 42 inserted in the second guide 44 are disposed on the bent inner diameter side in the bending of the bendable part 25 in the C-direction. The first guide 43 and the second guide 44 are not limited to the holes insofar as the wire 35 and the wire 42 can be held so as to be able to be pushed and pulled in the axial direction of the insertion part 21.

As the wire 42 is moved in the A-direction (first direction) based on an operation of the operating part 22, the gap GB on the second portion 40B side, which is between the two cyclic members 40 adjacent to each other, is narrowed, and the bendable part 25 is bent in the C-direction. On the other hand, as the wire 42 is moved in the B-direction (second direction) in a state where the bendable part 25 is bent in the C-direction, the bendable part 25 is extended in a linear shape.

The wire 42 is an example of the second transmitting member 29, and the second transmitting member 29 may be an object that has flexibility, which does not hinder the bending of the bendable part 25 and the deformation of the soft portion 26, and can transmit a force in the A-direction and the B-direction, and may be, for example, a coil spring. In addition, the second transmitting member 29 may be a tube that is filled with a working fluid therein and is provided with a piston at the distal end part thereof.

Figure 9:
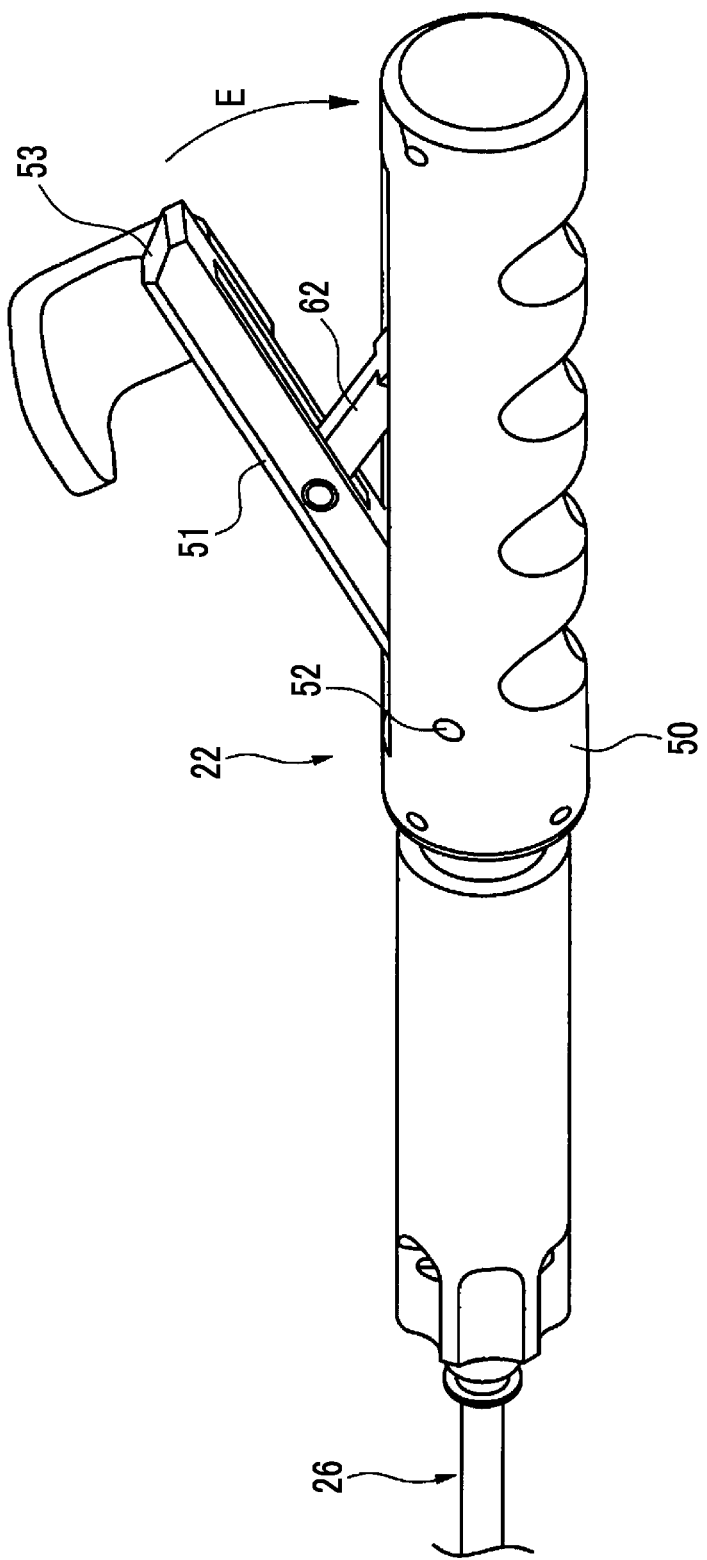
FIG. 9 is a view showing an operating part of the treatment tool for an endoscope of FIG. 2.

FIG. 9 shows the operating part 22.

The operating part 22 has an operating part body 50 and an operating handle 51. The operating part body 50 is formed in a cylindrical shape, and the soft portion 26 is connected to a distal end part of the operating part body 50 on one side in the axial direction.

The operating handle 51 is swingable about a pin 52 which is a swing shaft, and the pin 52 is supported by the operating part body 50. The operating handle 51 extends from the pin 52 toward a proximal end part side of the operating part body 50 while being inclined with respect to a central axis of the operating part body 50, and a free end part 53 of the operating handle 51 is spaced apart from the operating part body 50. The operating handle 51 is operated in an E-direction in which the free end part 53 approaches the operating part body 50.

In response to an operation of the operating handle 51 in the E-direction, the wire 35 which is the first transmitting member 28 of the transmitting part 27 is moved in the A-direction, and the grip part 24 is closed as described above. In addition, in response to the operation of the operating handle 51 in the E-direction, the wire 42 which is the second transmitting member 29 of the transmitting part 27 is also moved in the A-direction, and the bendable part 25 is bent as described above.

Figure 10:
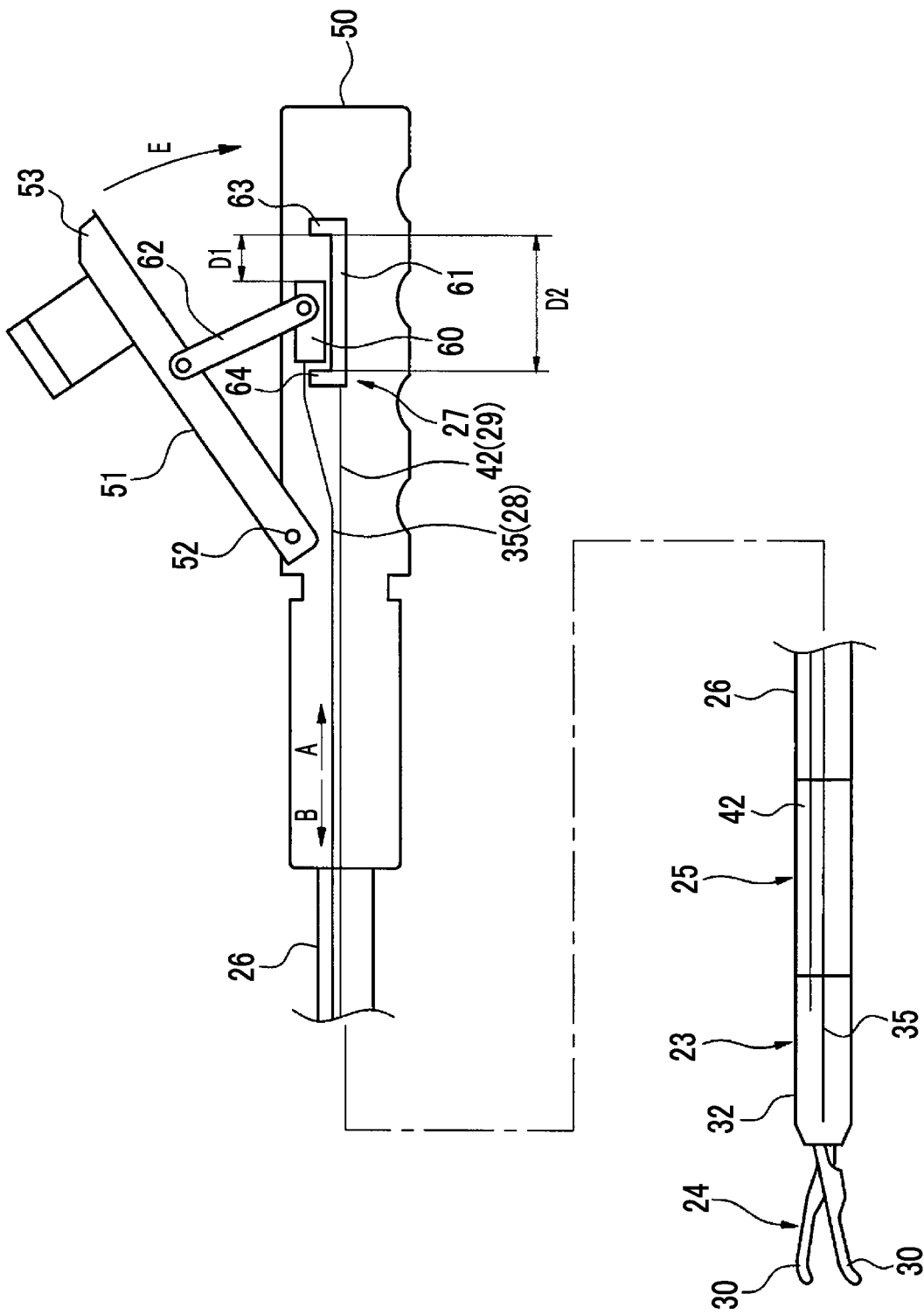
FIG. 10 is a view showing a transmitting part of the treatment tool for an endoscope of FIG. 2.
Figure 11:
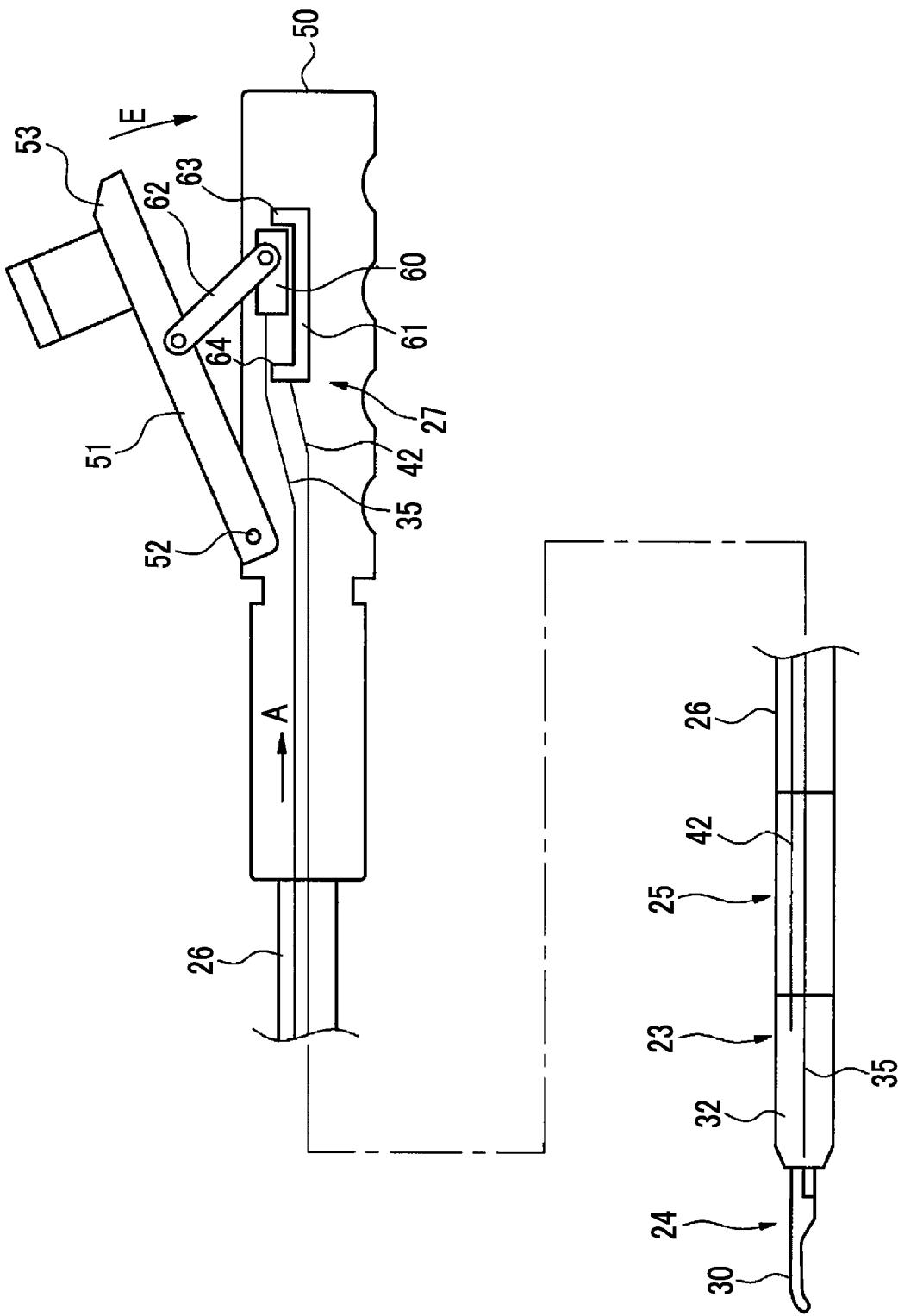
FIG. 11 is a view showing an operation of the transmitting part of FIG. 10.
Figure 12:
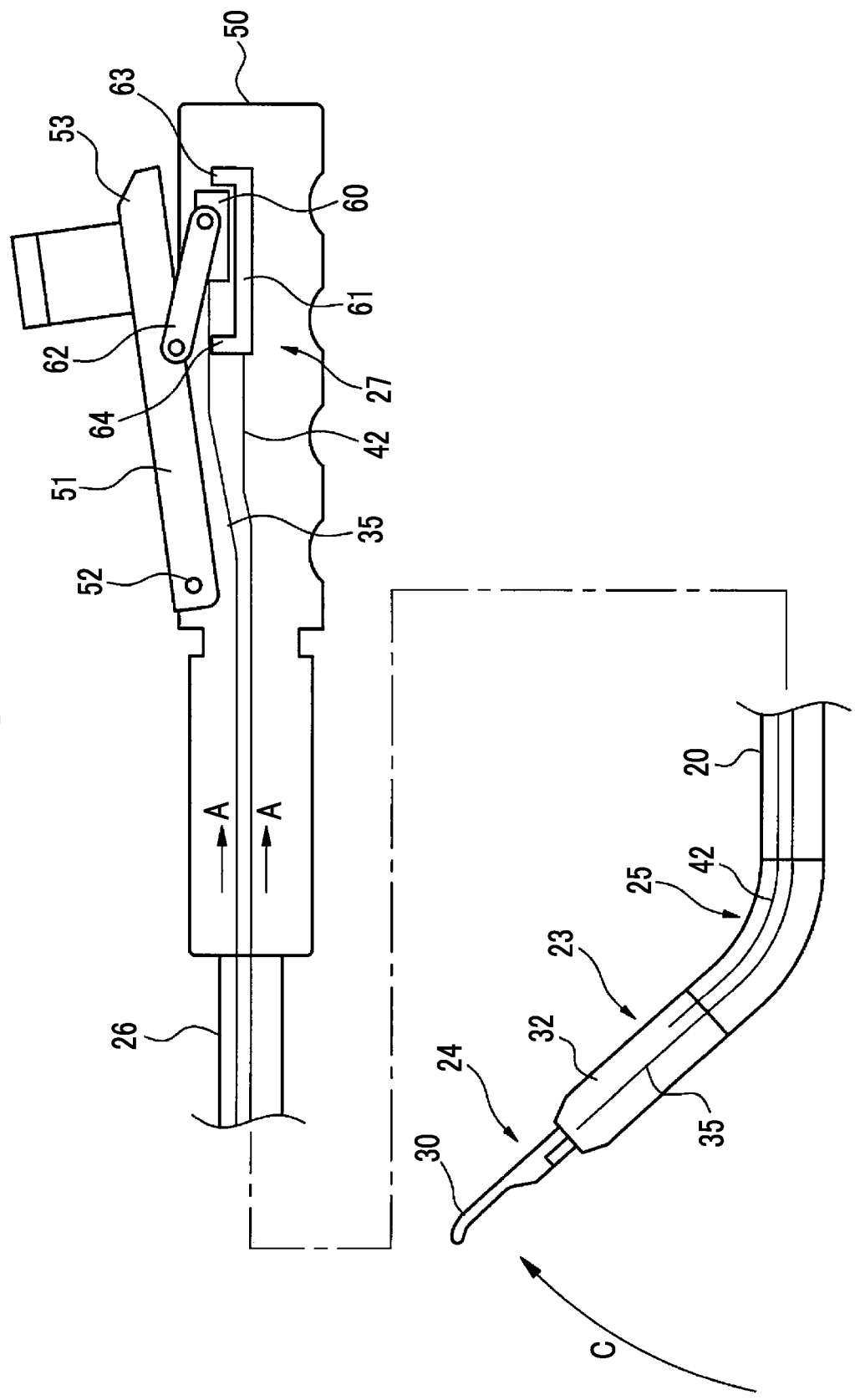
FIG. 12 is a view showing the operation of the transmitting part of FIG. 10.

FIGS. 10 to 12 show the transmitting part 27.

The transmitting part 27 has a first slider 60 which is a first movable body and a second slider 61 which is a second movable body. The first slider 60 and the second slider 61 are provided inside the operating part body 50, and are movable in an axial direction of the operating part body 50. The wire 35 which is the first transmitting member 28 and the wire 42 which is the second transmitting member 29 are introduced into the operating part body 50, the wire 35 is connected to the first slider 60, and the wire 42 is connected to the second slider 61.

The operating handle 51 and the first slider 60 are connected to each other by a link member 62. In response to an operation of the operating handle 51 in the E-direction, the first slider 60 is moved to the proximal end part side of the operating part body 50. Accordingly, the wire 35 connected to the first slider 60 is pulled to the operating part 22 side, that is, is moved in the A-direction. Since the first slider 60 and the wire 35 are integrated with each other, it can be said that the first slider 60 is also moved in the A-direction.

The second slider 61 has a first abutting part 63, and the first abutting part 63 is disposed on an A-direction side (the proximal end part side of the operating part body 50) of the first slider 60. In response to an operation of the operating handle 51 in the E-direction, the first slider 60 moved in the A-direction abuts against the first abutting part 63, and the second slider 61 is moved in the A-direction integrally with the first slider 60. Accordingly, the wire 42 connected to the second slider 61 is moved in the A-direction. However, the second slider 61 is moved after the start of the movement of the first slider 60.

FIG. 10 shows an unoperated state of the operating handle 51, and the free end part 53 of the operating handle 51 is spaced apart from the operating part body 50. In this case, the grip part 24 is open, and the bendable part 25 extends in a linear shape. In a case where the operating handle 51 is not operated, an interval D1 is placed between the first slider 60 and the first abutting part 63, and a stroke of the first slider 60 with respect to an operation of the operating handle 51 in the E-direction is larger than the interval D1.

As shown in FIG. 11, in response to an operation of the operating handle 51 in the E-direction, first, the first slider 60 is moved independently in the A-direction by the interval D1. Accordingly, the wire 35 is moved in the A-direction by the interval D1, and the grip part 24 is closed. On the other hand, the second slider 61 and the wire 42 are not moved, and the bendable part 25 is maintained in a linear shape.

Next, as shown in FIG. 12, in response to a further operation of the operating handle 51 in the E-direction, the first slider 60 and the second slider 61 are moved integrally with each other in the A-direction. Accordingly, the wire 42 is moved in the A-direction, and the bendable part 25 is bent. The grip part 24 is maintained in a closed state.

As the operating handle 51 is operated in an opposite direction to the E-direction and returns to the unoperated state as shown in FIG. 10, the first slider 60 connected to the operating handle 51 is moved in the B-direction which is opposite to the A-direction. Accordingly, the wire 35 connected to the first slider 60 is also moved in the B-direction, and the grip part 24 is opened. Similarly, as the second slider 61 and the wire 42 are moved in the B-direction, the bendable part 25 is restored to a linear shape.

In order to restore the bendable part 25 to a linear shape, the second slider 61 further has a second abutting part 64, and the second abutting part 64 is disposed on a B-direction side (a distal end part side of the operating part body 50) of the first slider 60. The first slider 60 is disposed between the first abutting part 63 and the second abutting part 64, and an interval D2 between the first abutting part 63 and the second abutting part 64 is smaller than the stroke of the first slider 60 with respect to an operation of the operating handle 51 in the E-direction.

Figure 13:
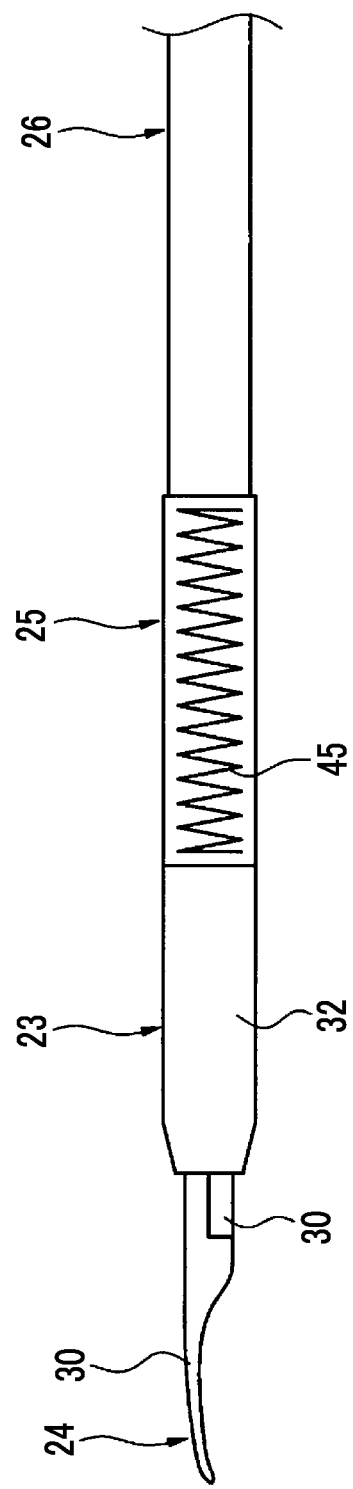
FIG. 13 is a view showing a modification example of the bendable part of the treatment tool for an endoscope of FIG. 2.

As the operating handle 51 returns to an unoperated state, the first slider 60 moved in the B-direction abuts against the second abutting part 64, and the second slider 61 is moved in the B-direction integrally with the first slider 60. Accordingly, the wire 42 connected to the second slider 61 is moved in the B-direction, and the bendable part 25 is restored to a linear shape. As shown in FIG. 13, in order to restore the bendable part 25 to a linear shape, an elastic member 45 such as a leaf spring and a coil spring may be provided in the bendable part 25.

Figure 14:
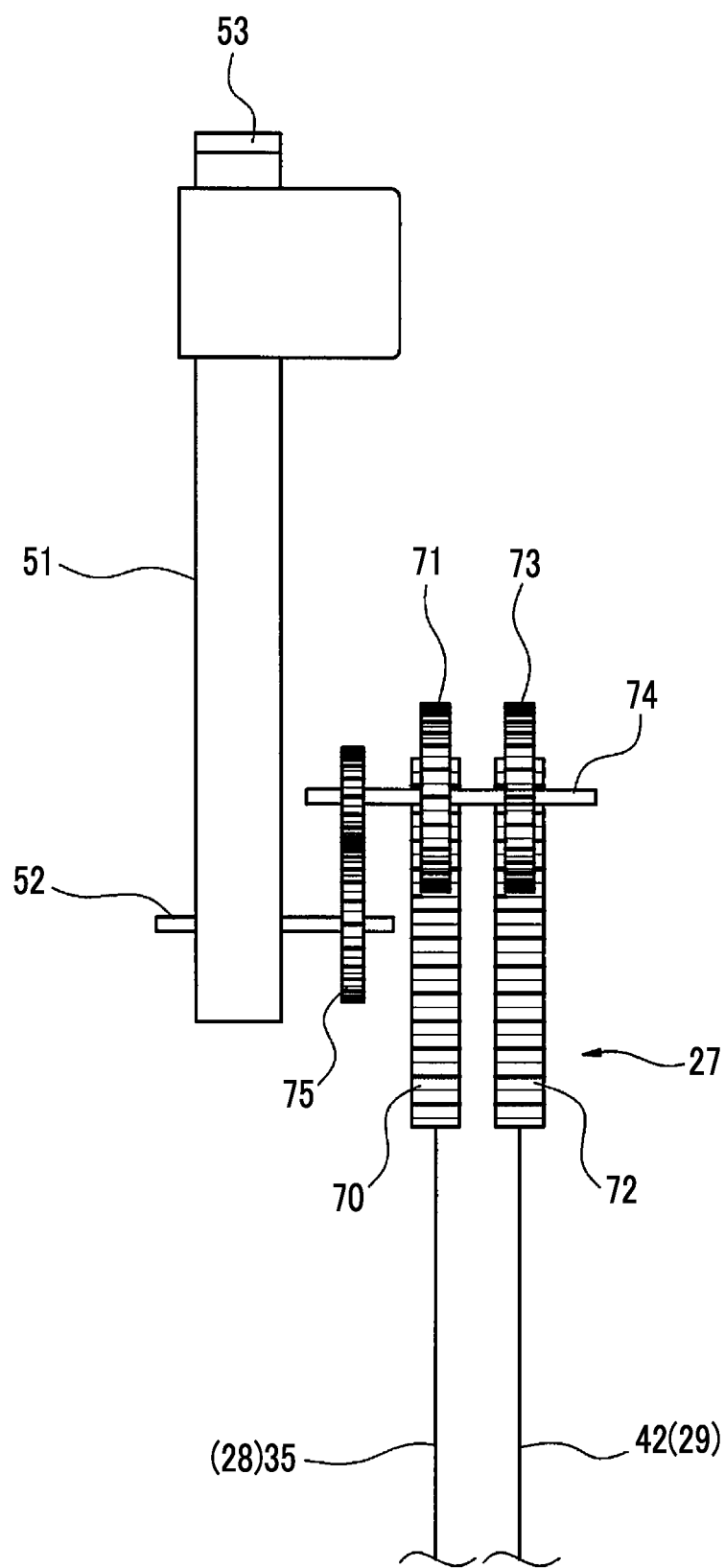
FIG. 14 is a view showing another example of the transmitting part of the treatment tool for an endoscope of FIG. 2.
Figure 15:
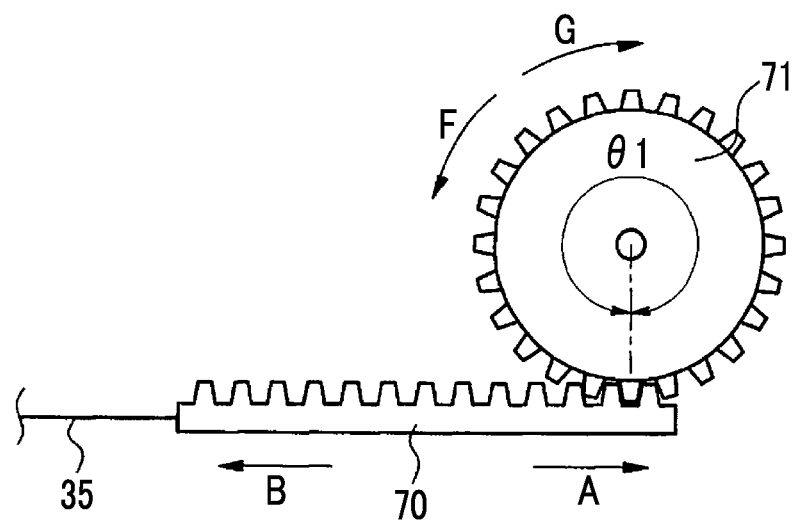
FIG. 15 is a view showing a first movable body of the transmitting part of FIG. 14.
Figure 16:
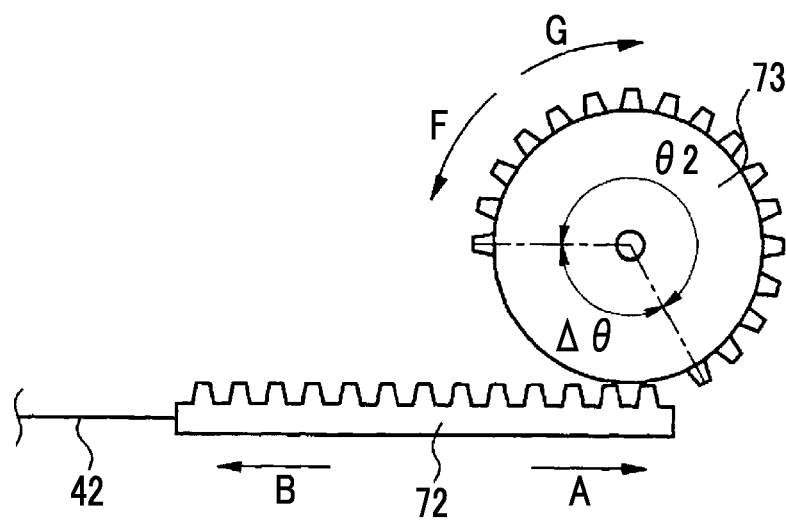
FIG. 16 is a view showing a second movable body of the transmitting part of FIG. 14.

FIGS. 14 to 16 show another example of the transmitting part 27.

The transmitting part 27 shown in FIGS. 14 to 16 has a first rack 70 that is a first movable body, a first pinion 71 that meshes with the first rack 70, a second rack 72 that is a second movable body, and a second pinion 73 that meshes with the second rack 72.

The first rack 70 and the second rack 72 are provided inside the operating part body 50, and are movable in the axial direction of the operating part body 50. The wire 35, which is the first transmitting member 28, is connected to the first rack 70, and the wire 42, which is the second transmitting member 29, is connected to the second rack 72. The first pinion 71 and the second pinion 73 are fixed to a shaft 74, and the shaft 74 is connected to the operating handle 51 via an appropriate gear device 75. The first pinion 71 and the second pinion 73 are rotated integrally with each other in an F-direction in response to an operation of the operating handle 51 in the E-direction.

In response to the rotation of the first pinion 71 in the F-direction, the first rack 70 is moved in the A-direction. Accordingly, the wire 35 connected to the first rack 70 is moved in the A-direction, and the grip part 24 is closed. In addition, in response to the rotation of the second pinion 73 in the F-direction, the second rack 72 is moved in the A-direction. Accordingly, the wire 42 connected to the second rack 72 is moved in the A-direction, and the bendable part 25 is bent. However, the second rack 72 is moved after the start of the movement of the first rack 70.

Teeth of the first pinion 71 are formed over the entire length of an outer periphery of the first pinion 71. On the contrary, teeth of the second pinion 73 are formed only on a part of an outer periphery of the second pinion 73. That is, a central angle $\theta 2$ of the second pinion 73 in a teeth formation range is smaller than a central angle $\theta 1$ of the first pinion 71 in a teeth formation range. In a case where the operating handle 51 is not operated, the second rack 72 and the second pinion 73 do not mesh with each other while the first rack 70 and the first pinion 71 mesh with each other.

In a case where a difference between the central angle $\theta 1$ of the first pinion 71 in the teeth formation range and the central angle $\theta 2$ of the second pinion 73 in the teeth formation range is defined as $\Delta \theta$ and the operating handle 51 is operated in the E-direction, the second rack 72 and the second pinion 73 mesh with each other after the second pinion 73 idles by $\Delta \theta$. Therefore, in response to an operation of the operating handle 51 in the E-direction, first, the first rack 70 is moved independently in the A-direction, and the grip part 24 is closed. Then, the second rack 72 is moved in the A-direction after the start of the movement of the first rack 70, and the bendable part 25 is bent.

As the operating handle 51 returns to an unoperated state, the first pinion 71 and the second pinion 73 are rotated in a G-direction opposite to the F-direction. The first rack 70 that meshes with the first pinion 71 and the second rack 72 that meshes with the second pinion 73 are moved in the B-direction opposite to the A-direction. Accordingly, the wire 35 connected to the first rack 70 is moved in the B-direction, and the grip part 24 is opened. In addition, the wire 42 connected to the second rack 72 is moved in the B-direction, and the bendable part 25 is restored to a linear shape.

In the example of the transmitting part 27 shown in FIGS. 10 to 12 and the example of the transmitting part 27 shown in FIGS. 14 to 16, the first movable body (the first slider 60 and the first rack 70) and the second movable body (the second slider 61 and the second rack 72) are provided at the operating part 22, but the first movable body and the second movable body may be provided at the soft portion 26.

Figure 17:
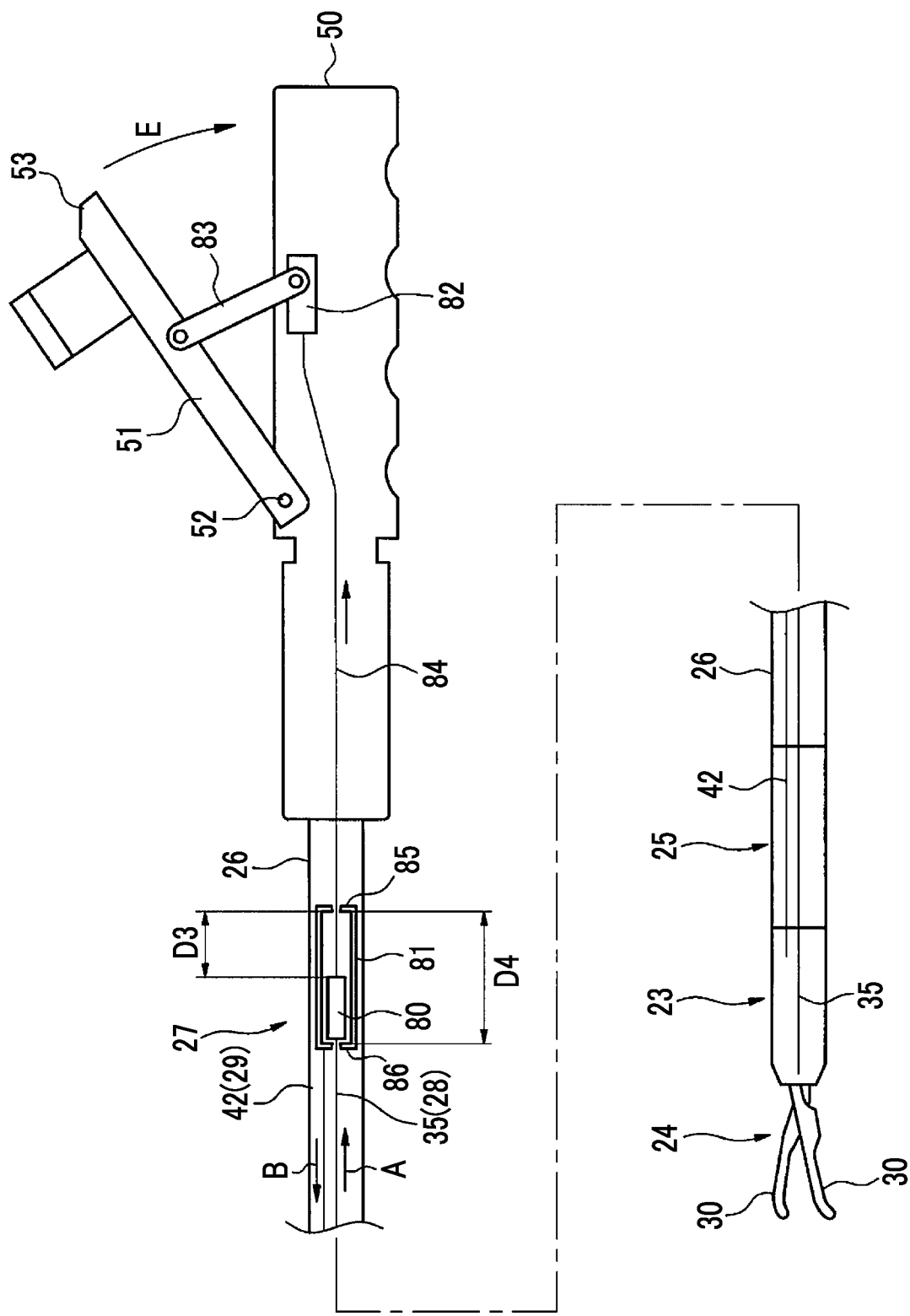
FIG. 17 is a view showing still another example of the transmitting part of the treatment tool for an endoscope of FIG. 2.

The transmitting part 27 shown in FIG. 17 has a first slider 80 which is a first movable body and a second slider 81 which is a second movable body. The first slider 80 and the second slider 81 are provided inside the soft portion 26, and are movable in an axial direction of the soft portion 26. The wire 35, which is the first transmitting member 28, is connected to the first slider 80, and the wire 42, which is the second transmitting member 29, is connected to the second slider 81.

The transmitting part 27 further has a third slider 82. The third slider 82 is provided inside the operating part body 50, and is movable in the axial direction of the operating part body 50. The operating handle 51 and the third slider 82 are connected to each other by a link member 83, and the third slider 82 is moved to the proximal end part side of the operating part body 50 in response to an operation of the operating handle 51 in the E-direction.

The first slider 80 and the third slider 82 are connected to each other by a connecting wire 84. In response to an operation of the operating handle 51 in the E-direction, the third slider 82 is moved to the proximal end part side pf the operating part body 50, and the first slider 80 is moved to the operating part 22 side via the connecting wire 84. Accordingly, the wire 35 connected to the first slider 80 is pulled to the operating part 22 side, that is, is moved in the A-direction.

The second slider 81 is formed in a tubular shape, and the first slider 80 is accommodated inside the second slider 81. The second slider 81 has a first abutting part 85 disposed on the A-direction side (operating part 22 side) of the first slider 80 and a second abutting part 86 disposed on the B-direction side (distal end part 23 side) of the first slider 80, and the first abutting part 85 and the second abutting part 86 configure lids at both ends of the tubular second slider 81 in the axial direction. The connecting wire 84 penetrates the first abutting part 85 and is connected to the first slider 80. The wire 35 penetrates the second abutting part 86 and is connected to the first slider 80.

In a case where the operating handle 51 is not operated, an interval D3 is placed between the first slider 80 and the first abutting part 85, and a stroke of the first slider 80 with respect to an operation of the operating handle 51 in the E-direction is larger than the interval D3. In addition, an interval D4 between the first abutting part 85 and the second abutting part 86 is smaller than the stroke of the first slider 80 with respect to the operation of the operating handle 51 in the E-direction.

In response to an operation of the operating handle 51 in the E-direction, first, the first slider 80 is moved independently in the A-direction by the interval D3, and the grip part 24 is closed. In response to a further operation of the operating handle 51 in the E-direction, the first slider 80 moved in the A-direction abuts against the first abutting part 85. Accordingly, the second slider 81 is moved in the A-direction after the start of the movement of the first slider 80, and the bendable part 25 is bent.

As the operating handle 51 returns to an unoperated state, the third slider 82 connected to the operating handle 51 and the first slider 80 connected to the third slider 82 via the connecting wire 84 are moved in the B-direction which is opposite to the A-direction. Accordingly, the wire 35 connected to the first slider 80 is also moved in the B-direction, and the grip part 24 is opened. In addition, the first slider 80 moved in the B-direction abuts against the second abutting part 86, and the second slider 81 is moved in the B-direction integrally with the first slider 80. Accordingly, the wire 42 connected to the second slider 81 is moved in the B-direction, and the bendable part 25 is restored to a linear shape.

The first slider 80 may be formed in a tubular shape, and the second slider 81 may be accommodated inside the first slider 80.

FIGS. 18 to 21 show a treatment method for ESD as an example of a treatment method using the treatment tool for an endoscope 20.

Figure 18:
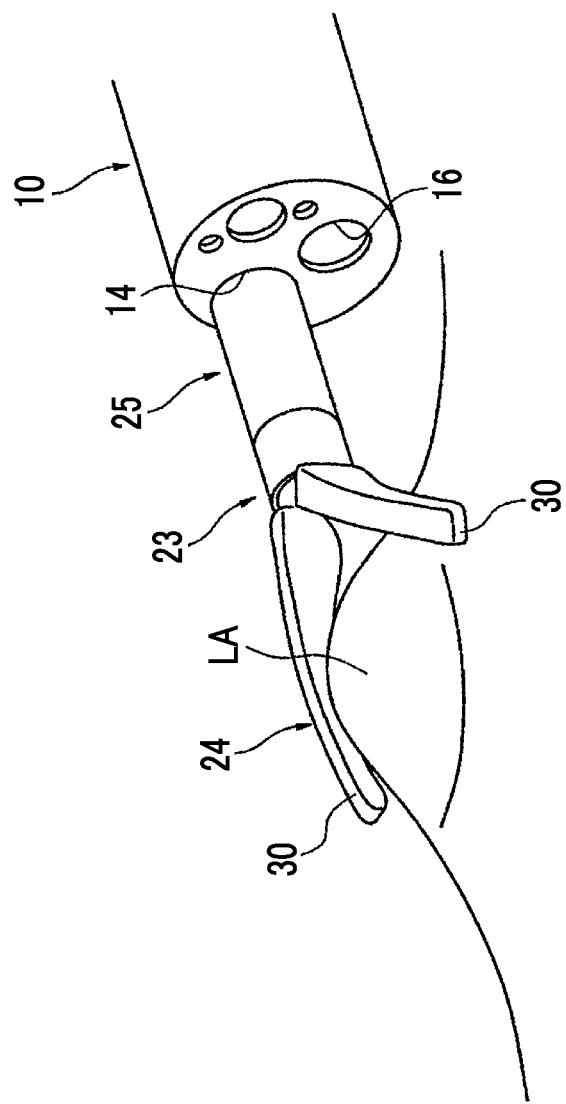
FIG. 18 is a view showing an example of a treatment method using a combination of the treatment tool for an endoscope of FIG. 2 and another endoscope treatment tool.

The endoscope 2 is inserted into the body, and the endoscope distal end part 10 is disposed at the side of a lesion part LA of a mucous membrane layer. The treatment tool for an endoscope 20 is inserted into the first treatment tool channel 14 of the endoscope 2, and the distal end part 23 and the bendable part 25 of the treatment tool for an endoscope 20 protrude from the edge surface of the endoscope distal end part 10 as shown in FIG. 18.

Figure 19:
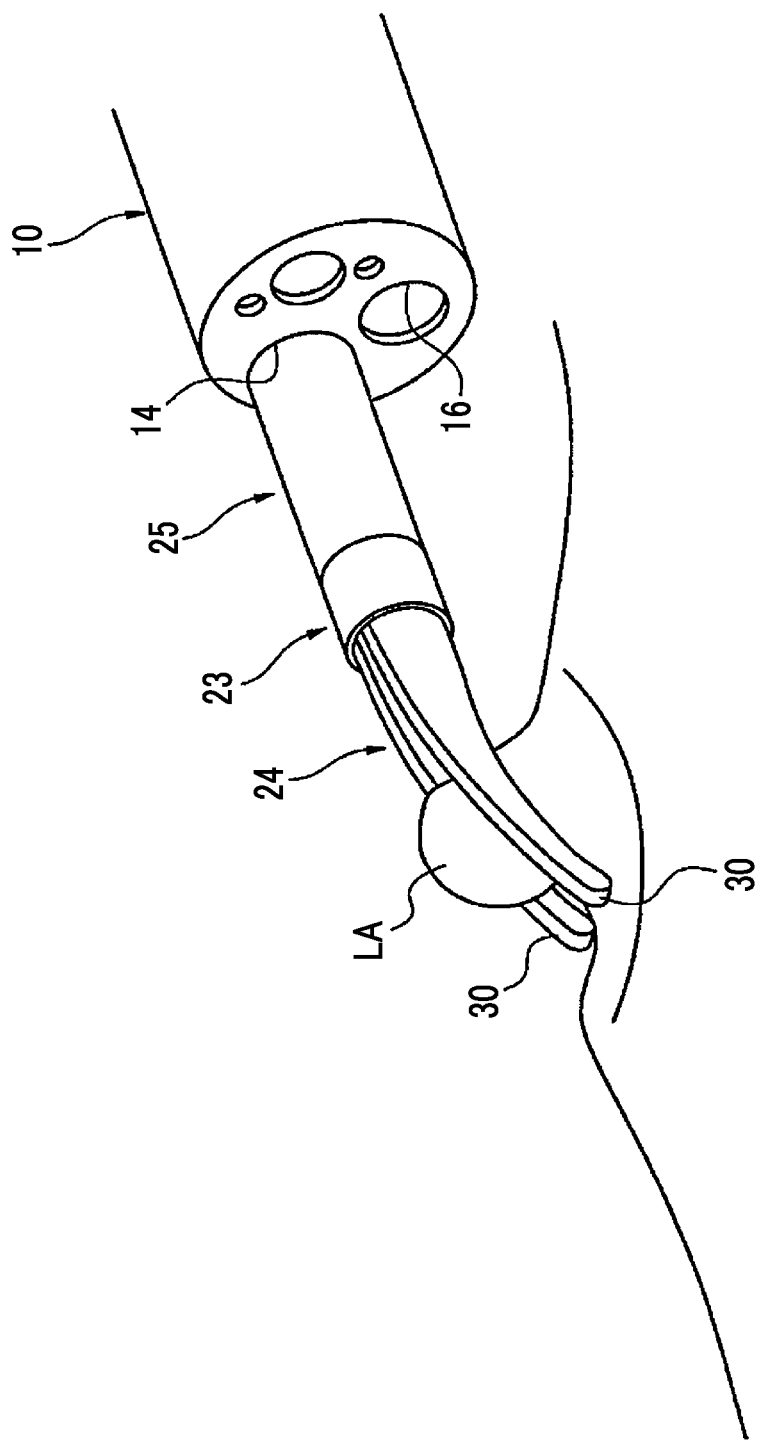
FIG. 19 is a view showing an example of the treatment method using the combination of the treatment tool for an endoscope of FIG. 2 and the other endoscope treatment tool.
Figure 20:
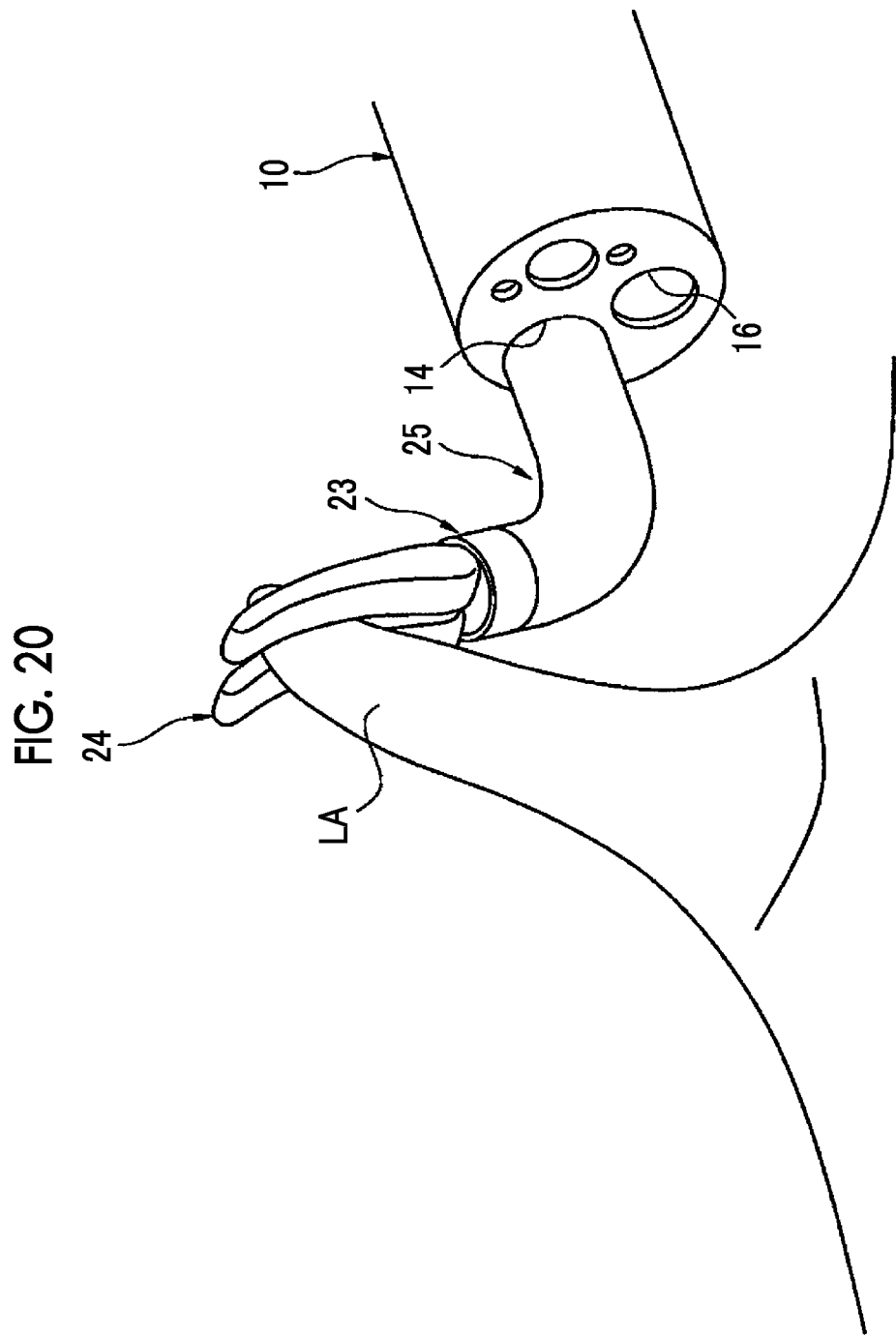
FIG. 20 is a view showing an example of the treatment method using the combination of the treatment tool for an endoscope of FIG. 2 and the other endoscope treatment tool.

Next, as shown in FIG. 19, the grip part 24 is closed based on an operation of the operating part 22, and the lesion part LA is gripped by the grip part 24. Then, after the lesion part LA is gripped by the grip part 24, the bendable part 25 is bent based on an operation of the operating part 22 as shown in FIG. 20. Accordingly, the grip part 24 is erected, and the lesion part LA gripped by the grip part 24 is lifted.

Figure 21:
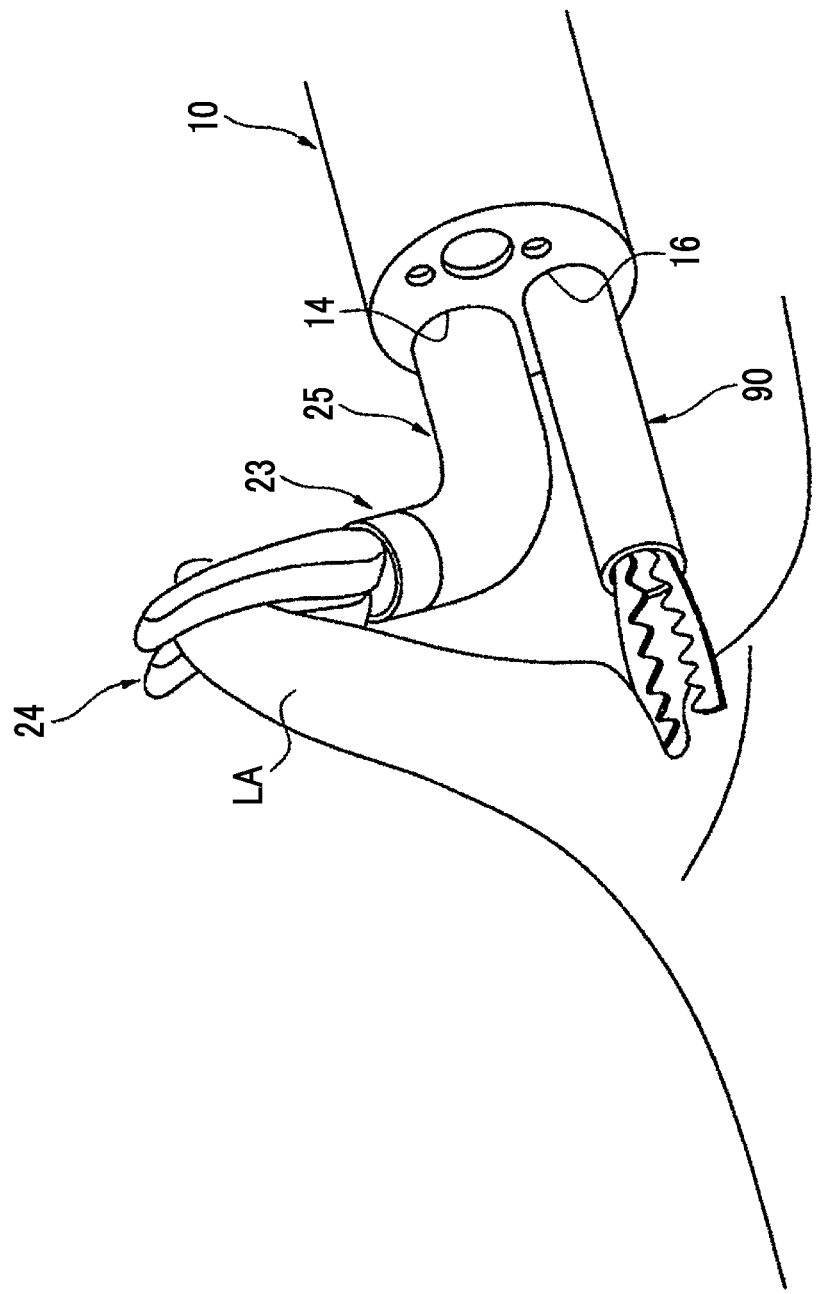
FIG. 21 is a view showing an example of the treatment method using the combination of the treatment tool for an endoscope of FIG. 2 and the other endoscope treatment tool.

In a state where the lesion part LA is being lifted, a high-frequency forcep 90 is inserted into the second treatment tool channel 16 of the endoscope 2, and the high-frequency forcep 90 protrudes from the edge surface of the endoscope distal end part 10 as shown in FIG. 21. Then, a lower part of the lesion part LA is incised by the high-frequency forcep 90.

The other endoscope treatment tool used in combination with the treatment tool for an endoscope 20 is selected as appropriate according to treatment, and is not limited to the high-frequency forcep 90. Examples of the other endoscope treatment tool include incision tools, such as high-frequency forceps and high-frequency knives, hemostatic tools, such as bipolar hemostatic forceps and clips, injection needles, and collection nets.

In the treatment method described above, the gripping of the lesion part LA by closing the grip part 24 and the lifting of the lesion part LA by bending the bendable part 25 are performed only by the operation of the operating part 22 as described above. Further, in a case where the grip part 24 is closed, the bendable part 25 is maintained in a linear shape, and a relative movement between the grip part 24 and the lesion part LA is prevented. Accordingly, the gripping of the lesion part LA and the lifting of the gripped lesion part LA can be easily performed with an operation of the treatment tool for an endoscope 20 alone.

In addition, based on an operation of the operating part 22, first, the wire 35 is moved in the A-direction, and the grip part 24 is closed. Then, after the grip part 24 is closed, the wire 42 is moved in the A-direction, and the bendable part 25 is bent in the C-direction. In this case, the wire 35 is also moved in the A-direction. Herein, since the wire 35 is disposed on the bent inner diameter side in the bending of the bendable part 25 in the C-direction and a length on the bent inner diameter side is reduced with the bending, the movement of the wire 35 in the A-direction is offset. Therefore, an increase in a gripping force of the grip part 24 is prevented, and the lesion part LA is not excessively compressed.

The wire 35 may be disposed on the bent outer diameter side in the bending of the bendable part 25 in the C-direction, or may be disposed on the bent neutral plane S of the bendable part 25.

The wire 35 for closing the grip part 24 is moved in the same A-direction as the wire 42, prior to the wire 42 for bending the bendable part 25 in the C-direction. In this case, friction can occur between the wire 35 and the bendable part 25. In a case where the wire 35 is disposed on the same bent inner diameter side of the bendable part 25 as the wire 42, there is a possibility that the bendable part 25 is bent in the C-direction due to the friction of the wire 35 and the grip part 24 which is closed to grip the lesion part LA is separated from the lesion part LA.

On the contrary, in a case where the wire 35 is disposed on the bent outer diameter side in the bending of the bendable part 25 in the C-direction, the grip part 24 is pressed against the lesion part LA as the bendable part 25 is bent in the D-direction opposite to the C-direction even though the bendable part 25 is bent due to the friction of the wire 35. In addition, in a case where the wire 35 is disposed on the bent neutral plane S of the bendable part 25, the bending of the bendable part 25 caused by the friction of the wire 35 is further prevented.

Further, the bendable part 25 may be configured to be not bendable in the D-direction. In this case, the bending of the bendable part 25 caused by the friction of the wire 35 is reliably prevented.

Figure 22:
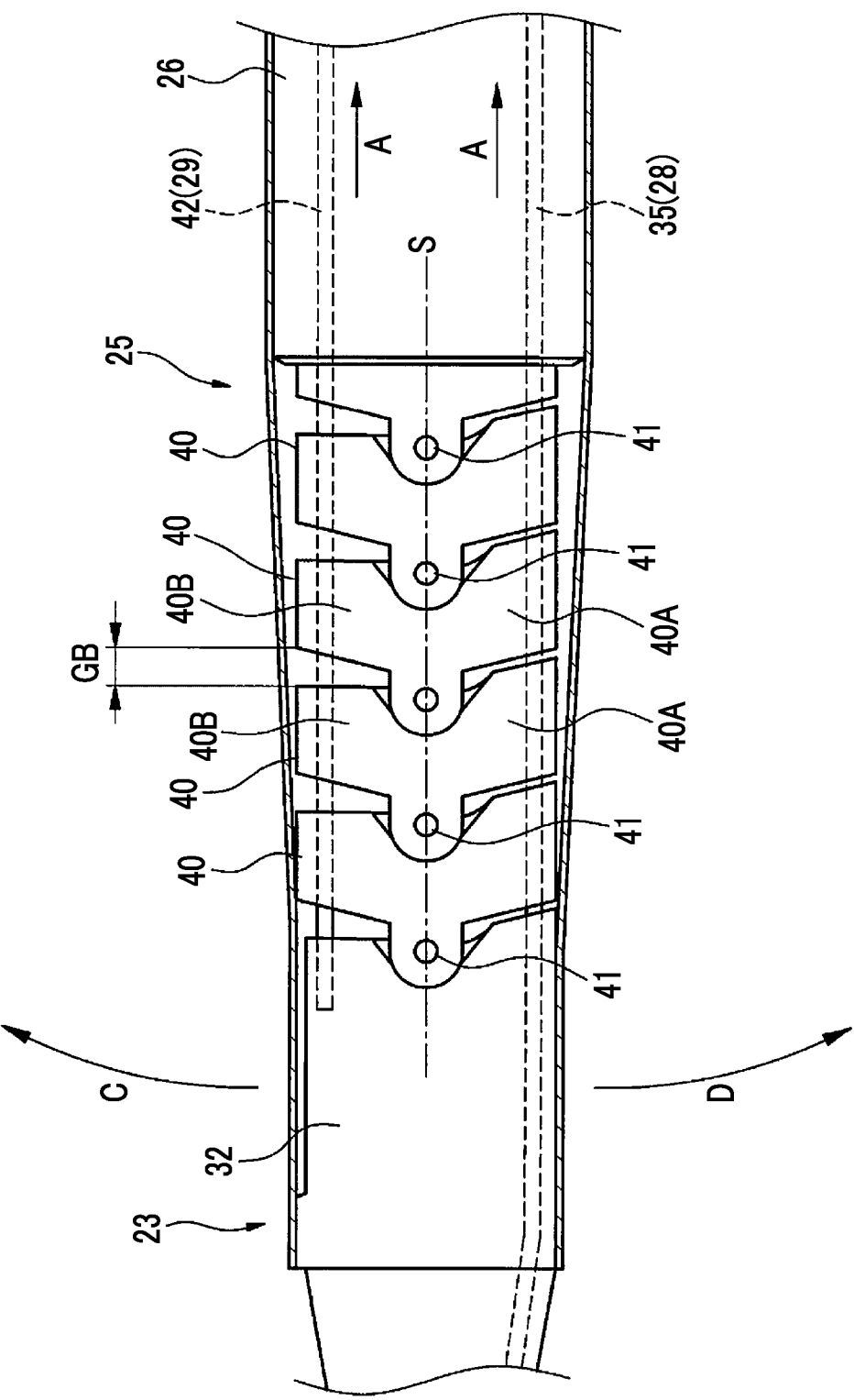
FIG. 22 is a view showing a modification example of the bendable part of FIG. 6.
Figure 23:
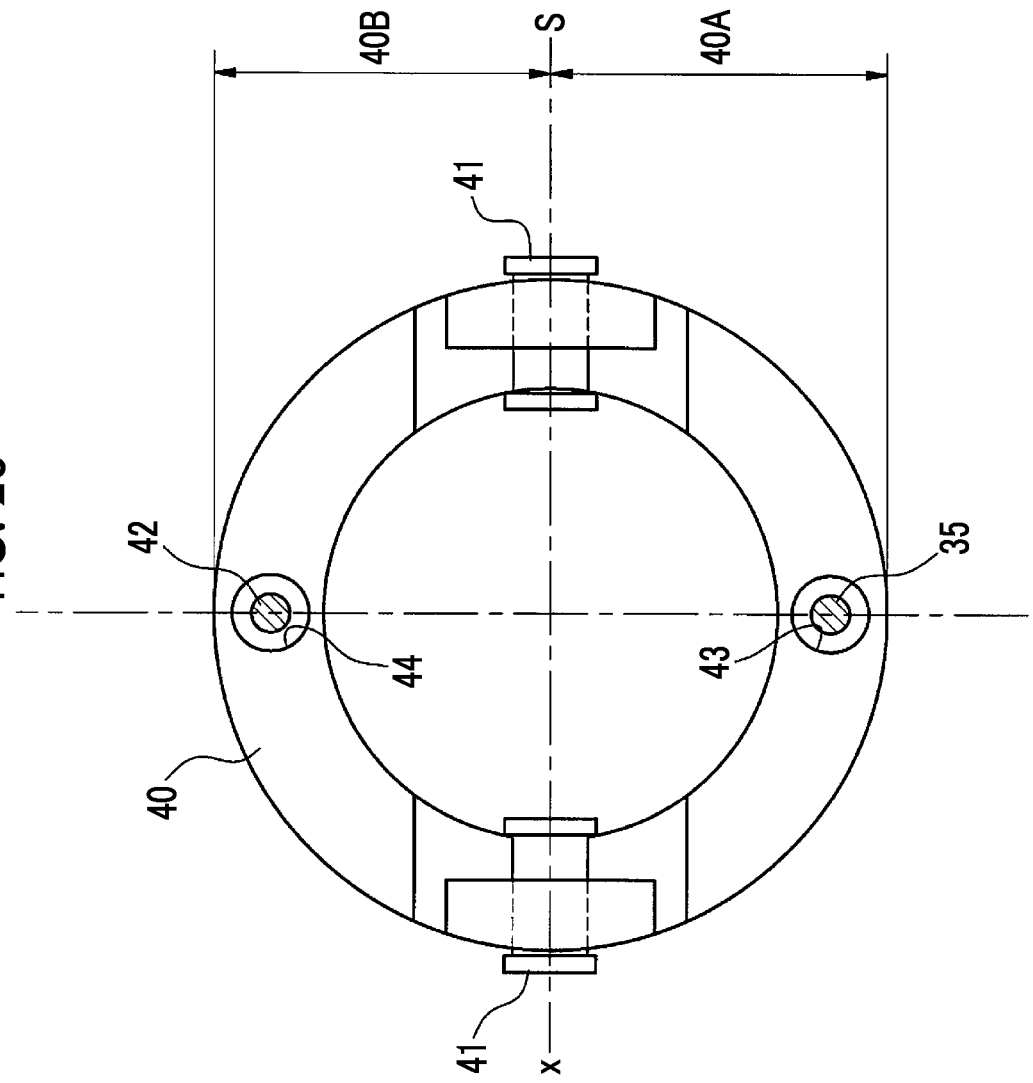
FIG. 23 is a view showing a cross section of the bendable part of FIG. 22.

In a case where the cyclic member 40 is divided into the first portion 40A and the second portion 40B with the bent neutral plane S of the bendable part 25 as a boundary in the bendable part 25 shown in FIGS. 22 and 23, the second portions 40B of the two cyclic members 40 adjacent to each other are contactless with the gap GB therebetween, but the first portions 40A are in contact with each other. Therefore, the bendable part 25 is bendable only in the C-direction, in which the gap GB is narrowed, and is not bendable in the D-direction opposite to the C-direction.

In the bending of the bendable part 25 in the C-direction, the first portion 40A of the cyclic member 40 is positioned on the bent outer diameter side, and the second portion 40B is positioned on the bent inner diameter side. The first guide 43 that holds the wire 35 which is the first transmitting member 28 is provided at the first portion 40A, and the wire 35 is disposed on the bent outer diameter side. The second guide 44 that holds the wire 42 which is the second transmitting member 29 is provided at the second portion 40B, and the wire 42 is disposed on the bent inner diameter side.

The gap GB is narrowed as the wire 42 is moved in the A-direction, and thus the bendable part 25 is bent in the C-direction. In a case where the wire 35 is disposed on the bent outer diameter side which is an opposite side to the wire 42 with the bent neutral plane S interposed therebetween and a bendable part 25 is bent due to the friction of the wire 35 moved in the A-direction, the bendable part 25 is bent in the C-direction opposite to the D-direction, but the bendable part 25 is not bendable in the D-direction. Therefore, based on an operation of the operating part 22, the wire 35 is moved in the A-direction prior to the wire 42, and in a case where the grip part 24 is closed, the bendable part 25 is reliably maintained in a linear shape. Accordingly, a relative movement between the grip part 24 and the lesion part LA gripped by the grip part 24 is prevented, and the gripping of the lesion part LA becomes even easier.

The wire 35 may be disposed on the bent neutral plane S. In a case where the wire 35 is disposed on the bent neutral plane S, the first guide 43 holding the wire 35 is provided, for example, at an end part of the pin 41.

Figure 24:
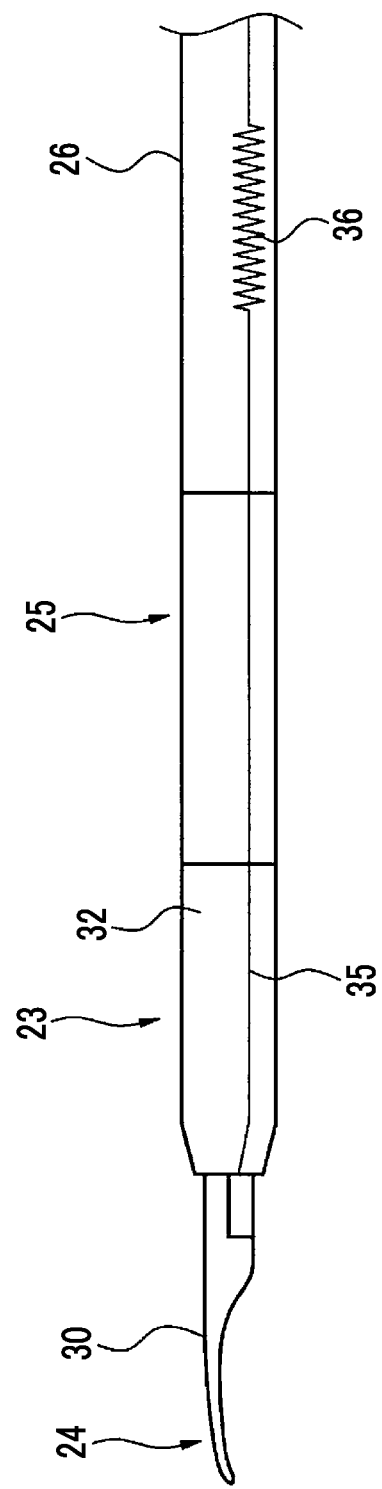
FIG. 24 is a view showing a modification example of a first transmitting member of the treatment tool for an endoscope of FIG. 2.

In a case where the wire 35 is disposed on the bent outer diameter side in the bending of the bendable part 25 in the C-direction or is disposed on the bent neutral plane S, a length on the bent outer diameter side is extended with the bending, and a length on the bent neutral plane S is constant regardless of the bending. Therefore, a movement of the wire 35 in the A-direction after the grip part 24 is closed is not offset by the reduction of the length of the wire 35 at a disposed place. For this reason, in response to the movement of the wire 35 in the A-direction after the grip part 24 is closed, the gripping force of the grip part 24 gradually increases. In a case where the lesion part LA is lifted, the lesion part LA can be more firmly gripped due to an increase in the gripping force of the grip part 24, but it is preferable that at least a part of the wire 35 in a longitudinal direction is configured to be flexible from a perspective of reducing compression with respect to the lesion part LA. For example, as shown in FIG. 24, a flexible part 36 which is formed by winding a part of the wire 35 in the longitudinal direction in a coil shape may be provided at the wire 35. In addition, an elastic member such as rubber may be provided at a part of the wire 35 in the longitudinal direction. In addition, the wire 35 may be formed of a material having elasticity, such as a braided wire.

Figure 25:
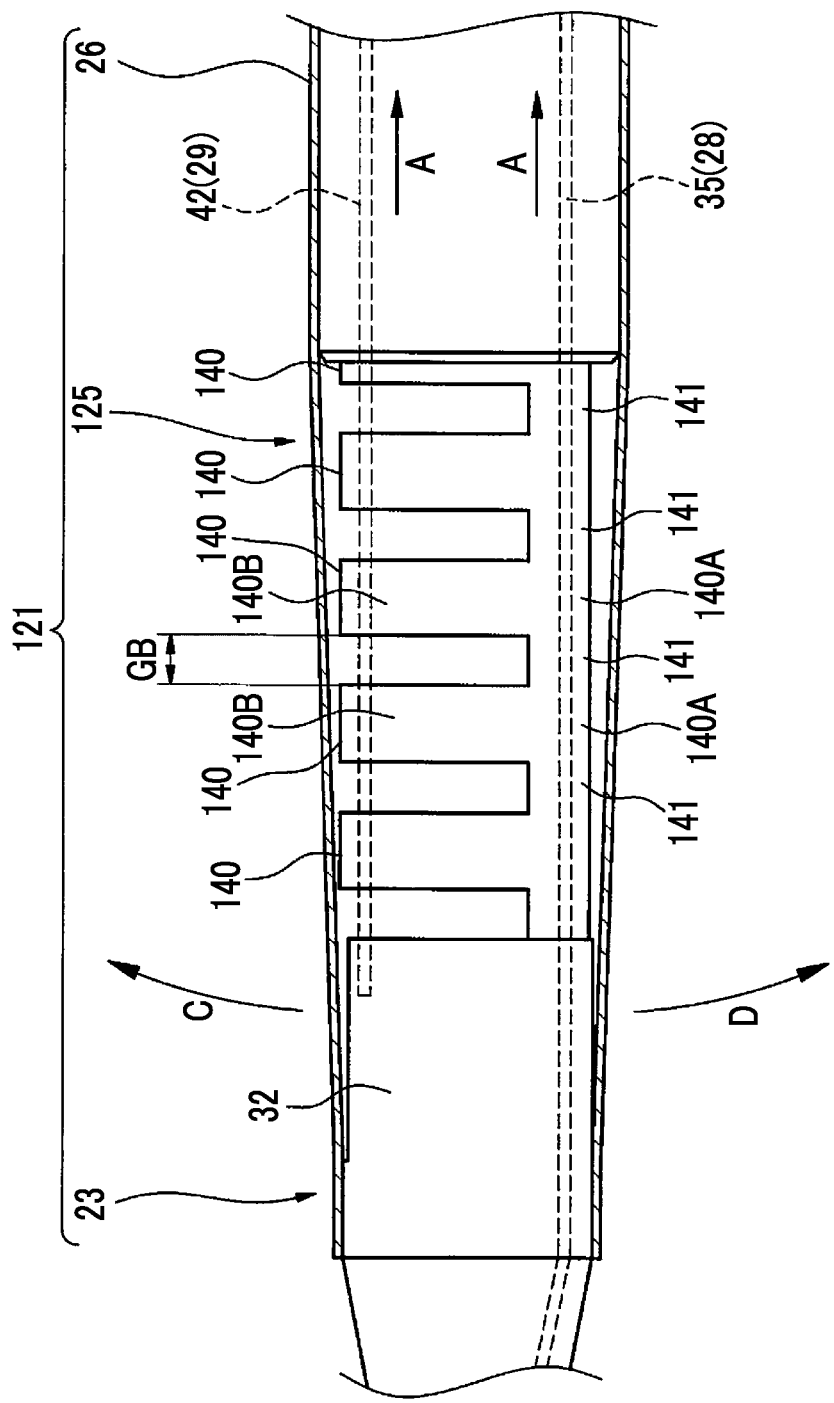
FIG. 25 is a view showing another example of the bendable part of the treatment tool for an endoscope, which is for describing Embodiment 1 of the present invention.
Figure 26:
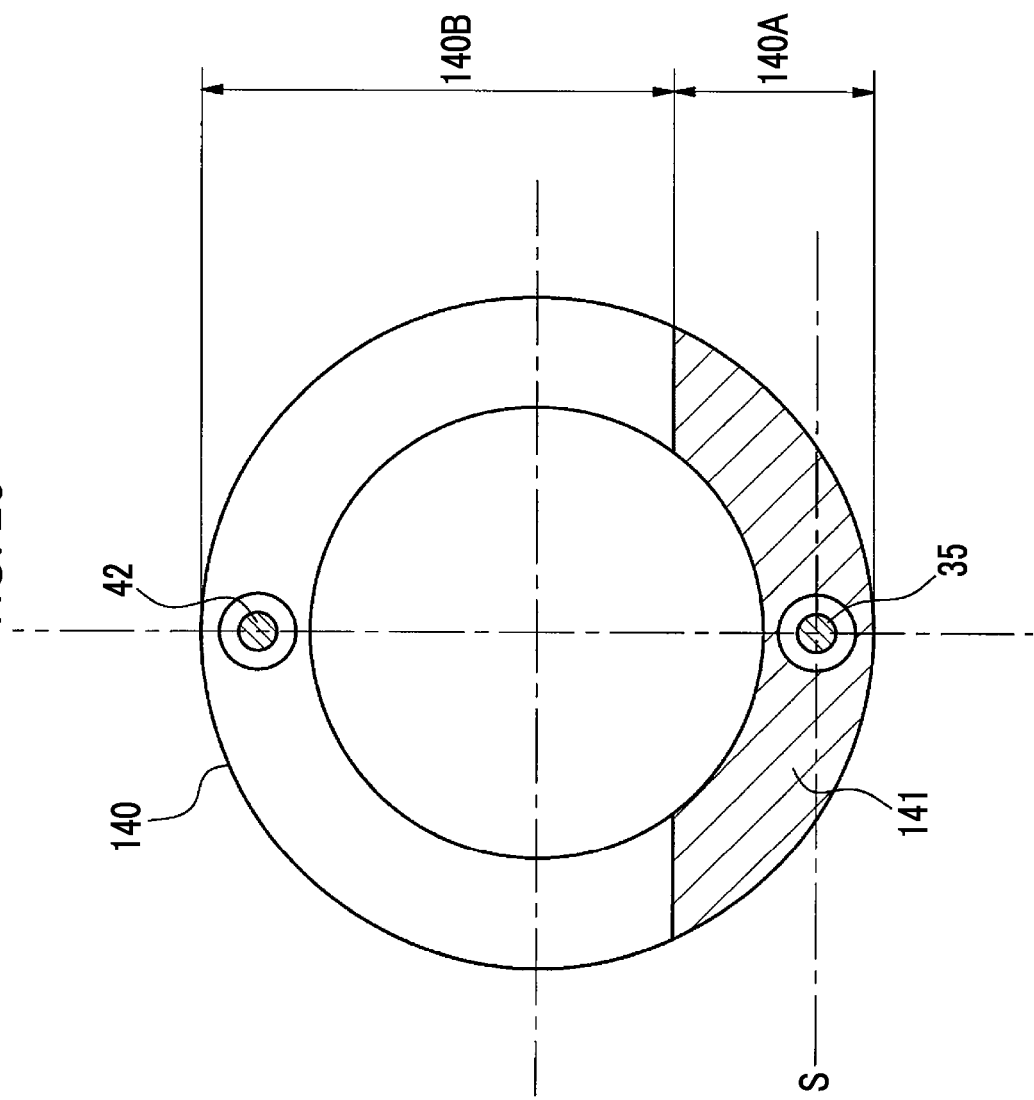
FIG. 26 is a view showing a cross section of the bendable part of FIG. 25.

A treatment tool for an endoscope 120 shown in FIGS. 25 and 26 is configured such that the bendable part is bendable in one direction and is not bendable in an opposite direction. The treatment tool for an endoscope 120 and the treatment tool for an endoscope 20 described above are different from each other only in terms of the configuration of the bendable part. Thus, common elements will be assigned with common reference numerals, and description thereof will be omitted.

An insertion part 121 of the treatment tool for an endoscope 120 comprises the distal end part 23, the bendable part 125, and the soft portion 26. The bendable part 125 has a plurality of cyclic portions 140 arranged in an axial direction of the insertion part 121 and one or more connecting portions 141 that connect two cyclic portions 140 adjacent to each other. The cyclic portions 140 and the connecting portions 141 are formed integrally with each other. In a cross section perpendicular to the axial direction of the insertion part 121, the connecting portions 141 are formed in an arc shape that is concave to a central axis side of the insertion part 121.

In a case where the cyclic portion 140 is divided into a first portion 140A connected to the connecting portion 141 and a second portion 140B excluding the first portion 140A, there is the gap GB between the second portions 140B of the two cyclic portions 140 adjacent to each other. The connecting portion 141 having an arc-shaped cross section is capable of only bending a concave surface inward of bending the concave surface inward and bending the concave surface outward. Therefore, the bendable part 125 is bendable only in the C-direction, in which the gap GB is narrowed, with the bending of the concave surface of the connecting portion 141 inward, and is not bendable in the D-direction opposite to the C-direction. The bent neutral plane S of the bendable part 125 passes through a circumferential middle portion of each of the plurality of connecting portions 141 arranged in the axial direction of the insertion part 121.

The wire 42 which is the second transmitting member 29 is disposed on the bent inner diameter side in the bending of the bendable part 125 in the C-direction. The gap GB is narrowed as the wire 42 is moved in the A-direction, and thus the bendable part 125 is bent in the C-direction. The wire 35 which is the first transmitting member 28 is disposed on the bent neutral plane S of the bendable part 125. Since the bendable part 125 is not bendable in the D-direction opposite to the C-direction, based on an operation of the operating part 22, the wire 35 is moved in the A-direction prior to the wire 42, and in a case where the grip part 24 is closed, the bendable part 125 is reliably maintained in a linear shape. Accordingly, a relative movement between the grip part 24 and the lesion part LA gripped by the grip part 24 is prevented, and the gripping of the lesion part LA becomes even easier.

Figure 27:
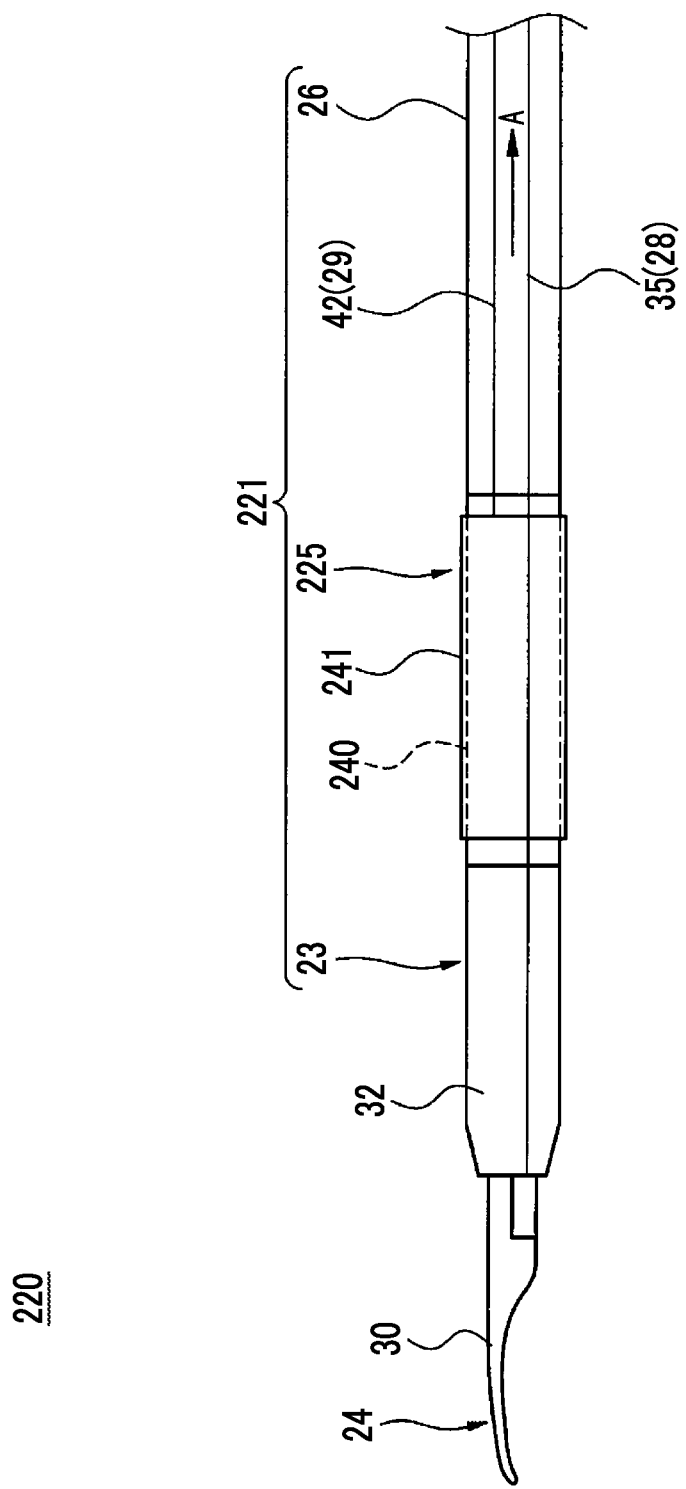
FIG. 27 is a view showing still another example of the bendable part of the treatment tool for an endoscope, which is for describing Embodiment 1 of the present invention.
Figure 28:
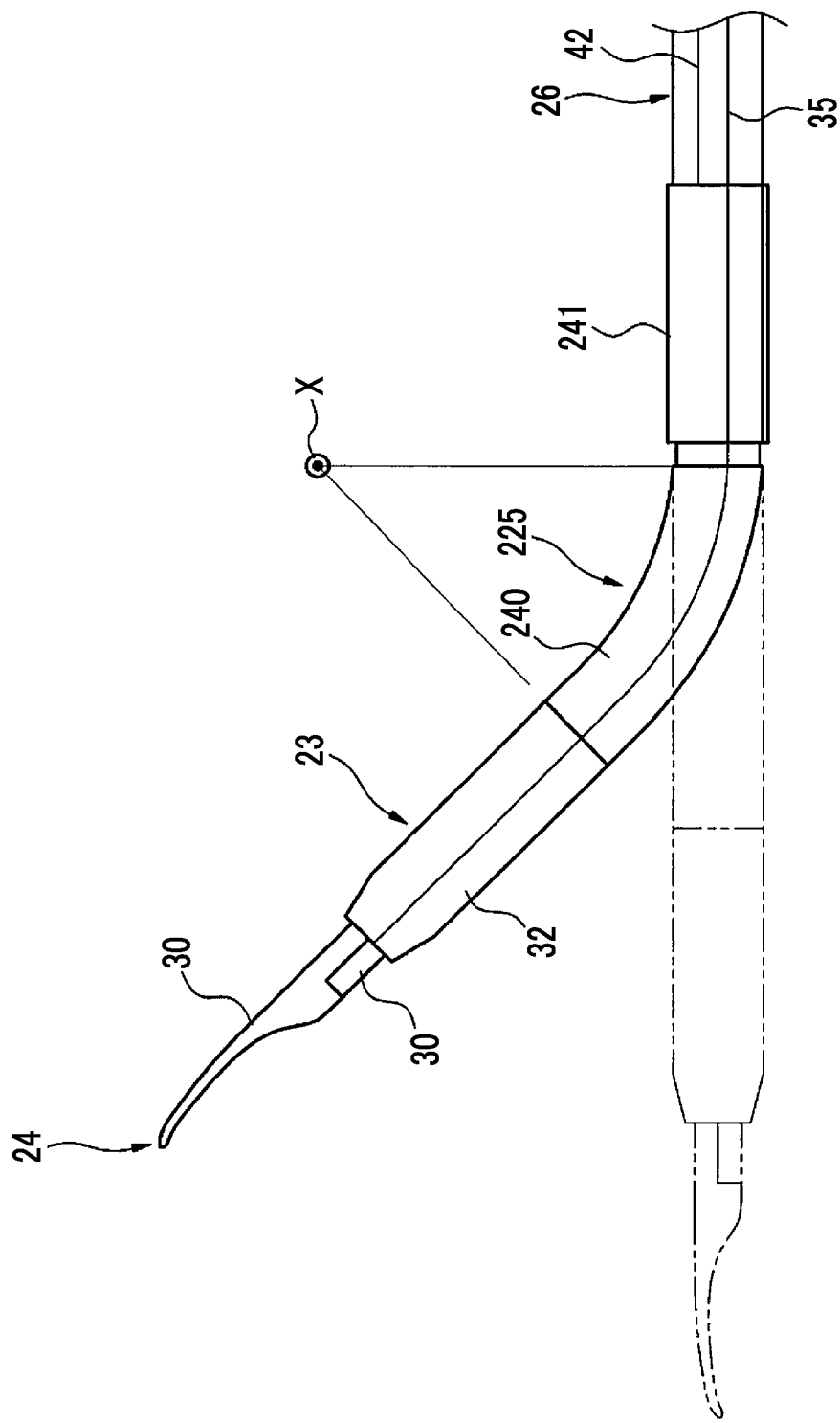
FIG. 28 is a view showing an operation of the bendable part of FIG. 27.

A treatment tool for an endoscope 220 shown in FIGS. 27 and 28 is also configured such that the bendable part is bendable in one direction and is not bendable in an opposite direction. The treatment tool for an endoscope 220 and the treatment tool for an endoscope 20 described above are different from each other only in terms of the configuration of the bendable part. Thus, common elements will be assigned with common reference numerals, and description thereof will be omitted.

An insertion part 221 of the treatment tool for an endoscope 220 comprises the distal end part 23, a bendable part 225, and the soft portion 26. The bendable part 225 has a tubular member 240 and a restraining member 241. The tubular member 240 is bent in the C-direction about the bending central axis X parallel to the opening and closing direction of the pair of grip claws 30 of the distal end part 23, and is elastically deformable in a linear shape. The restraining member 241 is formed in a tubular shape that can accommodate the tubular member 240, and covers the tubular member 240 so as to be movable in an axial direction of the insertion part 221. The wire 42 which is the second transmitting member 29 is connected to the restraining member 241.

The restraining member 241 is a linear hard member, and the tubular member 240 is restrained in a linear shape by the restraining member 241 in a state where the restraining member 241 covers the tubular member 240. As the wire 42 is moved in the A-direction, the restraining member 241 is moved to the soft portion 26, and the tubular member 240 is released from the restraint of the restraining member 241. Accordingly, the tubular member 240 bends due to a restoring force of the tubular member 240, and the bendable part 225 is bent in the C-direction. Based on an operation of the operating part 22, the wire 35 is moved in the A-direction prior to the wire 42, and in a case where the grip part 24 is closed, the tubular member 240 is restrained by the restraining member 241 and the bendable part 225 is reliably maintained in a linear shape. Accordingly, a relative movement between the grip part 24 and the lesion part LA gripped by the grip part 24 is prevented, and the gripping of the lesion part LA becomes even easier.

The restraining member 241 may cover at least the bent inner diameter side of the tubular member 240, and is not limited to a tubular shape that can accommodate the tubular member 240. In addition, the wire 35 which is the first transmitting member 28 and the wire 42 which is the second transmitting member 29 may be disposed on any of the bent inner diameter side in the bending of the bendable part 225 in the C-direction, the bent outer diameter side, or the bent neutral plane.

Figure 29:
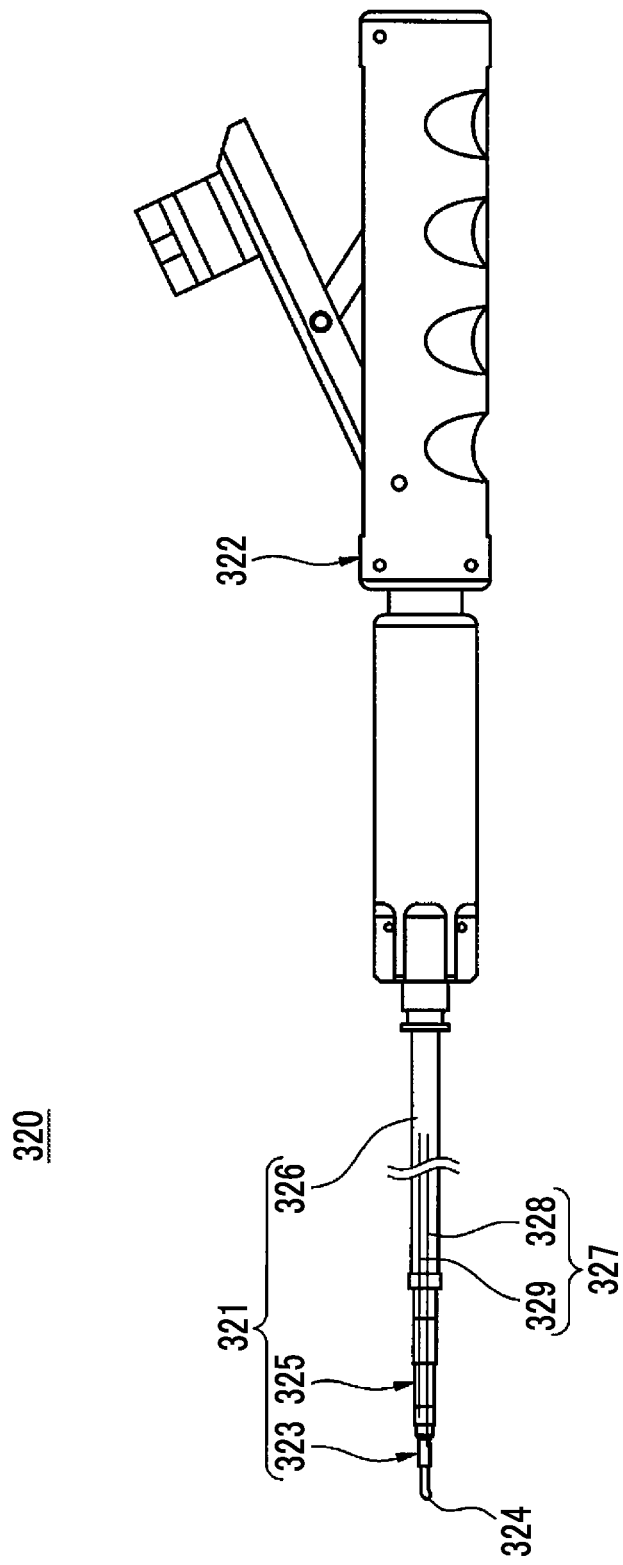
FIG. 29 is a view showing another example of the treatment tool for an endoscope, which is for describing Embodiment 1 of the present invention.

FIG. 29 shows another example of the treatment tool for an endoscope, which is for describing Embodiment 1 of the present invention.

A treatment tool for an endoscope 320 comprises an insertion part 321 and an operating part 322. The insertion part 321 has a distal end part 323 at which an openable and closable grip part 324 is provided, a bendable part 325 that is provided adjacent to an operating part side of the distal end part 323 and is bendable, and a soft portion 326 that connects the bendable part 325 to the operating part 322. A closing operation of closing the grip part 324 and a bending operation of bending the bendable part 325 are input into the operating part 322. The treatment tool for an endoscope 320 further comprises a transmitting part 327 that transmits the operations of the operating part 322 to the grip part 324 and the bendable part 325.

The transmitting part 327 has a first transmitting member 328 that extends from the grip part 324 toward the operating part 322 and a second transmitting member 329 that extends from the bendable part 325 toward the operating part 322. The first transmitting member 328 and the second transmitting member 329 are accommodated inside the soft portion 326. The closing operation input into the operating part 322 is transmitted to the grip part 324 via the first transmitting member 328, and the bending operation input into the operating part 322 is transmitted to the bendable part 325 via the second transmitting member 329.

Figure 30:
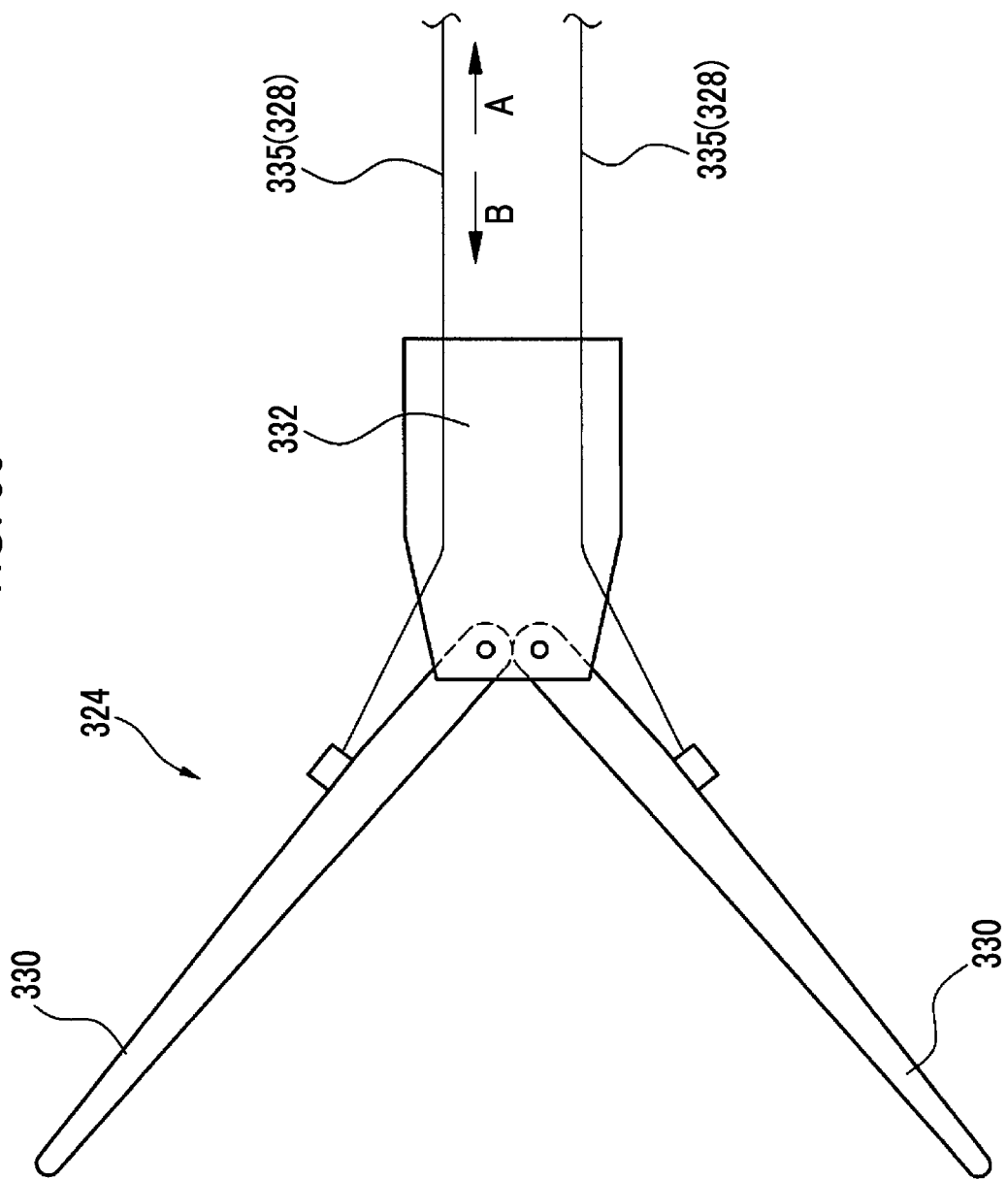
FIG. 30 is a view showing the grip part of the treatment tool for an endoscope of FIG. 29.
Figure 31:
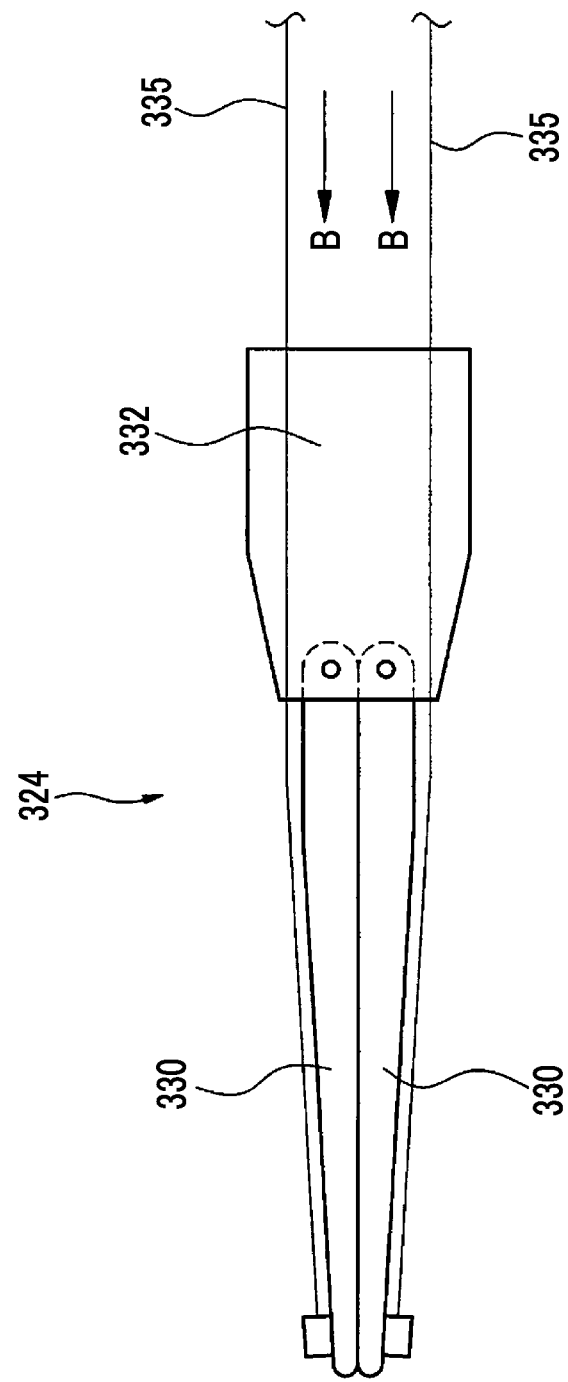
FIG. 31 is a view showing an operation of the grip part of FIG. 30.

FIGS. 30 and 31 show the grip part 324.

The grip part 324 has a pair of grip claws 330 and a support 332 that supports each of a proximal end part of the pair of grip claws 330 so as to be movable rotationally. As the first transmitting member 328 that transmits the closing operation of the operating part 322 to the grip part 324, two wires 335 are used, and the wires 335 are connected to the grip claws 330 so as to be movable in a longitudinal direction of the grip claws 330. Instead of the two wires 335, a single wire of which a distal end side is branched into two may be used.

The wire 335 is pushed out to a distal end part 323 side based on the closing operation of the operating part 322. Herein, as for movement of the wire 335, pulling to an operating part 322 side is defined as a movement in the A-direction, and pushing out to the distal end part 323 side is defined as a movement in the B-direction. FIG. 30 shows a state where the wire 335 is pulled to the operating part 322 side, and distal end parts of the pair of grip claws 330 are open. By moving the wire 335 in the B-direction (first direction) based on the closing operation of the operating part 322, the distal end parts of the pair of grip claws 330 are closed as shown in FIG. 31.

Figure 32:
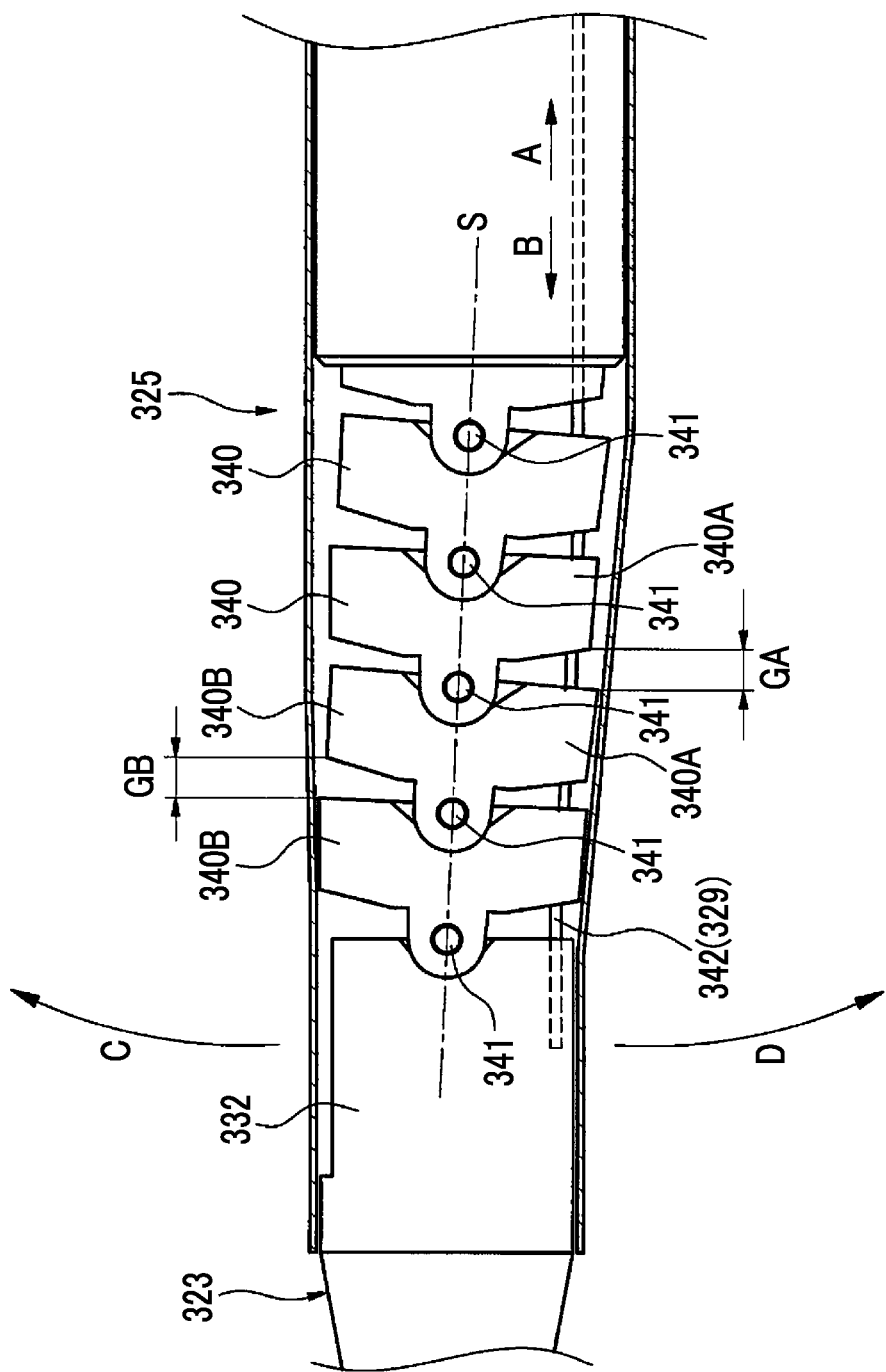
FIG. 32 is a view showing the bendable part of the treatment tool for an endoscope of FIG. 29.
Figure 33:
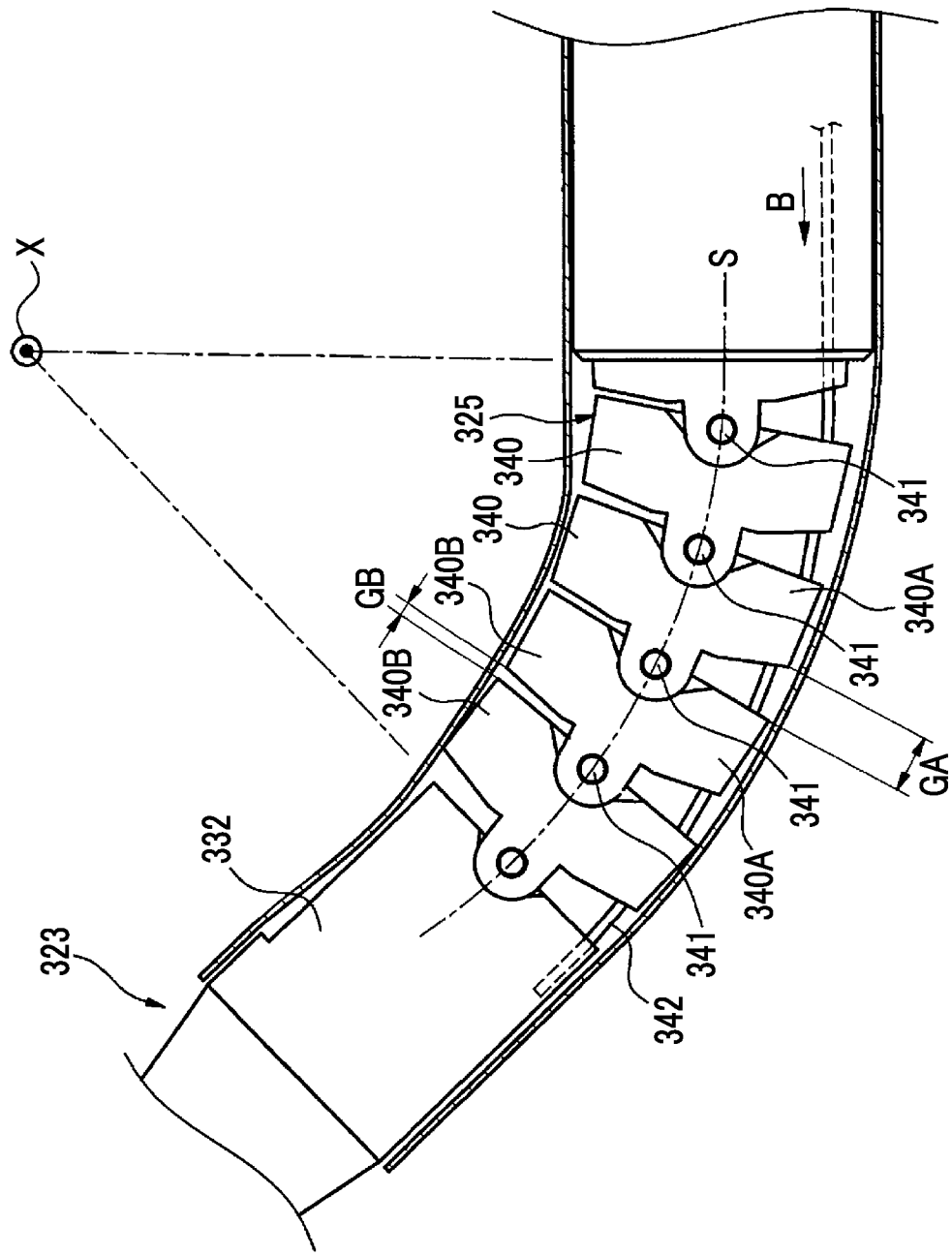
FIG. 33 is a view showing an operation of the bendable part of FIG. 32.

FIGS. 32 and 33 show the bendable part 325.

The bendable part 325 has a plurality of cyclic members 340 arranged in an axial direction of the insertion part 321, and two cyclic members 340 adjacent to each other are connected by a pair of pins 341 so as to be movable rotationally. The bending of the bendable part 325 is the sum of rotational movements of the plurality of cyclic members 340, and the bent neutral plane S of the bendable part 325 passes through the plurality of pins 341 arranged in the axial direction of the insertion part 321. In a case where the cyclic member 340 is divided into a first portion 340A and a second portion 340B with the bent neutral plane S as a boundary, there is the gap GA between the first portions 340A of the two cyclic members 340 adjacent to each other, and there is the gap GB also between the second portions 340B. Therefore, the bendable part 325 is bendable in the C-direction in which the gap GB on a second portion 340B side is narrowed, and is bendable also in the D-direction in which the gap GA on a first portion 340A side is narrowed.

The bendable part 325 is bendable in both directions including the C-direction and the D-direction, but is bent in the C-direction based on an operation of the operating part 322. As the second transmitting member 329 that transmits the operation of the operating part 322 to the bendable part 325, a wire 342 is used in the present example, and a distal end part of the wire 342 is fixed to the support 332 of the distal end part 323. The wire 342 is pushed out to the distal end part 323 side based on the operation of the operating part 322. Herein, as for movement of the wire 342, pulling to the operating part 322 side is defined as a movement in the A-direction, and pushing out to the distal end part 323 side is defined as a movement in the B-direction.

In the bending of the bendable part 325 in the C-direction, the first portion 340A of the cyclic member 340 is positioned on the bent outer diameter side, and the second portion 340B is positioned on the bent inner diameter side. As the wire 342 is disposed on the bent outer diameter side in the bending of the bendable part 325 in the C-direction and the wire 342 is moved in the B-direction (first direction) based on the bending operation of the operating part 322, the gap GA on the first portion 340A side between the two cyclic members 340 adjacent to each other is widened, conversely the gap GB on the second portion 340B side is narrowed, and the bendable part 325 is bent in the C-direction.

Figure 34:
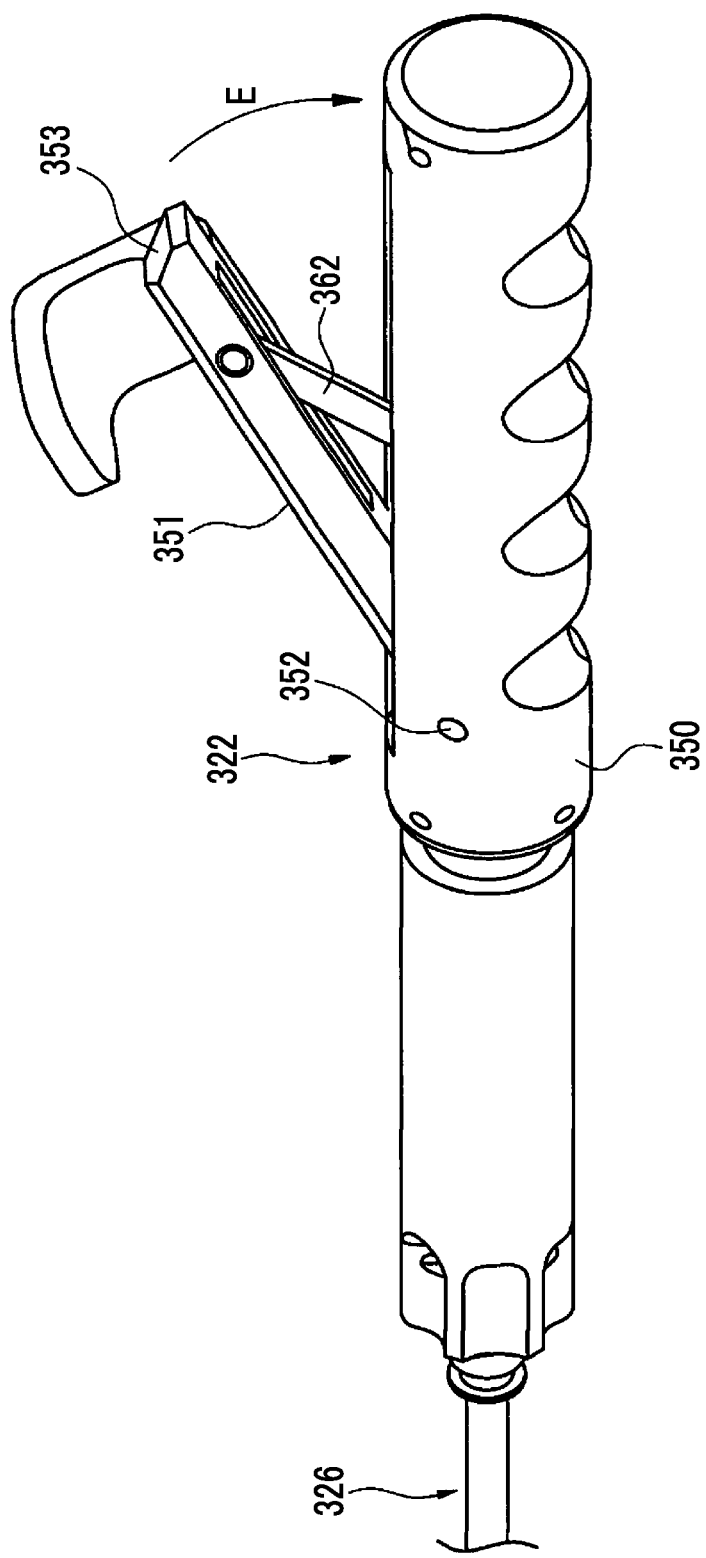
FIG. 34 is a view showing the operating part of the treatment tool for an endoscope of FIG. 29.

FIG. 34 shows the operating part 322.

The operating part 322 has an operating part body 350 and an operating handle 351 swingably supported by the operating part body 350. The operating handle 351 is operated in the E-direction in which a free end part 353 of the operating handle 351 approaches the operating part body 350. In response to the operation of the operating handle 351 in the E-direction, the wire 335 which is the first transmitting member 328 of the transmitting part 327 is moved in the B-direction, and the grip part 324 is closed as described above. In addition, in response to the operation of the operating handle 351 in the E-direction, the wire 342 which is the second transmitting member 329 of the transmitting part 327 is also moved in the B-direction, and the bendable part 325 is bent as described above.

Figure 35:
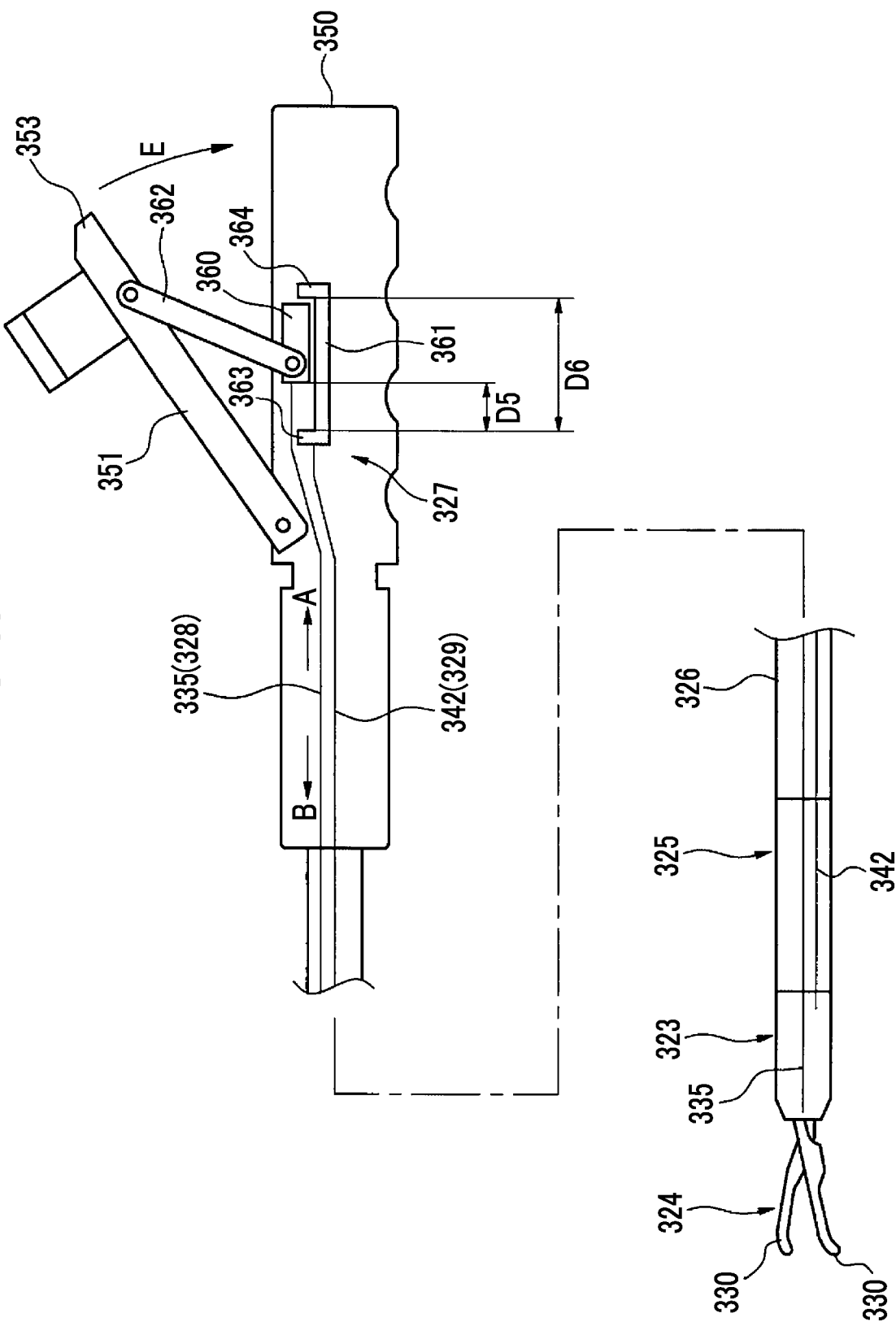
FIG. 35 is a view showing the transmitting part of the treatment tool for an endoscope of FIG. 29.

FIG. 35 shows the transmitting part 327.

The transmitting part 327 has a first slider 360 which is a first movable body and a second slider 361 which is a second movable body. The first slider 360 and the second slider 361 are provided inside the operating part body 350, and are movable in an axial direction of the operating part body 350. The wire 335, which is the first transmitting member 328, is connected to the first slider 360, and the wire 342, which is the second transmitting member 329, is connected to the second slider 361.

The operating handle 351 and the first slider 360 are connected to each other by a link member 362. In response to an operation of the operating handle 351 in the E-direction, the first slider 360 is moved to a distal end part side of the operating part body 350. Accordingly, the wire 335 connected to the first slider 360 is pushed out to the distal end part 323 side, that is, is moved in the B-direction. Since the first slider 360 and the wire 335 are integrated with each other, it can be said that the first slider 360 is also moved in the B-direction.

The second slider 361 has a first abutting part 363 and a second abutting part 364. The first abutting part 363 is disposed on the B-direction side (the distal end part side of the operating part body 350) of the first slider 360, and the second abutting part 364 is disposed on the A-direction side (the proximal end part side of the operating part body 350) of the first slider 360. In a case where the operating handle 351 is not operated, an interval D5 is placed between the first slider 360 and the first abutting part 363, and a stroke of the first slider 360 with respect to an operation of the operating handle 351 in the E-direction is larger than the interval D5. In addition, an interval D6 between the first abutting part 363 and the second abutting part 364 is smaller than the stroke of the first slider 360 with respect to the operation of the operating handle 351 in the E-direction.

In response to an operation of the operating handle 351 in the E-direction, first, the first slider 360 is moved independently in the B-direction by the interval D5. Accordingly, the wire 335 is moved in the B-direction by the interval D5, and the grip part 324 is closed. On the other hand, the second slider 361 and the wire 342 are not moved, and the bendable part 325 is maintained in a linear shape. In response to a further operation of the operating handle 351 in the E-direction, the first slider 360 moved in the B-direction abuts against the first abutting part 363, and the second slider 361 is moved in the B-direction integrally with the first slider 360. Accordingly, the wire 342 is moved in the B-direction, and the bendable part 325 is bent. The grip part 324 is maintained in a closed state.

In a case where the operating handle 351 returns to an unoperated state, the first slider 360 connected to the operating handle 351 is moved in the A-direction which is opposite to the B-direction. Accordingly, the wires 335 is moved in the A-direction, and the grip part 324 is opened. Further, the first slider 360 moved in the A-direction abuts against the second abutting part 364, and the second slider 361 is moved in the A-direction integrally with the first slider 360. Accordingly, the wire 342 is moved in the A-direction, and the bendable part 325 is restored to a linear shape. In order to restore the bendable part 325 to a linear shape, an elastic member such as a leaf spring and a coil spring may be provided in the bendable part 325.

The configuration of the transmitting part 327 described above is an example. For example, the first movable body and the second movable body may be composed of racks like the transmitting part 27 shown in FIG. 14, and the first movable body and the second movable body may be provided at the soft portion 326 like the transmitting part 27 shown in FIG. 17.

The treatment tool for an endoscope 320 is used, for example, in the treatment method shown in FIGS. 18 to 21. First, the grip part 324 is closed based on an operation of the operating part 322, and the lesion part LA is gripped by the grip part 324. Then, after the lesion part LA is gripped by the grip part 324, the bendable part 325 is bent based on the operation of the operating part 322. Accordingly, the grip part 324 is erected, and the lesion part LA gripped by the grip part 324 is lifted.

In the treatment method described above, the gripping of the lesion part LA by closing the grip part 324 and the lifting of the lesion part LA by bending the bendable part 325 are performed only with an operation of the operating part 322 as described above. Further, in a case where the grip part 324 is closed, the bendable part 325 is maintained in a linear shape, and a relative movement between the grip part 324 and the lesion part LA is prevented. Accordingly, the gripping of the lesion part LA and the lifting of the gripped lesion part LA can be easily performed with an operation of the treatment tool for an endoscope 320 alone.

In the treatment tool for an endoscope 320, based on an operation of the operating part 322, first, the wire 335 is moved in the B-direction, and the grip part 324 is closed. Then, after the grip part 324 is closed, the wire 342 is moved in the B-direction, and the bendable part 325 is bent in the C-direction. In this case, the wire 335 is also moved in the B-direction. While the wire 342 is disposed on the bent outer diameter side in the bending of the bendable part 325 in the C-direction, the wire 335 may also be disposed on the bent outer diameter side. Since a length on the bent outer diameter side is extended with the bending, in a case where the wire 335 is disposed on the bent outer diameter side, a movement of the wire 335 in the B-direction is offset. Therefore, an increase in a gripping force of the grip part 324 is prevented, and the lesion part LA is not excessively compressed.

In addition, the wire 335 may be disposed on the bent inner diameter side in the bending of the bendable part 325 in the C-direction or the bent neutral plane S. In a case where the wire 335 is disposed on the bent inner diameter side, the grip part 324 is pressed against the lesion part LA as the bendable part 325 is bent in the D-direction opposite to the C-direction even though the bendable part 325 is bent due to the friction of the wire 335. In addition, in a case where the wire 335 is disposed on the bent neutral plane S, the bending of the bendable part 325 caused by the friction of the wire 335 is further prevented. Accordingly, a relative movement between the grip part 324 and the lesion part LA gripped by the grip part 324 is prevented, and the gripping of the lesion part LA becomes easier.

Further, the bendable part 325 may be configured to be not bendable in the D-direction. In this case, the bending of the bendable part 325 caused by the friction of the wire 335 is reliably prevented.

Figure 36:
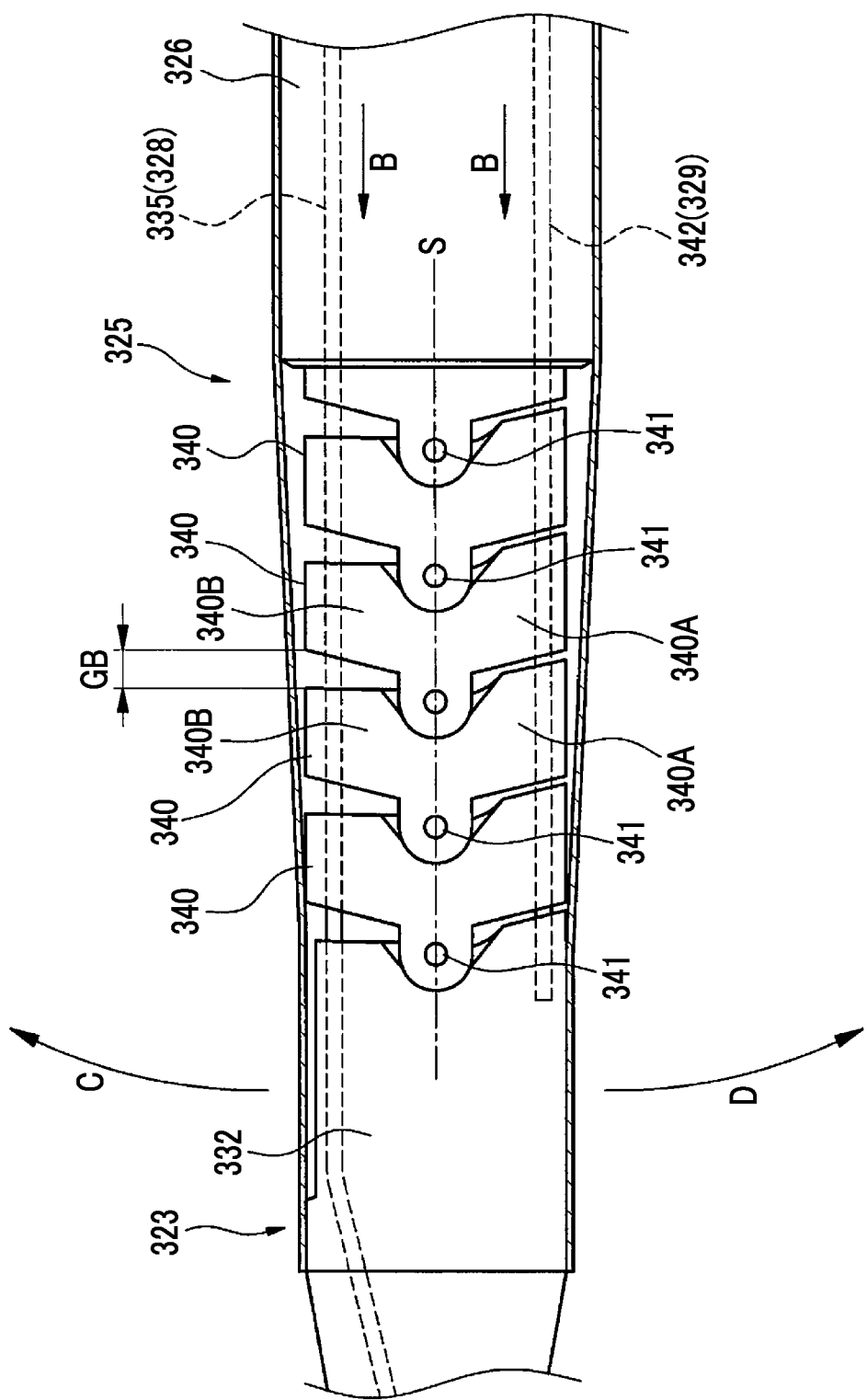
FIG. 36 is a view showing a modification example of the bendable part of FIG. 32.
Figure 37:
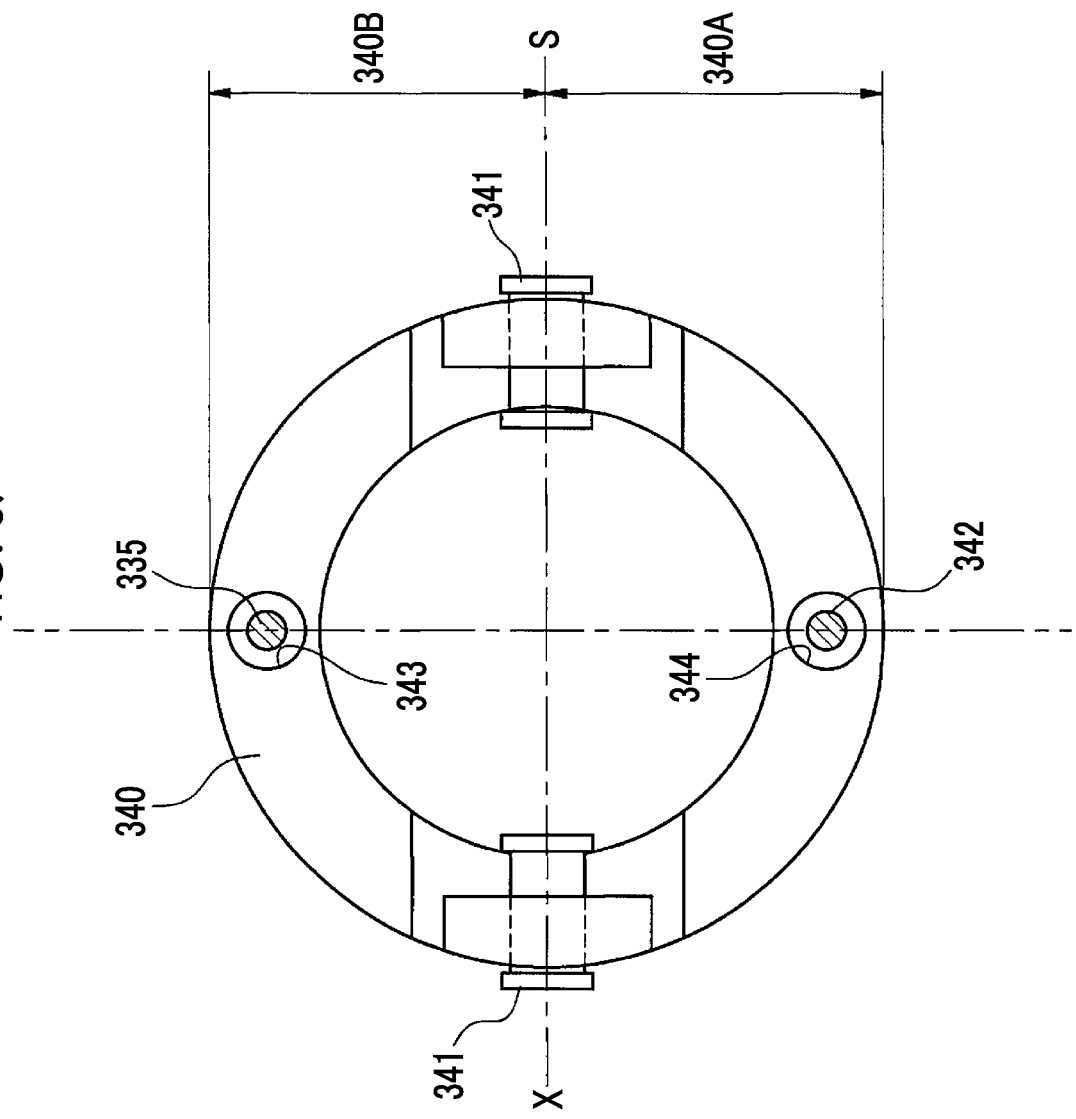
FIG. 37 is a view showing a cross section of the bendable part of FIG. 36.

In a case where the cyclic member 340 is divided into the first portion 340A and the second portion 340B with the bent neutral plane S of the bendable part 325 as a boundary, the second portions 340B of the two cyclic members 340 adjacent to each other are contactless with the gap GB therebetween, in the bendable part 325 shown in FIGS. 36 and 37, the first portions 340A are in contact with each other. Therefore, the bendable part 325 is bendable only in the C-direction, in which the gap GB is narrowed, and is not bendable in the D-direction opposite to the C-direction.

In the bending of the bendable part 325 in the C-direction, the first portion 340A of the cyclic member 340 is positioned on the bent outer diameter side, and the second portion 340B is positioned on the bent inner diameter side. A first guide 343 that holds the wire 335 which is the first transmitting member 328 is provided at the second portion 340B, and the wire 335 is disposed on the bent outer diameter side. A second guide 344 that holds the wire 342 which is the second transmitting member 329 is provided at the first portion 340A, and the wire 342 is disposed on the bent inner diameter side.

The gap GB is narrowed as the wire 342 is moved in the B-direction, and thus the bendable part 325 is bent in the C-direction. In a case where the wire 335 is disposed on the bent outer diameter side which is an opposite side to the wire 342 with the bent neutral plane S interposed therebetween and the bendable part 325 is bent due to the friction of the wire 335 moved in the B-direction, the bendable part 325 is bent in the C-direction opposite to the D-direction, but the bendable part 325 is not bendable in the D-direction. Therefore, based on an operation of the operating part 322, the wire 335 is moved in the B-direction prior to the wire 342, and in a case where the grip part 324 is closed, the bendable part 325 is reliably maintained in a linear shape. Accordingly, a relative movement between the grip part 324 and the lesion part LA gripped by the grip part 324 is prevented, and the gripping of the lesion part LA becomes even easier.

The wire 335 may be disposed on the bent neutral plane S. In a case where the wire 335 is disposed on the bent neutral plane S, the first guide 343 holding the wire 335 is provided, for example, at an end part of the pin 341.

In a case where the wire 335 is disposed on the bent outer diameter side in the bending of the bendable part 325 in the C-direction or is disposed on the bent neutral plane S, a length on the bent inner diameter side is reduced with the bending, and a length on the bent neutral plane S is constant regardless of the bending. Therefore, a movement of the wire 335 in the B-direction after the grip part 324 is closed is not offset by the extension of the length of the wire 335 at a disposed place, and the gripping force of the grip part 324 gradually increases according to the movement of the wire 335 in the B-direction after the grip part 324 is closed.

In a case where the lesion part LA is lifted, the lesion part LA can be more reliably gripped due to an increase in the gripping force of the grip part 324, but it is preferable that at least a part of the wire 335 in a longitudinal direction is configured to be flexible from a perspective of reducing compression with respect to the lesion part LA. For example, like the wire 35 shown in FIG. 24, a flexible part which is formed by winding a part of the wire 335 in the longitudinal direction in a coil shape may be provided at the wire 335. In addition, an elastic member such as rubber may be provided at a part of the wire 335 in the longitudinal direction. In addition, the wire 335 may be formed of a material having elasticity, such as a braided wire.

Figure 38:
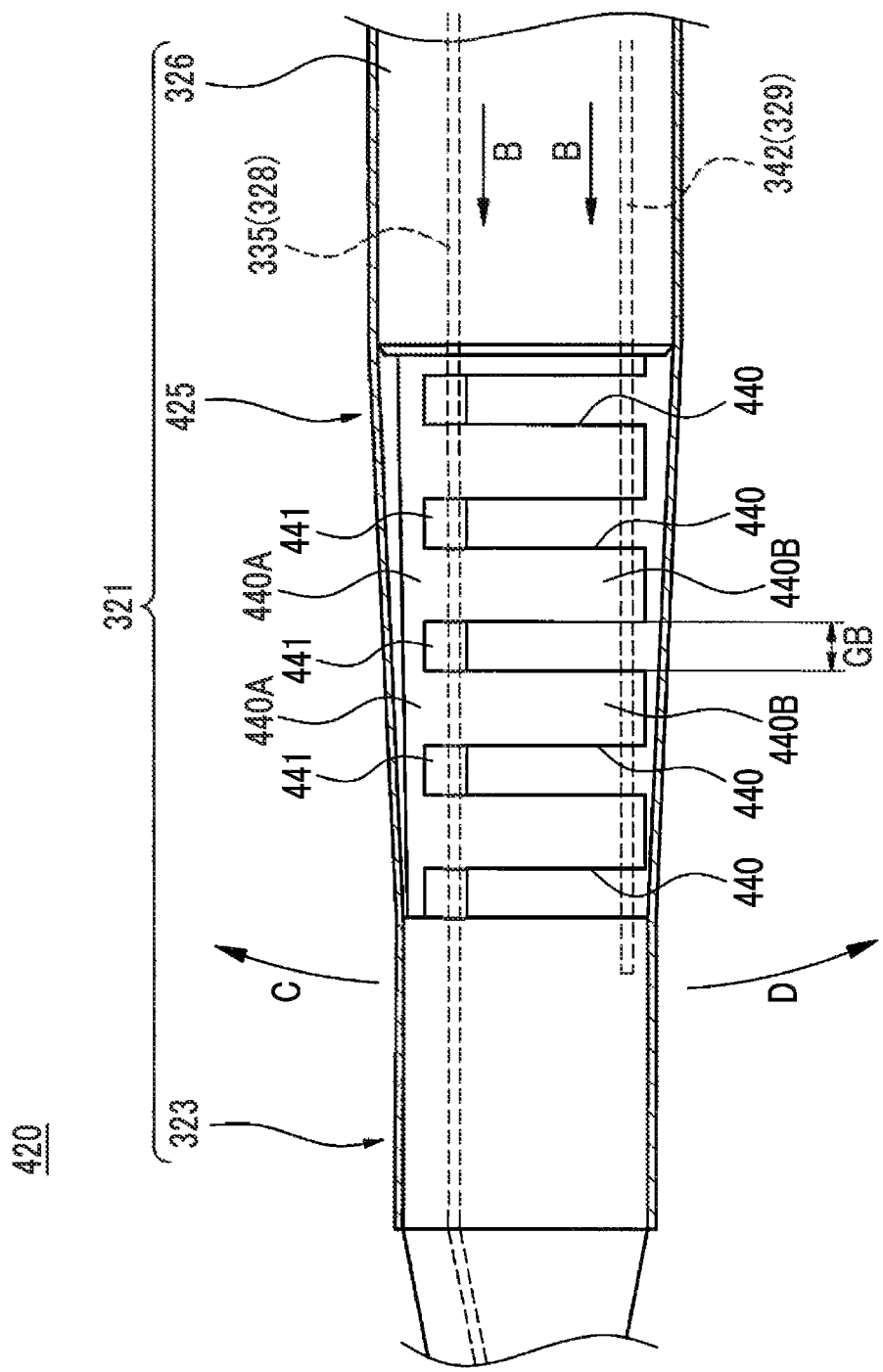
FIG. 38 is a view showing still another example of the bendable part of the treatment tool for an endoscope, which is for describing Embodiment 1 of the present invention.
Figure 39:
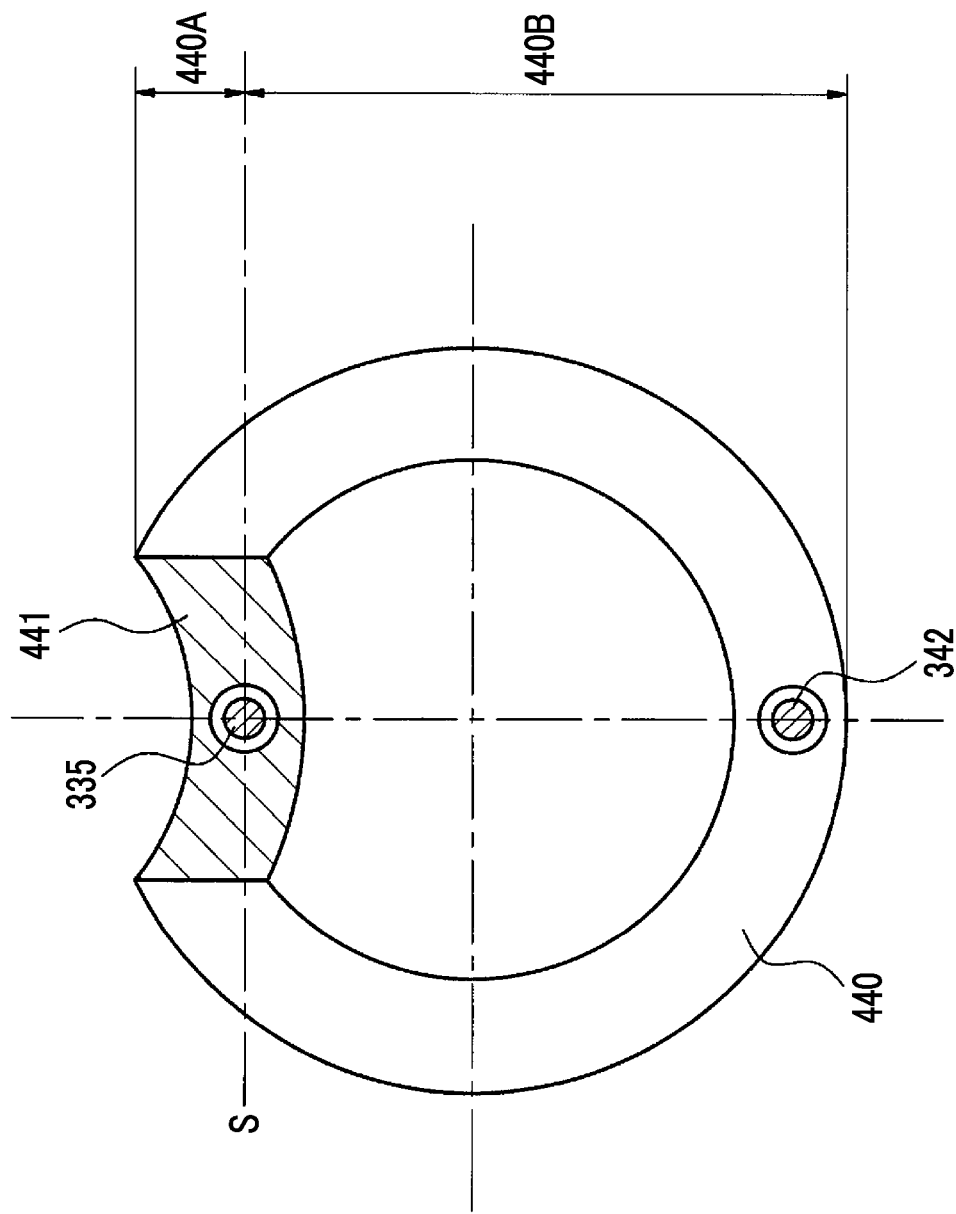
FIG. 39 is a view showing a cross section of the bendable part of FIG. 38.

A treatment tool for an endoscope 420 shown in FIGS. 38 and 39 is also configured such that the bendable part is bendable in one direction and is not bendable in an opposite direction. The treatment tool for an endoscope 420 and the treatment tool for an endoscope 320 described above are different from each other only in terms of the configuration of the bendable part. Thus, common elements will be assigned with common reference numerals, and description thereof will be omitted.

An insertion part 421 of the treatment tool for an endoscope 420 comprises the distal end part 323, a bendable part 425, and the soft portion 326. The bendable part 425 has a plurality of cyclic portions 440 arranged in an axial direction of the insertion part 421 and one or more connecting portions 441 that connect two cyclic portions 440 adjacent to each other. The cyclic portions 440 and the connecting portions 441 are formed integrally with each other. In a cross section perpendicular to the axial direction of the insertion part 421, the connecting portions 441 are formed in an arc shape that is convex to a central axis side of the insertion part 421.

In a case where the cyclic portion 440 is divided into a first portion 440A connected to the connecting portion 441 and a second portion 440B excluding the first portion 440A, there is the gap GB between the second portions 440B of the two cyclic portions 440 adjacent to each other. The connecting portion 441 having an arc-shaped cross section is capable of only bending a concave surface inward of bending the concave surface inward or bending the concave surface outward. Therefore, the bendable part 425 is bendable only in the C-direction, in which the gap GB is widened, with the bending of the concave surface of the connecting portion 441 inward, and is not bendable in the D-direction opposite to the C-direction. The bent neutral plane S of the bendable part 425 passes through a circumferential middle portion of each of the plurality of connecting portions 441 arranged in the axial direction of the insertion part 421.

The wire 342 which is the second transmitting member 329 is disposed on the bent outer diameter side in the bending of the bendable part 425 in the C-direction. The gap GB is widened as the wire 342 is moved in the B-direction, and thus the bendable part 425 is bent in the C-direction. The wire 335 which is the first transmitting member 328 is disposed on the bent neutral plane S of the bendable part 425. Since the bendable part 425 is not bendable in the D-direction opposite to the C-direction, based on an operation of the operating part 322, the wire 335 is moved in the B-direction prior to the wire 342, and in a case where the grip part 324 is closed, the bendable part 425 is reliably maintained in a linear shape. Accordingly, a relative movement between the grip part 324 and the lesion part LA gripped by the grip part 324 is prevented, and the gripping of the lesion part LA becomes even easier.

Embodiment 2

Although the operating part 22 having the operating part body 50 and the operating handle 51 and the operating part 322 having the operating part body 350 and the operating handle 351 have been described in Embodiment 1, a configuration of an operating part into which an operation is input is not limited thereto. A modification example of the operating part will be described in Embodiment 2, and portions which are the same as in Embodiment 1 will be not be described.

Figure 40:
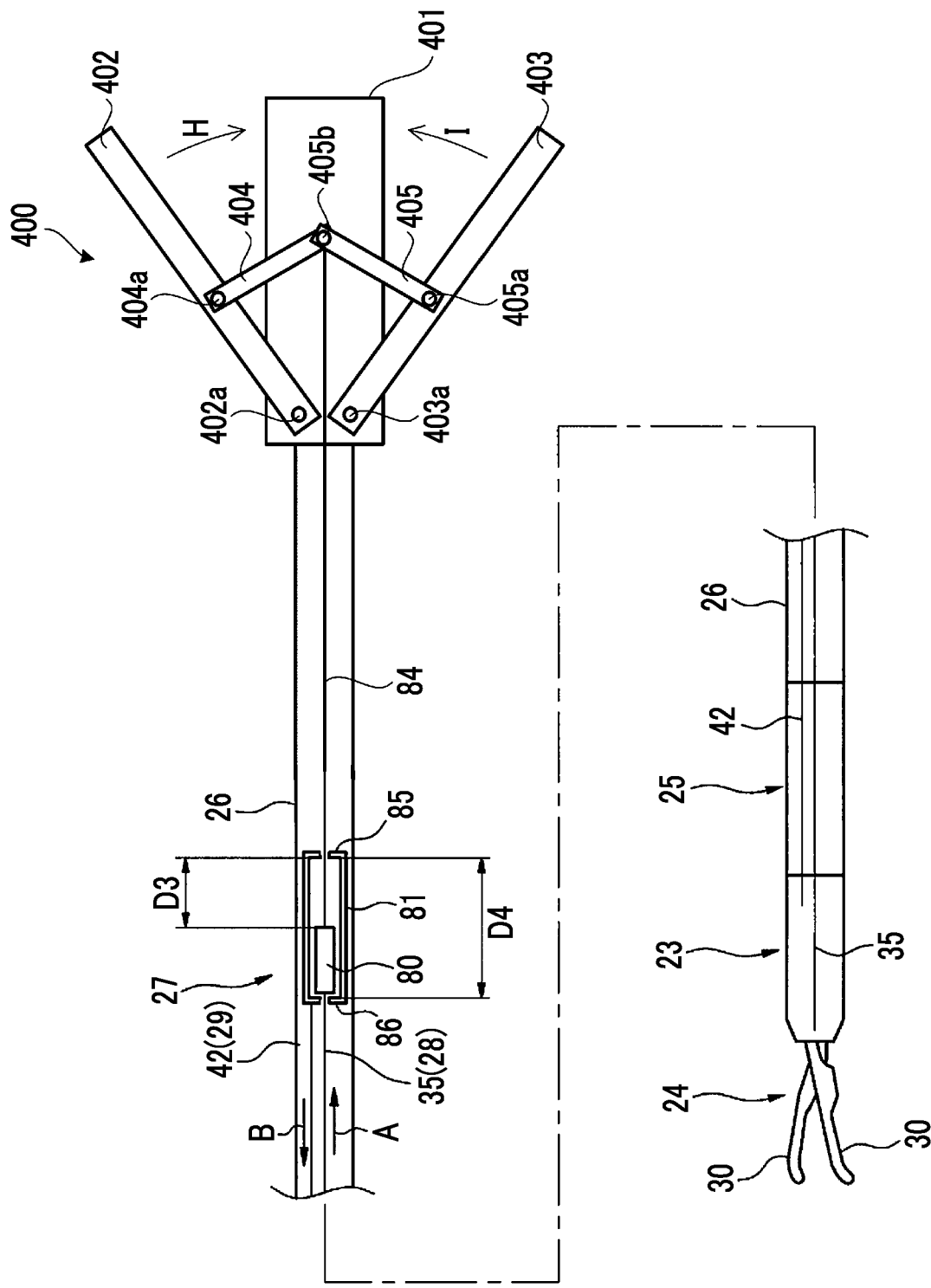
FIG. 40 is a view showing Modification Example 1 of the operating part of the treatment tool for an endoscope, which is for describing Embodiment 2 of the present invention.
Figure 41:
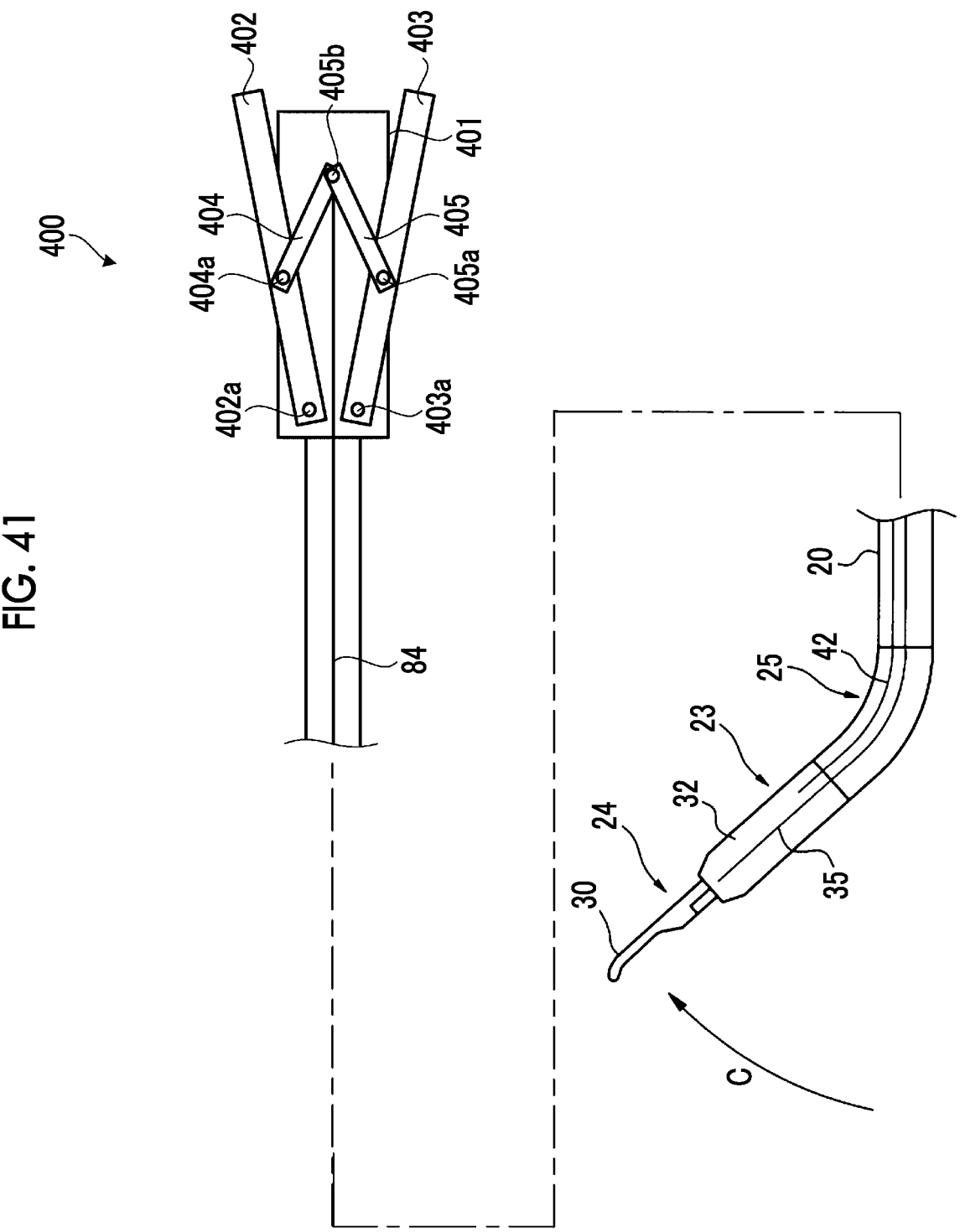
FIG. 41 is a view showing operations of the grip part 24 and the bendable part 25 of FIG. 40.

FIG. 40 is a view showing Modification Example 1 of the operating part of the treatment tool for an endoscope, which is for describing Embodiment 2 of the present invention. For example, in a configuration where the transmitting part 27 is provided at the soft portion 26 as in the configuration shown in FIG. 17, a scissors-type operating part 400 may be provided as shown in FIGS. 40 and 41, instead of the operating part 22. The operating part 400 has an operating part body 401, a pair of handle members 402 and 403, and a pair of link members 404 and 405.

The handle members 402 and 403 are examples of a pair of handle members that are fixed to the operating part body 401 so as to be movable rotationally and are openable and closable with respect to each other due to the rotational movement. One end of the handle member 402 is fixed by a pin 402a to the operating part body 401 so as to be movable rotationally. Similarly, one end of the handle member 403 is fixed by a pin 403a to the operating part body 401 so as to be movable rotationally. It is desirable that a shape of each of the handle members 402 and 403 is a shape that allows a user to grip easily (for example, a flat shape and an elliptical shape).

FIG. 40 shows a state where the pair of handle members 402 and 403 are opened. In this state, for example, as the user grips the pair of handle members 402 and 403 with one hand, the handle member 402 moves rotationally about the pin 402a in an H-direction, and the handle member 403 moves rotationally about the pin 403a in an I-direction. As a result, as shown in FIG. 41, the pair of handle members 402 and 403 are in a closed state.

The link members 404 and 405 and a pin 405b are examples of a displacement member that is displaced according to the opening and closing of the handle members 402 and 403. A first end of the link member 404 is fixed by a pin 404a to a vicinity of a middle portion of the handle member 402 so as to be movable rotationally. A first end of the link member 405 is fixed by a pin 405a to a vicinity of a middle portion of the handle member 403 so as to be movable rotationally. Positions where the first ends of the link members 404 and 405 are fixed are not limited to the vicinities of the middle portions of the handle members 402 and 403, and may be portions of the handle members 402 and 403, other than end parts fixed to the operating part body 401. In addition, second ends of the link members 404 and 405 are fixed to each other by the pin 405b so as to be movable rotationally, and are not fixed to the operating part body 401.

In a case where the pair of handle members 402 and 403 are closed, the link members 404 and 405 are also closed, and accordingly the pin 405b moves in the A-direction. One end of the connecting wire 84 is connected to the pin 405b. The connecting wire 84 is an example of a third transmitting member. Therefore, in response to an operation of closing the pair of handle members 402 and 403, the connecting wire 84 moves in the A-direction.

An operation of the transmitting part 27 accompanying the movement of the connecting wire 84 in the A-direction is the same as the example shown in FIG. 17. For example, in a state where the pair of handle members 402 and 403 are opened as shown in FIG. 40, the grip part 24 is open, and the bendable part 25 extends in a linear shape. From this state, in response to an operation of closing the pair of handle members 402 and 403, first, the grip part 24 is closed like the grip part 24 shown in FIG. 11, and next, the bendable part 25 is bent as shown in FIG. 41.

As described above, in the operating part 400 of Modification Example 1, by adopting a configuration where the link members 404 and 405 and the pin 405b (displacement members) that are displaced according to the opening and closing of the handle members 402 and 403 are provided, and in response to the displacement of the link members 404 and 405 and the pin 405b, first, the first slider 80 is moved in the A-direction, and the second slider 81 moves in the A-direction after the start of the movement of the first slider 80, the gripping of the lesion part and the lifting of the gripped lesion part can be performed with an operation that makes it easy to exert a force, which is gripping with the hand holding the operating part 400.

In addition, in the operating part 400 of Modification Example 1, the link members 404 and 405 and the pin 405b (displacement members) are provided between portions of the handle members 402 and 403 respectively, which are gripped by the user. Accordingly, it is easy for the user to learn that the connecting wire 84 is pulled by gripping the handle members 402 and 403, and it is possible to perform an operation more intuitively.

Although a configuration where the end parts of the handle members 402 and 403 are fixed to the operating part body 401 by the pins 402a and 403a respectively has been described, in the example of FIGS. 40 and 41, portions other than the end parts of the handle members 402 and 403 respectively (for example, the vicinities of the middle portions) may be fixed to the operating part body 401 by the pins 402a and 403a. In this case, as in an example of FIGS. 42 and 43 to be described later, the handle members 402 and 403 may be fixed to the operating part body 50 such that there is an intersecting point in a case of being viewed from a direction perpendicular to the opening and closing direction (a depth direction of FIGS. 42 and 43).

Figure 42:
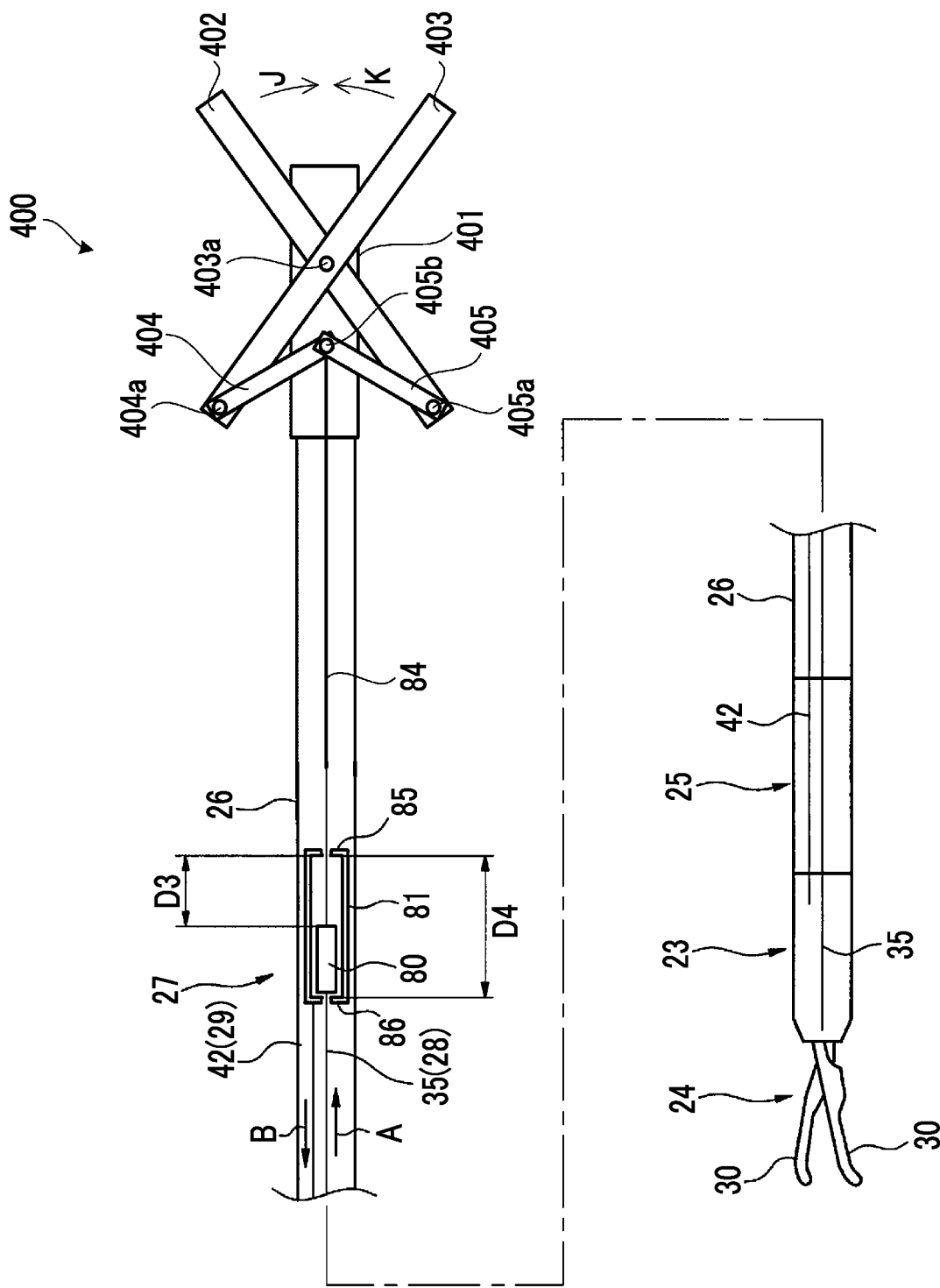
FIG. 42 is a view showing Modification Example 2 of the operating part of the treatment tool for an endoscope, which is for describing Embodiment 2 of the present invention.

FIG. 42 is a view showing Modification Example 2 of the operating part of the treatment tool for an endoscope, which is for describing Embodiment 2 of the present invention. As shown in FIG. 42, portions other than the end parts of the handle members 402 and 403 respectively (for example, the vicinities of the middle portions) in the operating part 400 shown in FIGS. 40 and 41 may be configured to be fixed to one place of the operating part body 401 so as to be movable rotationally about a pin 403b.

FIG. 42 shows a state where the pair of handle members 402 and 403 are opened. In this state, for example, as the user grips the pair of handle members 402 and 403 with one hand, the handle member 402 moves rotationally about the pin 403b in a J-direction, and the handle member 403 moves rotationally about the pin 403b in a K-direction. As a result, as shown in FIG. 43, the pair of handle members 402 and 403 are in a closed state.

Figure 43:
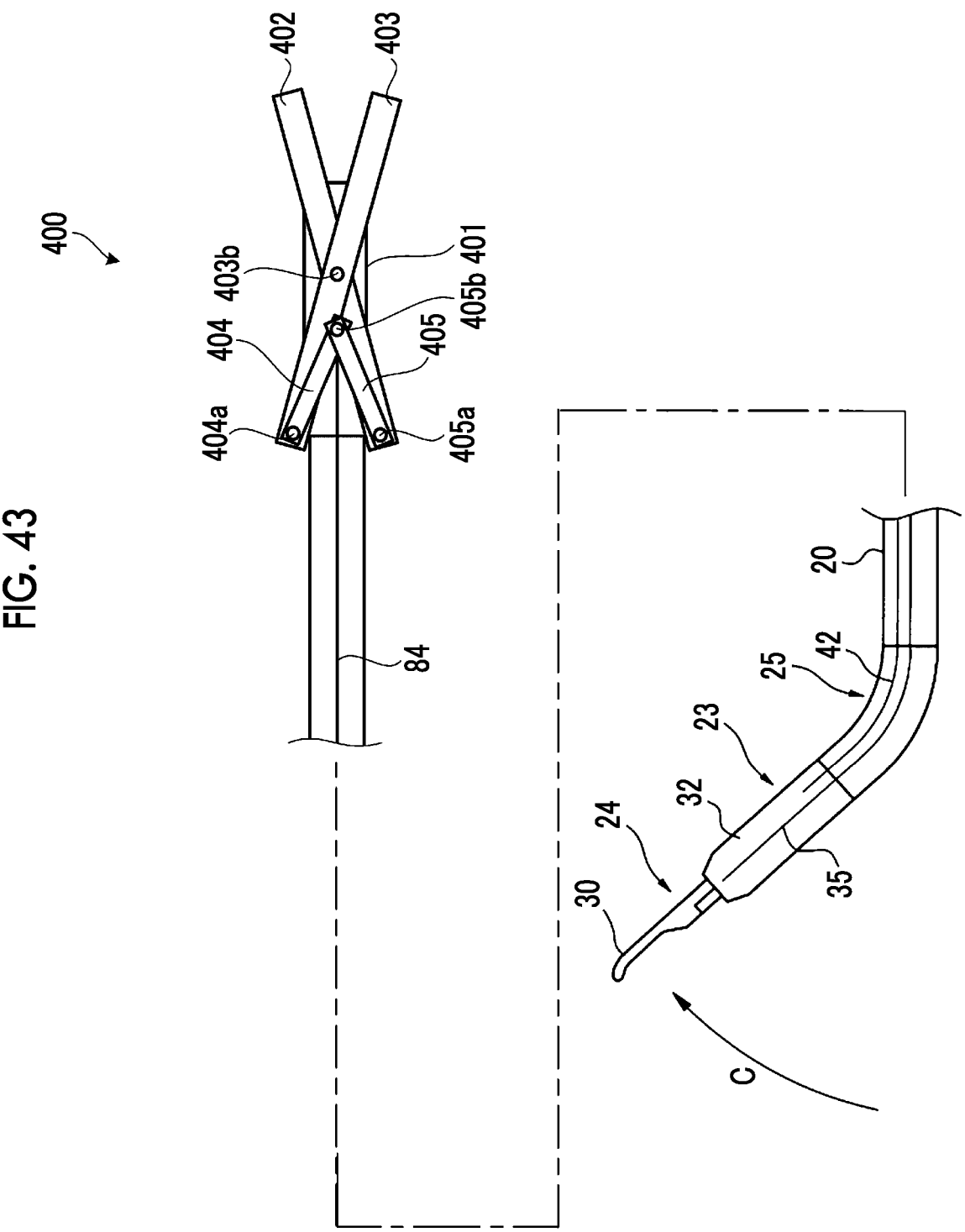
FIG. 43 is a view showing operations of the grip part 24 and the bendable part 25 of FIG. 42.

In the example of FIGS. 42 and 43, the first end of the link member 404 is fixed by a pin 404a to the end part of the handle member 403 so as to be movable rotationally. The first end of the link member 405 is fixed by the pin 405a to the end part of the handle member 402 so as to be movable rotationally. In addition, the second ends of the link members 404 and 405 are fixed to each other by the pin 405b so as to be movable rotationally.

In such a configuration, as in the configuration of FIGS. 40 and 41, in response to an operation of closing the pair of handle members 402 and 403, the connecting wire 84 moves in the A-direction. In a state where the pair of handle members 402 and 403 are opened as shown in FIG. 42, the grip part 24 is open, and the bendable part 25 extends in a linear shape. From this state, in response to the operation of closing the pair of handle members 402 and 403, first, the grip part 24 is closed like the grip part 24 shown in FIG. 11, and next, the bendable part 25 is bent as shown in FIG. 43.

As described above, in the operating part 400 of Modification Example 2, by adopting a configuration where the link members 404 and 405 and the pin 405b (displacement members) that are displaced according to the opening and closing of the handle members 402 and 403 are provided, and in response to the displacement of the link members 404 and 405 and the pin 405b, first, the first slider 80 is moved in the A-direction, and the second slider 81 moves in the A-direction after the start of the movement of the first slider 80, the gripping of the lesion part and the lifting of the gripped lesion part can be performed by an operation that makes it easy to exert a force, which is gripping with the hand holding the operating part 400.

In addition, in the operating part 400 of Modification Example 2, the handle members 402 and 403 may be fixed to the operating part body 50 so as to be movable rotationally such that there is an intersecting point in a case of being viewed from the direction perpendicular to the opening and closing direction (the depth direction of FIGS. 42 and 43). Then, the link members 404 and 405 and the pin 405b (displacement members) are provided between the portions of the handle members 402 and 403 respectively, which are on an opposite side to portions (portions of the pins 404a and 405a) gripped by the user in a case of being viewed from the intersecting point.

Accordingly, the link members 404 and 405 and the pin 405b (displacement members) are unlikely to hinder an operation of gripping the handle members 402 and 403, and the handle members 402 and 403 can be easily closed. For this reason, operability can be improved. In addition, for example, by completely closing the handle members 402 and 403, it becomes a state where a rotational force is not generated, and a pulling state can be maintained even though a high load is applied to the grip part 24.

Figure 44:
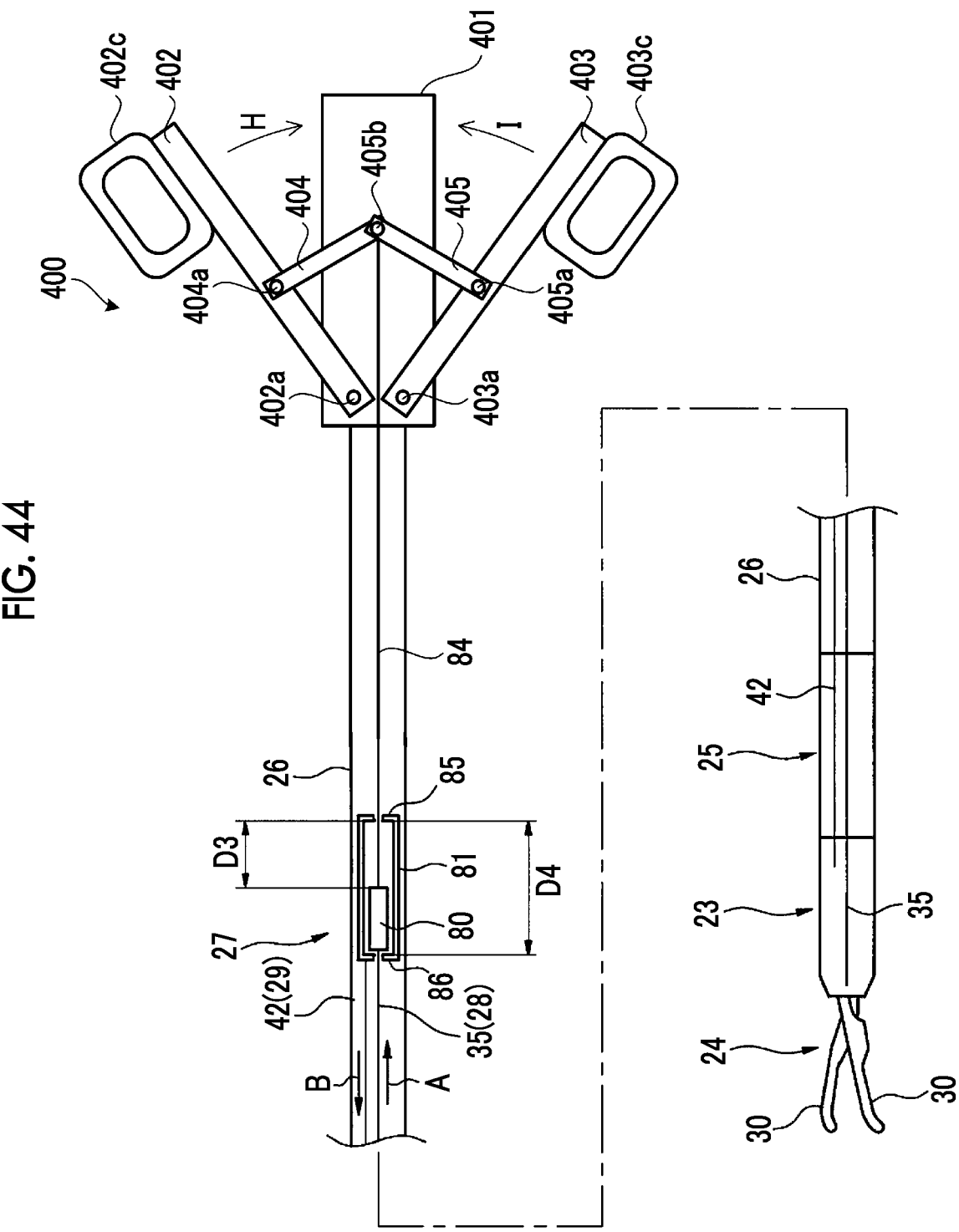
FIG. 44 is a view showing Modification Example 3 of the operating part of the treatment tool for an endoscope, which is for describing Embodiment 2 of the present invention.

FIG. 44 is a view showing Modification Example 3 of the operating part of the treatment tool for an endoscope, which is for describing Embodiment 2 of the present invention. As shown in FIG. 44, a configuration where rings 402c and 403c are provided at the handle members 402 and 403 respectively may be adopted. The rings 402c and 403c are examples of a non-slip member preventing the hand from slipping. Accordingly, in a case where the user grips the operating part 400, the hand of the user is unlikely to slip on the handle members 402 and 403, and operability improves.

Although a configuration where the rings 402c and 403c are provided at the operating part 400 shown in FIGS. 40 and 41 has been described in FIG. 44, a configuration where the rings 402c and 403c are provided at the operating part 400 shown in FIGS. 42 and 43 may be adopted. In addition, a configuration where a finger hook which is not cyclic may be provided instead of the cyclic rings 402c and 403c.

As described above, in the operating part 400 of Modification Example 3, as non-slip members (for example, the rings 402c and 403c and the finger hook) preventing the slipping of the hand are included in the portions of the handle members 402 and 403 respectively, which are gripped by the user, slipping which occurs in a case of gripping with the hand holding the operating part 400 can be prevented, and further exerting a force can be made easier.

Figure 45:
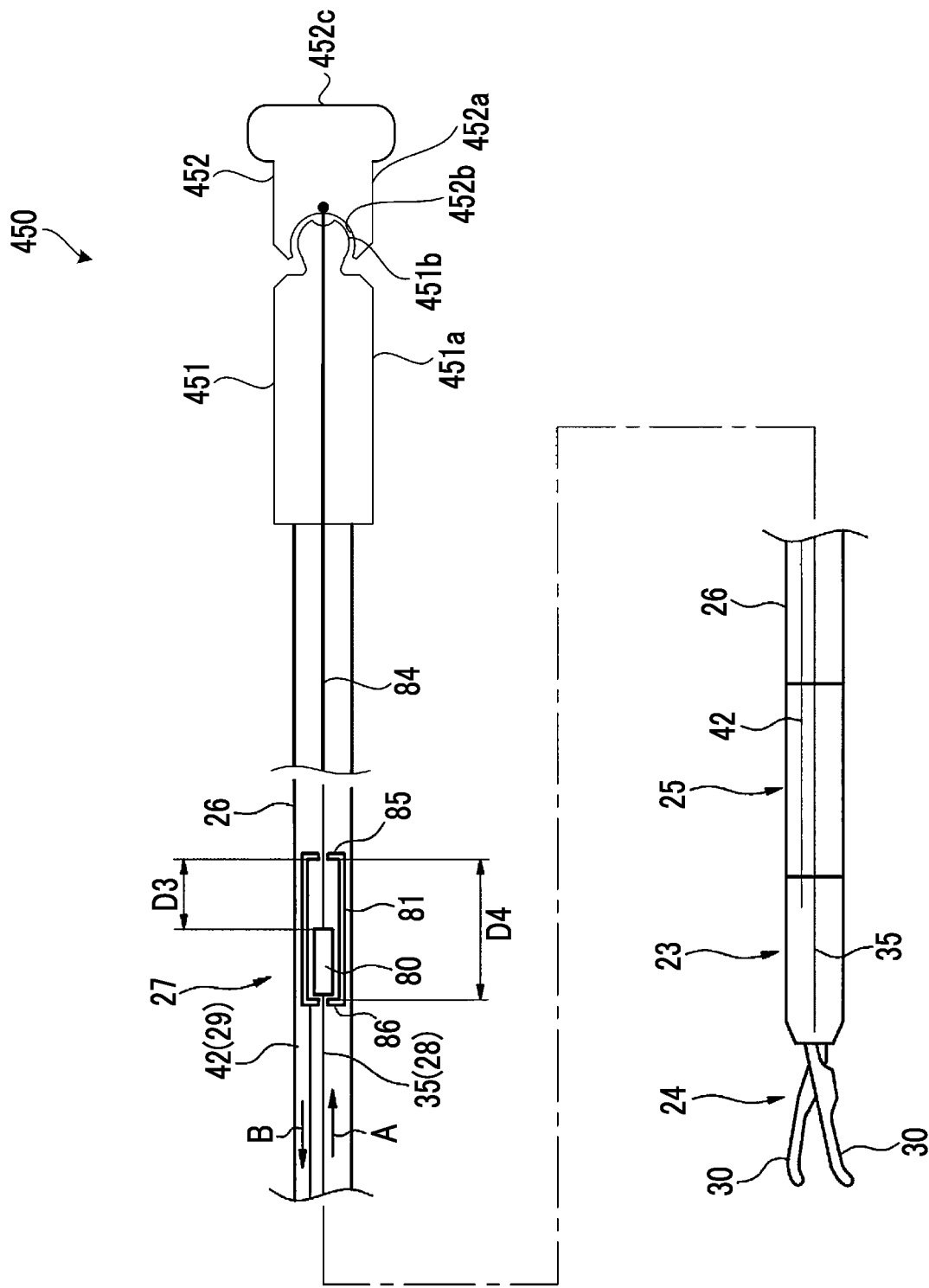
FIG. 45 is a view showing Modification Example 4 of the operating part of the treatment tool for an endoscope, which is for describing Embodiment 2 of the present invention.
Figure 46:
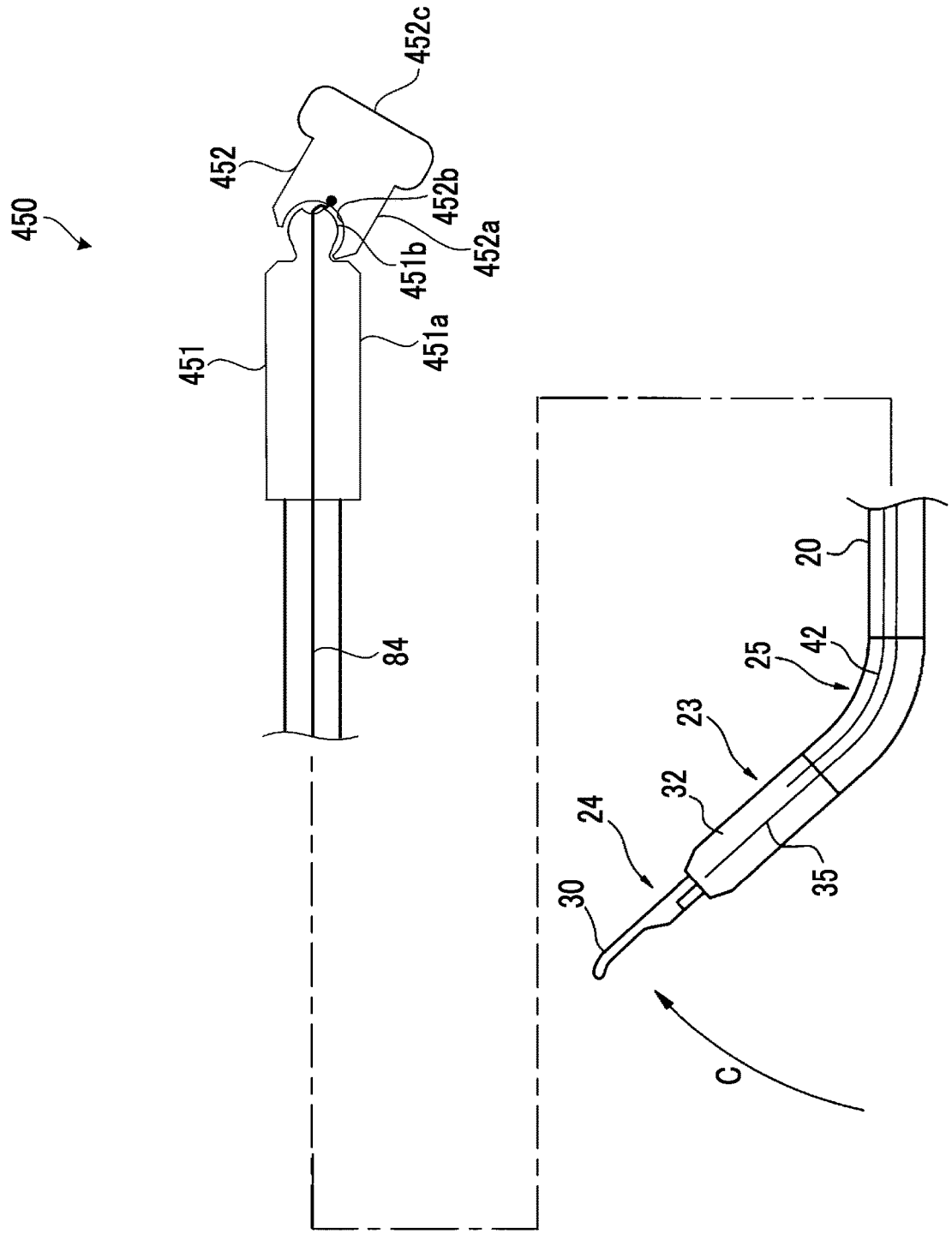
FIG. 46 is a view showing operations of the grip part 24 and the bendable part 25 of FIG. 45.

FIG. 45 is a view showing Modification Example 4 of the operating part of the treatment tool for an endoscope, which is for describing Embodiment 2 of the present invention. In a configuration where the transmitting part 27 is provided at the soft portion 26 as in the configuration shown in FIG. 17, a joystick-type operating part 450 may be provided as shown in FIGS. 45 and 46, instead of the operating part 22. The operating part 450 has an operating part body 451 and a lever part 452.

The operating part body 451 has a gripped part 451a and a spherical convex part 451b. The gripped part 451a is formed in a cylindrical shape, and is gripped by, for example, the palm and four fingers excluding the thumb of one hand of the user. The spherical convex part 451b is a convex part that is spherical, and is provided on an upper surface side of the cylindrical gripped part 451a. At a portion of the spherical convex part 451b, which is on an opposite side to the operating part body 451, a depression in a spherical surface is provided.

The lever part 452 has a support column part 452a, a spherical concave part 452b, and a finger placing part 452c. The support column part 452a is formed in a cylindrical shape. In a state where the lever part 452 is not operated, an axial direction of the support column part 452a and an axial direction of the gripped part 451a match each other as shown in FIG. 45.

The spherical concave part 452b is a spherical concave part slightly larger than the spherical convex part 451b, and is provided on a lower surface side of the support column part 452a. The finger placing part 452c is a portion where the thumb of the user gripping the gripped part 451a is placed, and is provided on a side of the lever part 452, which is opposite to the spherical concave part 452b. The finger placing part 452c is formed in a chamfered cylindrical shape.

The spherical concave part 452b is fitted to the spherical convex part 451b, and is in a universal joint structure. Accordingly, the lever part 452 is movable rotationally about the spherical convex part 451b. As the user gripping the operating part 450 operates the finger placing part 452c with the thumb, the lever part 452 can be tilted with respect to the operating part body 451.

The operating part body 451 has a through hole in the axial direction, and the connecting wire 84 passes through the through hole. Although not shown in detail, one opening portion of the through hole is provided in the middle of a lower surface of the support column part 452a, and the other opening portion of the through hole is provided in the middle of the depression in the spherical surface of the spherical convex part 451b. The connecting wire 84 is movable in the A-direction and the B-direction with respect to the operating part body 451, inside the through hole.

One end of the connecting wire 84 is fixed to a portion of the spherical concave part 452b of the lever part 452, which faces the middle of the depression of the spherical convex part 451b in the state shown in FIG. 45. In a case where an operation of tilting the lever part 452 with respect to the operating part body 451 is performed in the state shown in FIG. 45, one end of the connecting wire 84, which is fixed to the spherical concave part 452b, is separated from the middle of the depression of the spherical convex part 451b as shown in FIG. 46. Therefore, in response to the operation of tilting the lever part 452 with respect to the operating part body 451, the centers of the universal joints are shifted from each other, a passage of the connecting wire 84 in the operating part 450 becomes longer, and the connecting wire 84 is pulled to move in the A-direction.

An operation of the transmitting part 27 accompanying the movement of the connecting wire 84 in the A-direction is the same as the example shown in FIG. 17. For example, in a state where the lever part 452 is not tilted with respect to the operating part body 451 as shown in FIG. 45, the grip part 24 is open, and the bendable part 25 extends in a linear shape. From this state, in response to an operation of tilting the lever part 452 with respect to the operating part body 451, first, the grip part 24 is closed like the grip part 24 shown in FIG. 11, and next, the bendable part 25 is bent as shown in FIG. 46.

As described above, in the operating part 450 of Modification Example 4, by adopting a configuration where the lever part 452 that can be tilted with respect to the gripped part 451a with an operation of the thumb of the hand of the user gripping the gripped part 451a is included, and in response to the tilting of the lever part 452 with respect to the gripped part 451a, first, the first slider 80 is moved in the A-direction, and the second slider 81 moves in the A-direction after the start of the movement of the first slider 80, the gripping of the lesion part and the lifting of the gripped lesion part can be performed with an operation that makes it easy to exert a force, which is tilting the lever part 452 with the thumb of the hand gripping the gripped part 451a.

In addition, since the connecting wire 84 is configured to be pulled according to the amount of tilting the lever part 452 regardless of a direction in which the lever part 452 is tilted, the gripping of the lesion part and the lifting of the gripped lesion part can be similarly performed even in a case where the lever part 452 falls down in any direction. For this reason, the user can perform an operation without considering a direction of the operating part 450 in a case of gripping the operating part 450 and the direction in which the lever part 452 is tilted.

In addition, in the operating part 450 of Modification Example 4, the lever part 452 is fitted to the gripped part 451a (operating part body 451) so as to be movable rotationally, and the connecting wire 84 (third transmitting member) moves inside the gripped part 451a in response to the rotational movement of the lever part 452. Then, in response to the movement of the connecting wire 84, first, the first slider 80 is configured to be moved in the A-direction, and the second slider 81 is configured to move in the A-direction after the start of the movement of the first slider 80.

Figure 47:
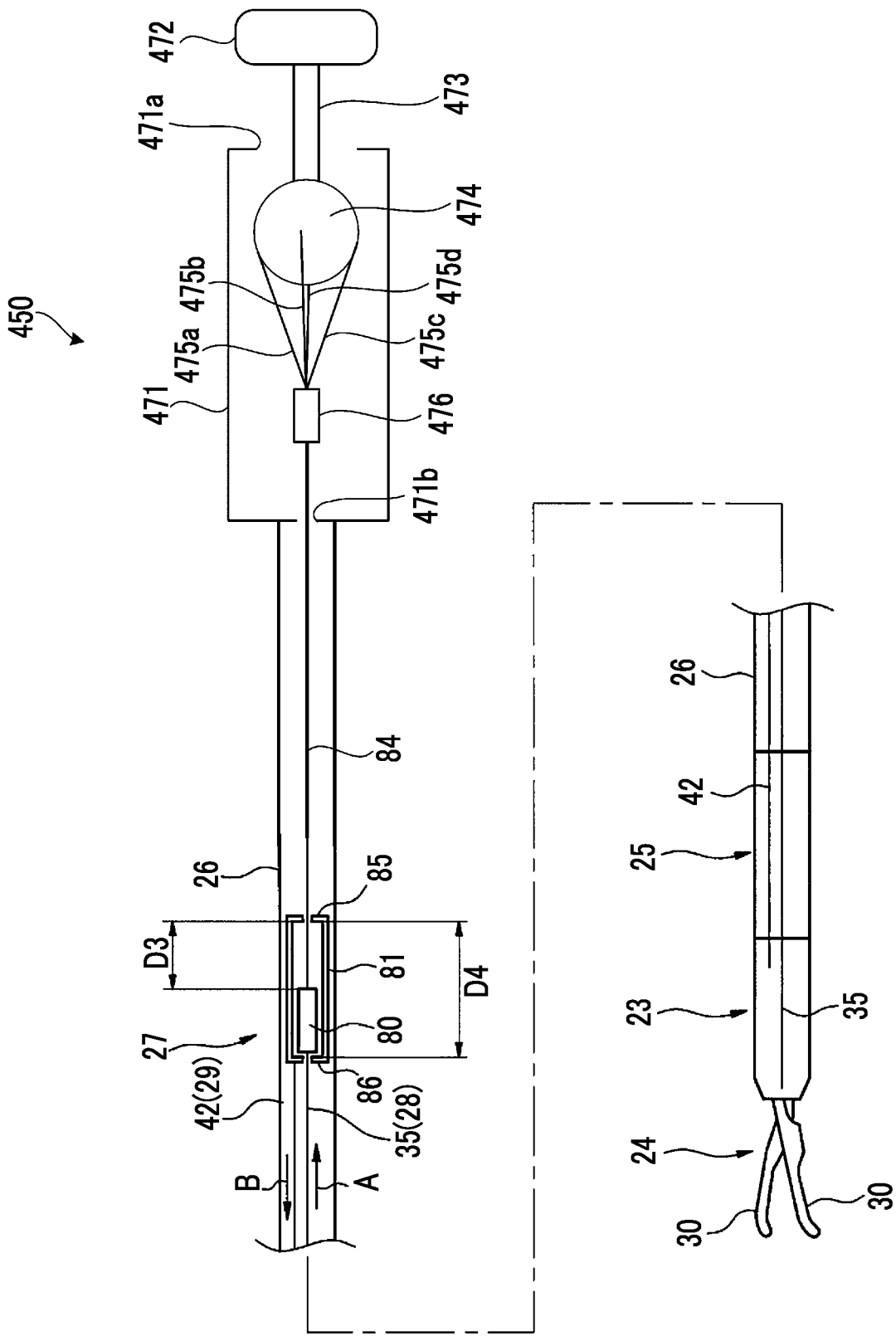
FIG. 47 is a view showing Modification Example 5 of the operating part of the treatment tool for an endoscope, which is for describing Embodiment 2 of the present invention.

FIG. 47 is a view showing Modification Example 5 of the operating part of the treatment tool for an endoscope, which is for describing Embodiment 2 of the present invention. In addition, in the configuration where the transmitting part 27 is provided at the soft portion 26 as in the configuration shown in FIG. 17, a joystick-type operating part 470 may be provided as shown in FIG. 47, instead of the operating part 22. The operating part 470 has a gripped part 471, a finger placing part 472, a support column part 473, a sphere 474, wires 475a to 475d, and a connecting portion 476.

The gripped part 471 is formed in a hollow cylindrical shape, and is gripped by, for example, the palm and four fingers excluding the thumb of one hand of the user. The gripped part 471 has an opening portion 471a in an upper surface thereof, and has an opening portion 471b in a lower surface c. The sphere 474, the wires 475a to 475d, and the connecting portion 476 are provided inside the hollow gripped part 471.

The finger placing part 472 and the support column part 473 are examples of a lever part that can be tilted with respect to the gripped part 471. The finger placing part 472 is a portion where the thumb of the user gripping the gripped part 471 is placed, and is formed in a chamfered cylindrical shape.

The support column part 473 is a member that is formed in a cylindrical shape and connects the finger placing part 472 outside the gripped part 471 to the sphere 474 inside the gripped part 471. The support column part 473 is movable in the opening portion 471a of the gripped part 471. In a state where the gripped part 471 is not operated, an axial direction of the support column part 473 and an axial direction of the gripped part 471 match each other as shown in FIG. 47.

The sphere 474 is an example of a rotational movement body that is provided so as to be movable rotationally inside the gripped part 471 and is connected to the finger placing part 472 and the support column part 473. The finger placing part 472 and support column part 473 are movable rotationally about the sphere 474. As the user gripping the operating part 470 operates the finger placing part 472 with the thumb, the finger placing part 472 and the support column part 473 can be tilted with respect to the gripped part 471.

The wires 475a to 475d are four wires having the same length, and are provided so as to be movable inside the gripped part 471. A first end of each of the wires 475a to 475d is fixed to the connecting portion 476. A second end of each of the wires 475a to 475d is fixed at four places on the surface of the sphere 474. The four places are four places at equal intervals on an outer periphery of a cross section in a case where the sphere 474 is bisected by a plane orthogonal to the axial direction of the support column part 473.

The connecting portion 476 is a member that connects one end of the connecting wire 84 to the first end of each of the wires 475a to 475d, and is provided so as to be movable inside the gripped part 471. The connecting wire 84 is connected from the connecting portion 476 to the transmitting part 27 through the opening portion 471b of the gripped part 471.

Figure 48:
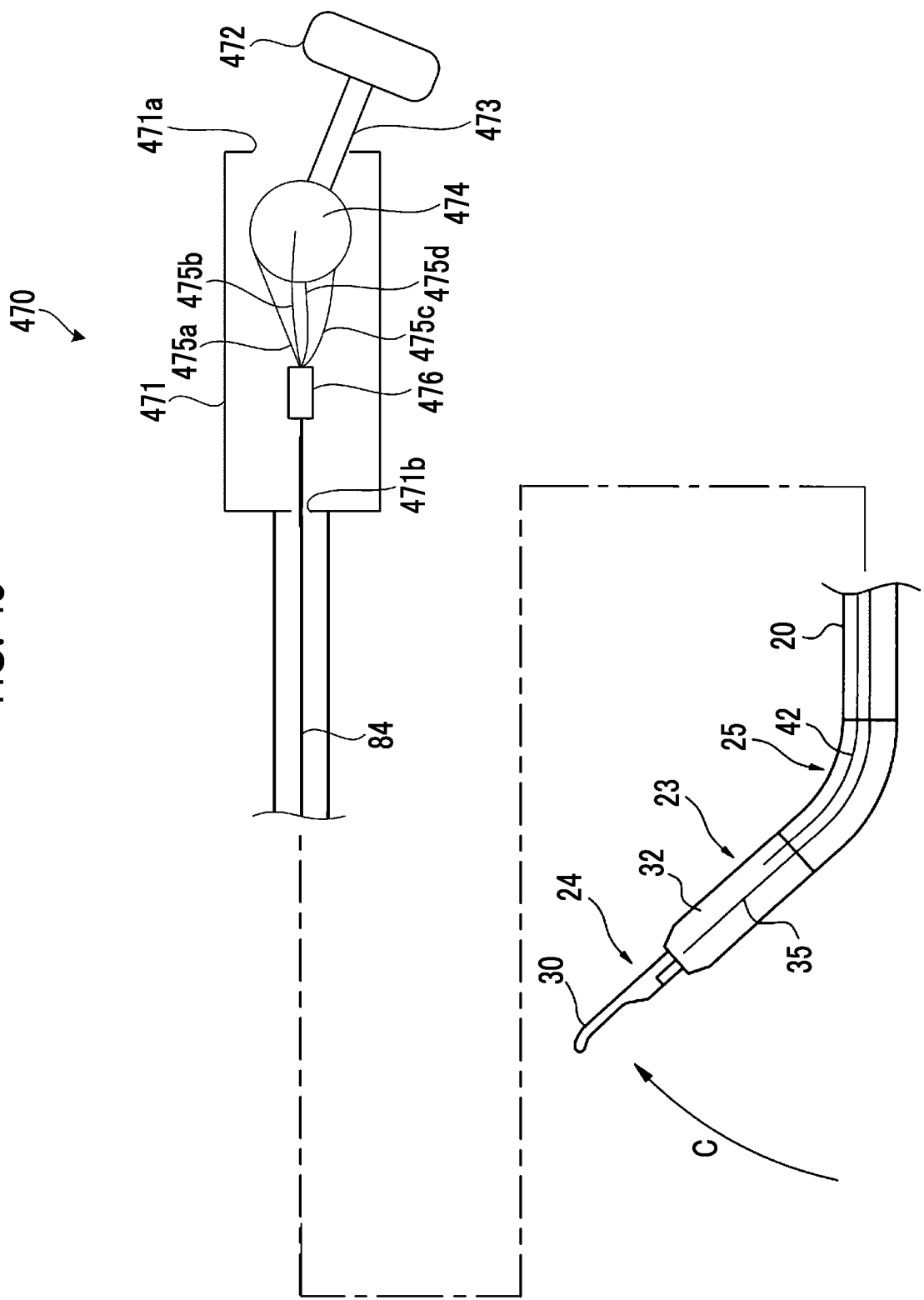
FIG. 48 is a view showing operations of the grip part 24 and the bendable part 25 of FIG. 47.

In a case where an operation of tilting the finger placing part 472 and the support column part 473 with respect to the gripped part 471 is performed in a state shown in FIG. 47, the sphere 474 rotates. As shown in FIG. 48, due to the rotation of the sphere 474, at least any one of the four wires 475a to 475d is pulled to an opposite direction to the connecting portion 476, and the connecting portion 476 moves in the A-direction. In an example of FIG. 48, the connecting portion 476 is pulled in the A-direction by pulling the wire 475a. Among the four wires 475a to 475d, a wire that is not pulled by the rotation of the sphere 474 does not hinder the movement of the connecting portion 476 in the A-direction by bending.

An operation of the transmitting part 27 accompanying the movement of the connecting wire 84 in the A-direction is the same as the example shown in FIG. 17. For example, in a state where the finger placing part 472 and the support column part 473 are not tilted with respect to the gripped part 471 as shown in FIG. 47, the grip part 24 is open, and the bendable part 25 extends in a linear shape. From this state, in response to an operation of tilting the finger placing part 472 and the support column part 473 with respect to the gripped part 471, first, the grip part 24 is closed like the grip part 24 shown in FIG. 11, and next, the bendable part 25 is bent as shown in FIG. 48.

As described above, in the operating part 470 of Modification Example 5, by adopting a configuration where the finger placing part 472 and the support column part 473 (lever parts) that can be tilted with respect to the gripped part 471 with an operation of the thumb of the hand of the user gripping the gripped part 471 are included, and in response to the tilting of the finger placing part 472 and the support column part 473 (lever parts) with respect to the gripped part 471, first, the first slider 80 is moved in the A-direction, and the second slider 81 moves in the A-direction after the start of the movement of the first slider 80, the gripping of the lesion part and the lifting of the gripped lesion part can be performed with an operation that makes it easy to exert a force, which is tilting the finger placing part 472 and the support column part 473 (lever parts) with the thumb of the hand gripping the gripped part 471.

In addition, since the connecting wire 84 is configured to be pulled according to the amount of tilting the finger placing part 472 and the support column part 473 regardless of the direction in which the finger placing part 472 and the support column part 473 are tilted, the gripping of the lesion part and the lifting of the gripped lesion part can be similarly performed even in a case where the finger placing part 472 and the support column part 473 fall down in any direction. For this reason, the user can perform an operation without considering a direction of the operating part 470 in a case of gripping the operating part 470 and the direction in which the finger placing part 472 and the support column part 473 are tilted.

In addition, the operating part 470 of Modification Example 5 has the sphere 474 (rotational movement body) that is movable rotationally inside the gripped part 471 and connects the finger placing part 472 to the support column part 473 (lever parts) and the wires 475a to 475d that are fixed at positions on the sphere 474 different from each other and are connected to the connecting wire 84. Then, in response to the rotational movement of the sphere 474, the connecting wire 84 is pulled by some of the wires 475a to 475d and moves inside gripped part 471. In response to the movement of the connecting wire 84, first, the first slider 80 is configured to be moved in the A-direction, and the second slider 81 is configured to move in the A-direction after the start of the movement of the first slider 80.

Figure 49:
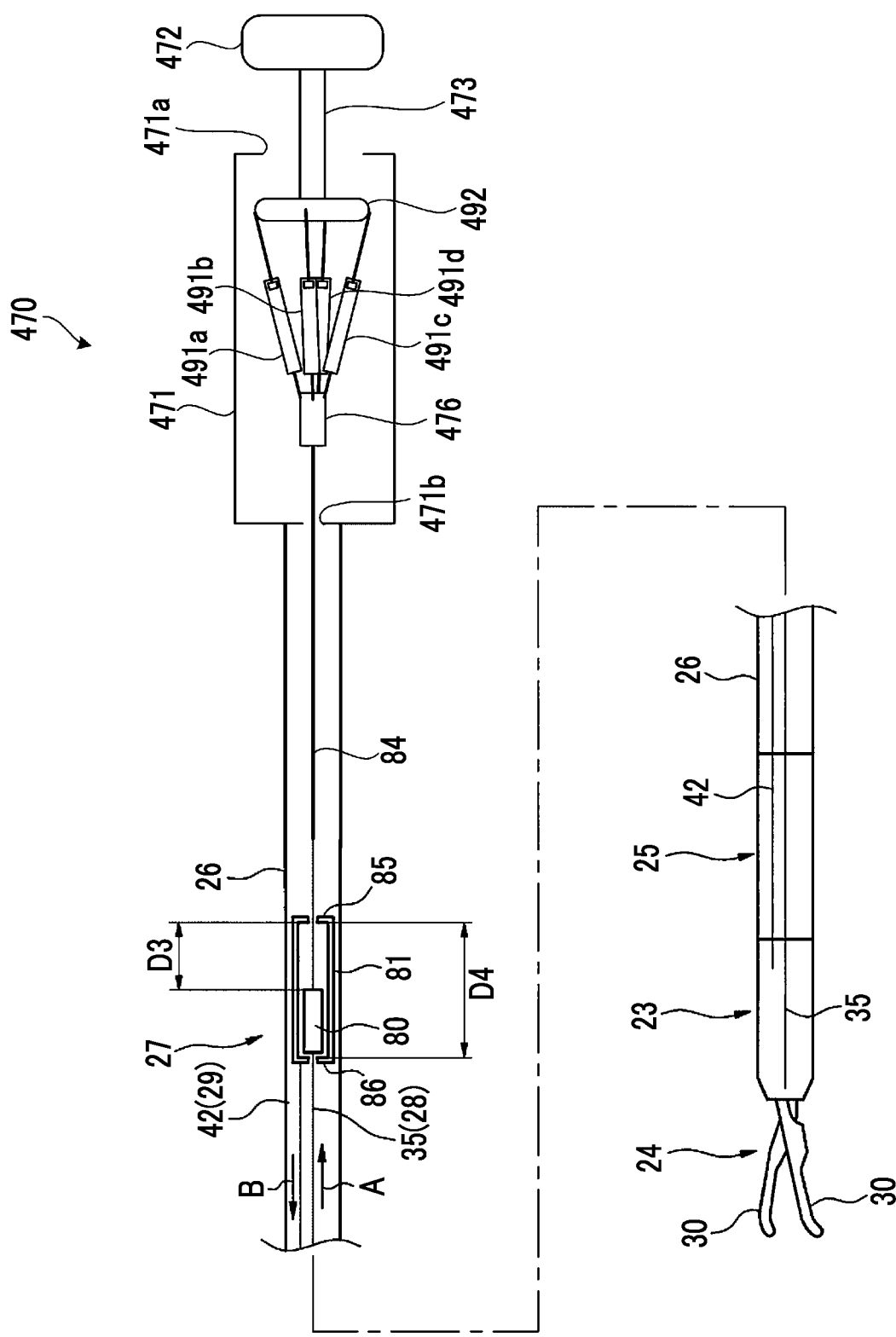
FIG. 49 is a view showing Modification Example 6 of the operating part of the treatment tool for an endoscope, which is for describing Embodiment 2 of the present invention.

FIG. 49 is a view showing Modification Example 6 of the operating part of the treatment tool for an endoscope, which is for describing Embodiment 2 of the present invention. For example, as shown in FIG. 49, dampers 491a to 491d and a disk body 492 may be provided in the configuration shown in FIGS. 47 and 48, instead of the wires 475a to 475d and the sphere 474. The dampers 491a to 491d are, for example, flexible stiff members using a piston. The disk body 492 is an example of a rotational movement body that is provided so as to be movable rotationally inside the gripped part 471 and is connected to the finger placing part 472 and the support column part 473.

Figure 50:
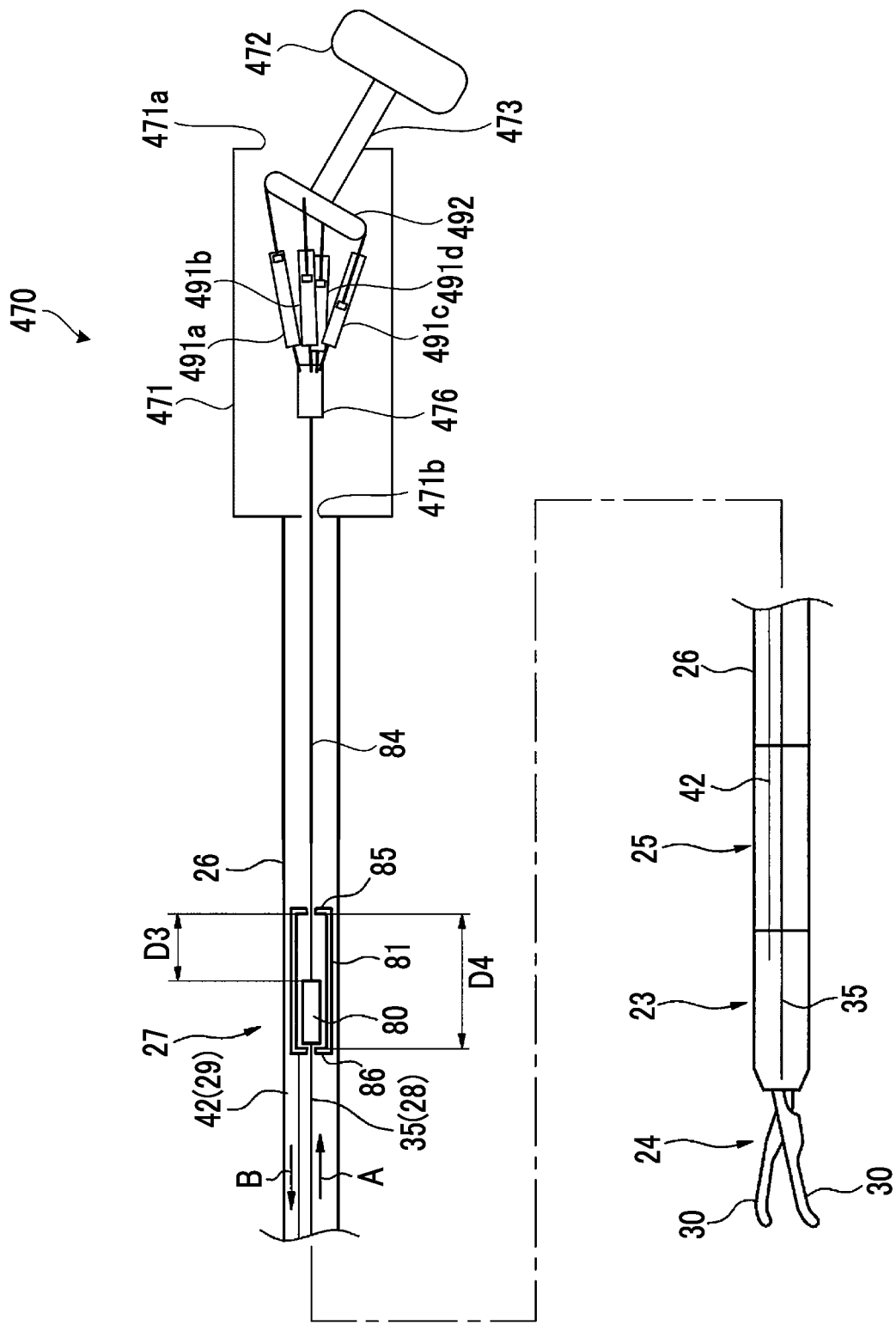
FIG. 50 is a view showing operations of the grip part 24 and the bendable part 25 of FIG. 49.

Even though the dampers 491a to 491d are used instead of the wires 475a to 475d, in a case of performing an operation of tilting the finger placing part 472 and the support column part 473 with respect to the gripped part 471, the connecting portion 141 are pulled in the A-direction by pulling some of the dampers and other dampers shorten as shown in FIG. 50. Thus, the movement of the connecting portion 476 in the A-direction is not hindered.

Although a configuration where the disk body 492 is provided instead of the sphere 474 in order to make connecting the dampers 491a to 491d, which are stiff members, easier has been described, a configuration where the sphere 474 is provided instead of the disk body 492 may be adopted in an example of FIGS. 49 and 50.

As described above, in the operating part 470 of Modification Example 6, by providing the dampers 491a to 491d (flexible members) instead of the wires 475a to 475d, the same effects as the operating part 470 of Modification Example 5 can be obtained.

Each of the modification examples of the operating part described in Embodiment 2 is applicable to each configuration of Embodiment 1. For example, although a configuration where the transmitting part 27 shown in FIGS. 10 to 12 is used has been described in Embodiment 2, without being limited thereto, for example, a configuration where the transmitting part 27 shown in FIGS. 14 to 16 is used may be adopted. In addition, although a configuration where the transmitting part 27 is provided at the soft portion 26 has been described in Embodiment 2, a configuration where the transmitting part 27 is provided at a portion other than the soft portion 26 (for example, the operating part) may be adopted.

In addition, although a case where the grip part 24 is closed and the bendable part 25 is bent in response to an operation has been described in Embodiment 2, as in the example shown in Embodiment 1, a configuration where the grip part 24 is opened and the bendable part 25 is restored to a linear shape by performing a reverse operation may be adopted.

Although various types of embodiments have been described hereinbefore with reference to the drawings, it is evident that the present invention is not limited to such examples. It is clear that those skilled in the art can come up with various types of changed examples or modified examples within the scope of claims, and it is understood that those examples obviously belong to the technical scope of the present invention. In addition, without departing from the gist of the invention, each of components in the embodiments may be combined in any manner.

This application is based on the U.S. provisional application filed on Sep. 6, 2019 (62/896,584) and the U.S. provisional application filed on Aug. 12, 2020 (63/064,894), the content of which is incorporated herein by reference.

EXPLANATION OF REFERENCES

1: endoscope system
2: endoscope
3: light source device
4: processor
5: monitor
6: endoscope insertion part
7: endoscope operating part
8: universal cord
9: connector
10: endoscope distal end part
11: endoscope bendable part
12: endoscope soft portion
13: first treatment tool insertion opening
14: first treatment tool channel
15: second treatment tool insertion opening
16: second treatment tool channel
20: endoscope treatment tool
21: insertion part
22: operating part 23: distal end part
24: grip part
25: bendable part
26: soft portion
27: transmitting part
28: first transmitting member
29: second transmitting member
30: grip claw
31: link member
32: support
33: pin
34: pin
35: wire (first transmitting member)
35: wire
36: flexible part
40: cyclic member
40A: first portion
40B: second portion
41: pin
42: wire (second transmitting member)
42: wire
43: first guide
44: second guide
45: elastic member
50: operating part body
51: operating handle
52: pin
53: free end part
60: first slider (first movable body)
60: first slider
61: second slider (second movable body)
61: second slider
62: link member
63: first abutting part
64: second abutting part
70: first rack (first movable body)
70: first rack
71: first pinion
72: second rack (second movable body)
72: second rack
73: second pinion
74: shaft
75: gear device
80: first slider (first movable body)
80: first slider
81: second slider (second movable body)
81: second slider
82: third slider
83: link member
84: connecting wire
85: first abutting part
86: second abutting part
90: high-frequency forcep
120: endoscope treatment tool
121: insertion part
125: bendable part
140: cyclic portion
140A: first portion
140B: second portion
141: connecting portion
220: endoscope treatment tool
221: insertion part
225: bendable part
240: tubular member
241: restraining member
320: endoscope treatment tool
321: insertion part
322: operating part
323: distal end part
324: grip part
325: bendable part
326: soft portion
327: transmitting part
328: first transmitting member
329: second transmitting member
330: grip claw
332: support
335: wire (first transmitting member)
335: wire
340: cyclic member
340A: first portion
340B: second portion
341: pin
342: wire (second transmitting member)
342: wire
343: first guide
344: second guide
350: operating part body
351: operating handle
353: free end part
360: first slider (first movable body)
360: first slider
361: second slider (second movable body)
361: second slider
362: link member
363 first abutting part
364: second abutting part
400: operating part
401: operating part body
402: handle member
402a: pin
402c: ring
403: handle member
403a: pin
403b: pin
403c: ring
404: link member
404a: pin
405: link member
405a: pin
405b: pin
420: endoscope treatment tool
421: insertion part
425: bendable part
440: cyclic portion
440A: first portion
440B: second portion
441: connecting portion
450: operating part
451: operating part body
451a: gripped part
451b: spherical convex part
452: lever part
452a: support column part
452b: spherical concave part
452c: finger placing part
470: operating part
471: gripped part
471a: opening portion
471b: opening portion
472: finger placing part
473: support column part
474: sphere
475a: wire 475b: wire
475c: wire
475d: wire
476: connecting portion
491a: damper
491b: damper
491c: damper
491d: damper
492: disk body
D1: interval
D2: interval
D3: interval
D4: interval
D5: interval
D6: interval
GA: gap
GB: gap
LA: lesion part
S: bent neutral plane
x: rotational movement shaft
X: central axis
θ1: central angle
θ2: central angle

What is claimed is:

1. A treatment tool for an endoscope comprising:

an insertion part that has a distal end part, which is provided with an openable and closable grip part, and a bendable part, which is provided adjacent to the distal end part and is bendable, and that is insertable into a body;

an operating part into which an operation of closing the grip part and an operation of bending the bendable part are input; and a transmitting part that transmits an operation of the operating part to the grip part and the bendable part, wherein the transmitting part has a first transmitting member that extends from the grip part toward the operating part, is moved in a first direction, which is a side of the operating part or a side of the distal end part, based on the operation of the operating part, and closes the grip part by being moved in the first direction, a second transmitting member that extends from the bendable part toward the operating part, is moved in the first direction based on the operation of the operating part, and bends the bendable part by being moved in the first direction, a first movable body that is connected to the first transmitting member and is moved in the first direction based on the operation of the operating part, and a second movable body that is connected to the second transmitting member and is moved in the first direction based on the operation of the operating part, and in response to the operation of the operating part, the first movable body is moved in the first direction, and the second movable body is moved in the first direction after a start of the first movable body being moved in the first direction, wherein the second movable body has a first abutting part that is disposed on a side of the first direction of the first movable body, in a case where the operating part is not operated, an interval is provided between the first movable body and the first abutting part, and a stroke of the first movable body moved in the first direction in response to the operation of the operating part is larger than the interval between the first movable body and the first abutting part.

2. The treatment tool for an endoscope according to claim 1, wherein the second movable body has a second abutting part that is disposed on a second direction side, opposite to the side of the first direction, of the first movable body, and an interval between the first abutting part and the second abutting part is smaller than the stroke of the first movable body.

3. The treatment tool for an endoscope according to claim 1, wherein the bendable part has an elastic member that restores the bent bendable part to a linear shape.

* * * * *